US011266331B2

United States Patent
Gomi et al.

(10) Patent No.: US 11,266,331 B2
(45) Date of Patent: Mar. 8, 2022

(54) OPTICAL APPARATUS AND INFORMATION PROCESSING METHOD

(71) Applicant: SONY CORPORATION, Tokyo (JP)

(72) Inventors: Shinichiro Gomi, Tokyo (JP); Kenichiro Nakamura, Saitama (JP); Yoichi Toriumi, Tokyo (JP); Morio Ogura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 571 days.

(21) Appl. No.: 16/099,080

(22) PCT Filed: May 2, 2017

(86) PCT No.: PCT/JP2017/017217
§ 371 (c)(1),
(2) Date: Nov. 5, 2018

(87) PCT Pub. No.: WO2017/199757
PCT Pub. Date: Nov. 23, 2017

(65) Prior Publication Data
US 2019/0133502 A1 May 9, 2019

(30) Foreign Application Priority Data

May 16, 2016 (JP) .............................. JP2016-097882

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0071* (2013.01); *A61B 5/1455* (2013.01);
(Continued)

(58) Field of Classification Search
CPC ... A61B 5/443; A61B 5/0071; A61B 5/14532; A61B 5/14546; A61B 5/1455; G06T 2207/10048
See application file for complete search history.

(56) References Cited

U.S. PATENT DOCUMENTS 6,436,127 B1 * 8/2002 Anderson ............ A61B 5/0064
128/898
7,966,060 B2 6/2011 Smit et al.
(Continued)

FOREIGN PATENT DOCUMENTS

CN 1617169 A 5/2005
CN 101304684 A 11/2008
(Continued)

OTHER PUBLICATIONS

International Search Report and Written Opinion of PCT Application No. PCT/JP2017/017217, dated Aug. 1, 2017, 07 pages of ISRWO.
(Continued)

*Primary Examiner* — Amelie R Davis
(74) *Attorney, Agent, or Firm* — Chip Law Group

(57) ABSTRACT

The present technology relates to an optical apparatus and an information processing method capable of more easily obtaining an indicator value. In the optical apparatus according to the present technology, irradiation light including a predetermined irradiation wavelength band is emitted, first reflected light being a reflected light in a first wavelength band obtained by reflection of the emitted irradiation light on a predetermined object and second reflected light being reflected light in a second wavelength band obtained by reflection of the irradiation light on the object are received at a plurality of pixels; and a value of a predetermined indicator relating to a region in a predetermined range of the object is obtained on the basis of a received light amount of each of the received first reflected light and the received second reflected light. For example, the present technology can be applied to optical apparatuses, electronic apparatuses, imaging apparatuses, and information processing apparatuses.

17 Claims, 39 Drawing Sheets

(51) Int. Cl.
*G06T 7/00* (2017.01)
*A61B 5/1455* (2006.01)
(52) U.S. Cl.
CPC .......... *A61B 5/14546* (2013.01); *A61B 5/443* (2013.01); *G06T 7/0012* (2013.01); *G06T 2207/10048* (2013.01)

(56) References Cited

U.S. PATENT DOCUMENTS

| | | | | |
|---|---|---|---|---|
| 2007/0276199 | A1* | 11/2007 | Ediger | A61B 5/443 600/300 |
| 2011/0121200 | A1* | 5/2011 | Watanabe | G01J 3/10 250/458.1 |
| 2014/0028824 | A1* | 1/2014 | Kubo | A61B 1/043 348/77 |

FOREIGN PATENT DOCUMENTS

| | | |
|---|---|---|
| CN | 101528116 A | 9/2009 |
| EP | 0567447 A | 10/1993 |
| JP | 2012-235891 A | 12/2012 |
| JP | 2014-140423 A | 8/2014 |
| JP | 2015-159942 A | 9/2015 |

OTHER PUBLICATIONS

Office Action for CN Patent Application No. 201780028721.5 dated Mar. 31, 2021, 05 pages of Office Action and 11 pages of English Translation.

* cited by examiner

FIG. 8

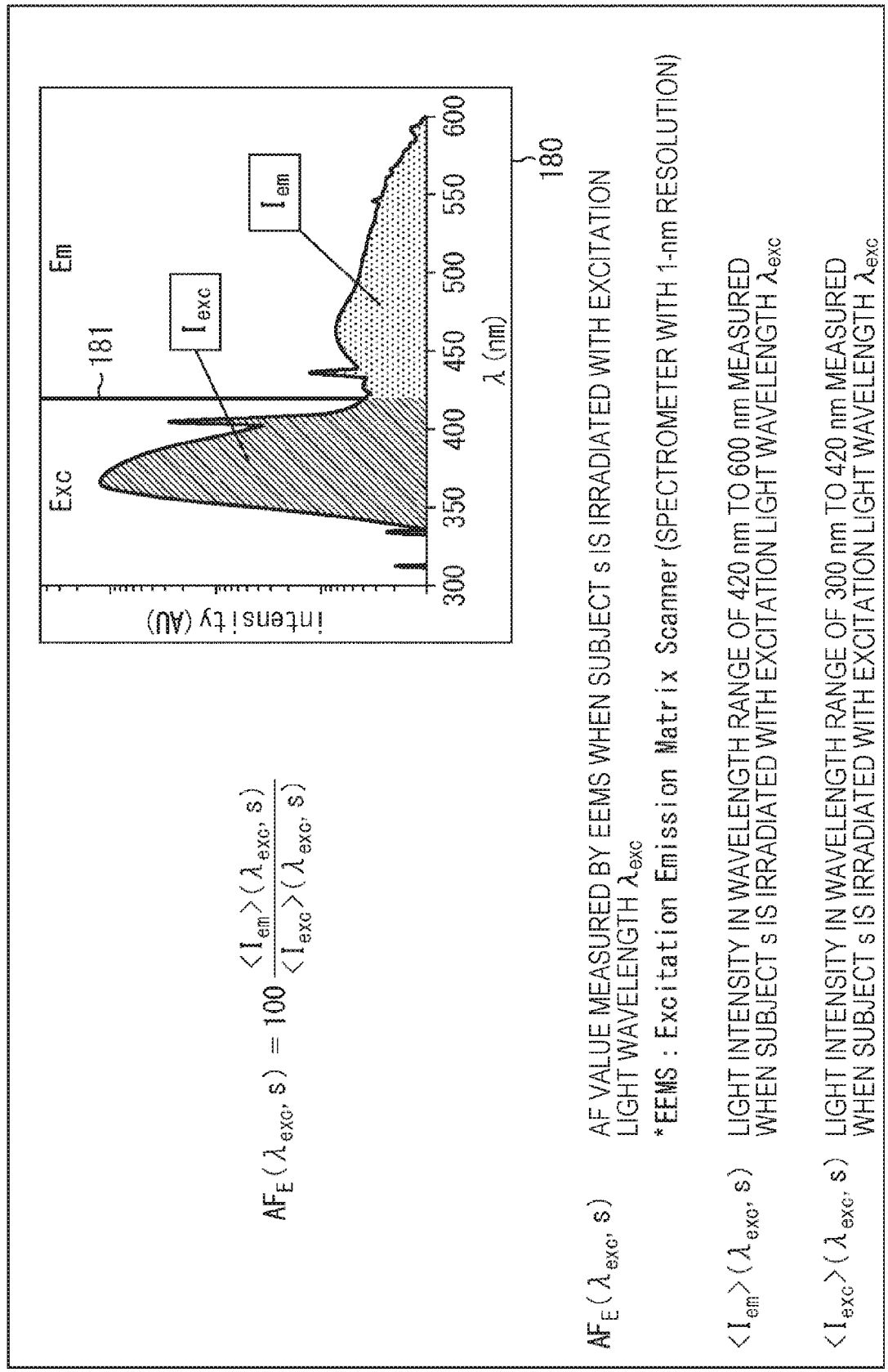

$$AF_E(\lambda_{exc}, s) = 100 \frac{\langle I_{em} \rangle (\lambda_{exc}, s)}{\langle I_{exc} \rangle (\lambda_{exc}, s)}$$

$AF_E(\lambda_{exc}, s)$  AF VALUE MEASURED BY EEMS WHEN SUBJECT s IS IRRADIATED WITH EXCITATION LIGHT WAVELENGTH $\lambda_{exc}$
*EEMS : Excitation Emission Matrix Scanner (SPECTROMETER WITH 1-nm RESOLUTION)

$\langle I_{em} \rangle (\lambda_{exc}, s)$  LIGHT INTENSITY IN WAVELENGTH RANGE OF 420 nm TO 600 nm MEASURED WHEN SUBJECT s IS IRRADIATED WITH EXCITATION LIGHT WAVELENGTH $\lambda_{exc}$ $\langle I_{exc} \rangle (\lambda_{exc}, s)$  LIGHT INTENSITY IN WAVELENGTH RANGE OF 300 nm TO 420 nm MEASURED WHEN SUBJECT s IS IRRADIATED WITH EXCITATION LIGHT WAVELENGTH $\lambda_{exc}$

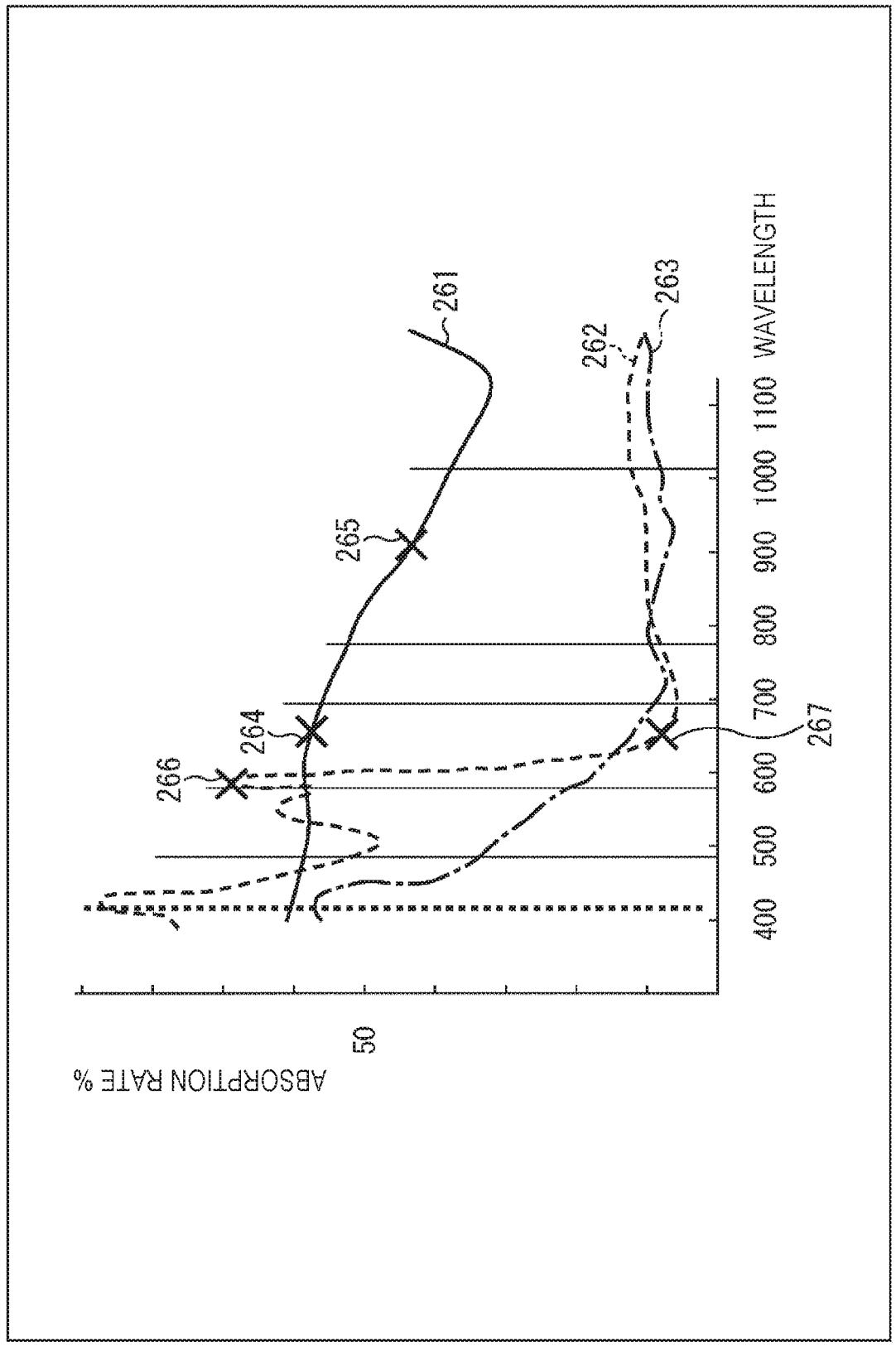

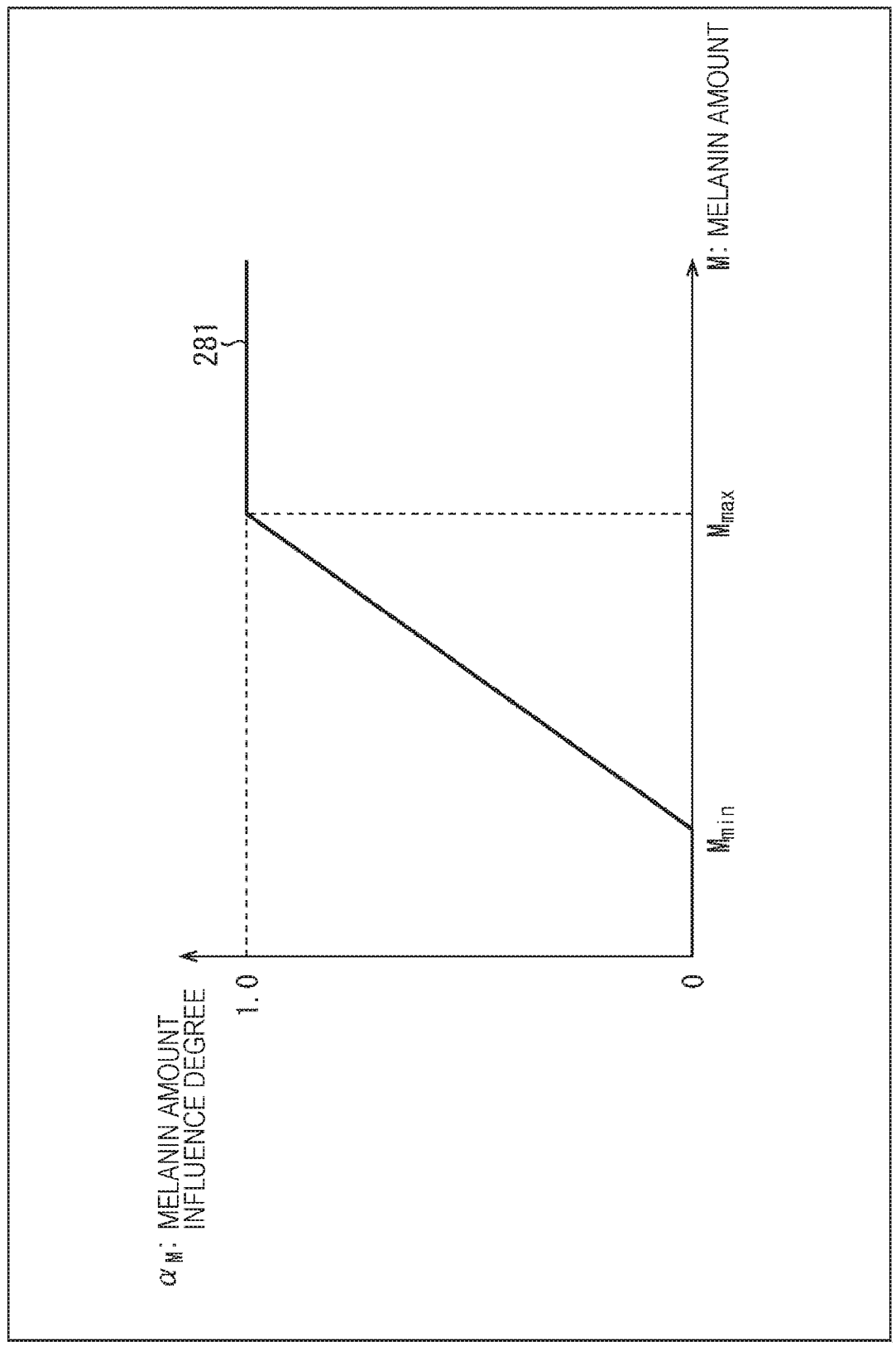

OPTICAL APPARATUS AND INFORMATION PROCESSING METHOD

CROSS REFERENCE TO RELATED APPLICATIONS

This application is a U.S. National Phase of International Patent Application No. PCT/JP2017/017217 filed on May 2, 2017, which claims priority benefit of Japanese Patent Application No. JP 2016-097882 filed in the Japan Patent Office on May 16, 2016. Each of the above-referenced applications is hereby incorporated herein by reference in its entirety.

TECHNICAL FIELD

The present technology relates to an optical apparatus and an information processing method, and in particular, to an optical apparatus and an information processing method capable of more easily obtaining an indicator value.

BACKGROUND ART

In the related art, there has been an apparatus that irradiates an object with light, receives reflected light thereof, and measures an indicator relating to advanced glycation endproducts (AGEs) (refer to, for example, Patent Document 1).

CITATION LIST

Patent Document

Patent Document 1: U.S. Pat. No. 7,966,060

SUMMARY OF THE INVENTION

Problems to be Solved by the Invention

However, in a measurement apparatus in the related art, since reflected light is received by a photodetector, only an indicator as a point can be obtained. Therefore, in a case where measurement error factors such as stains exist at the measurement position (the portion that reflects light) of the object, sufficiently accurate measurement cannot be performed. In such a case, troublesome work such as shifting the measurement position and performing the measurement is required.

In view of such situations, an object of the present technology is to more easily obtain an indicator value.

Solutions to Problems

An optical apparatus according to an aspect of the present technology includes: a light emitting unit that emits irradiation light including a predetermined irradiation wavelength band; a light receiving unit that receives, at a plurality of pixels, first reflected light being reflected light in a first wavelength band obtained by reflection of the irradiation light emitted by the light emitting unit on a predetermined object and second reflected light being reflected light in a second wavelength band obtained by reflection of the irradiation light on the object; and an indicator processing unit that obtains a value of a predetermined indicator relating to a region of a predetermined range of the object on the basis of a received light amount of each of the first reflected light and the second reflected light received by the light receiving unit.

The optical apparatus can further include a brightness adjustment unit that performs adjustment of brightness of a first reflection image being an image obtained by the light receiving unit receiving the first reflected light, a second reflection image being an image obtained by the light receiving unit receiving the second reflected light, or both of the first reflection image and the second reflection image.

The brightness adjustment unit can determine the brightness of the first reflection image by using average luminance of the first reflected light received by the light receiving unit, determine the brightness of the second reflection image by using average luminance or contrast of the second reflected light received by the light receiving unit, or perform both of the determining of the brightness of the first reflection image and the determining of the brightness of the second reflection image.

In a case where the brightness is insufficient, the brightness adjustment unit can increase the number of surrounding pixels, pixel values of the surrounding pixels being added to each pixel of the first reflection image and the second reflection image, increase a light amount of the irradiation light emitted by the light emitting unit, increases an exposure time of the light receiving unit, or perform a plurality of the increasing of the number of surrounding pixels, the increasing of the light amount of the irradiation light, and the increasing of the exposure time.

The brightness adjustment unit can perform the adjustment of the brightness of the first reflection image, the second reflection image, or both of the first reflection image and the second reflection image for each pixel or for each predetermined partial region including a plurality of pixels.

The optical apparatus can further include an indicator updating unit that updates the value of the indicator obtained by the indicator processing unit on the basis of a predetermined error factor.

The optical apparatus can further include an effectiveness degree processing unit that obtains an effectiveness degree of the value of the indicator on the basis of the error factor, and the indicator updating unit can be configured to update the value of the indicator by using the effectiveness degree obtained by the effectiveness degree processing unit.

The optical apparatus can further include an influence degree processing unit that obtains an influence degree by the error factor, and the effectiveness degree processing unit can be configured to obtain the effectiveness degree by using the influence degree obtained by the influence degree processing unit.

The optical apparatus can further include an error factor amount processing unit that obtains an amount of the error factor, and the influence degree processing unit can be configured to obtain the influence degree by using the amount of the error factor obtained by the error factor amount processing unit.

The error factor can be melanin, and the error factor amount processing unit can be configured to obtain an amount of the melanin by using a near-infrared image being an image obtained by the light receiving unit receiving light in a near-infrared wavelength band and a red image being an image obtained by the light receiving unit receiving light in a red wavelength band.

The error factor can be redness, and the error factor amount processing unit can be configured to obtain an amount of the redness by using a red image being an image obtained by the light receiving unit receiving light in a red wavelength band and a green image being an image obtained by the light receiving unit receiving light in a green wavelength band.

The indicator updating unit can be configured to update the value of the indicator for each pixel, for each predetermined partial region including a plurality of pixels or for a part of the region.

The optical apparatus can further include an indicator control unit that controls an output of the value of the indicator obtained by the indicator processing unit on the basis of a predetermined error factor.

The optical apparatus can further include an effectiveness degree processing unit that obtains an effectiveness degree of the value of the indicator on the basis of the error factor, and the indicator control unit can be configured to control the output of the value of the indicator by using an integrated value of the effectiveness degree obtained by the effectiveness degree processing unit.

The indicator control unit can output the value of the indicator in a case where the integrated value is larger than a predetermined threshold value and perform error processing in a case where the integrated value is equal to or smaller than the predetermined threshold value.

The irradiation wavelength band can be a near-ultraviolet wavelength band, and the light emitting unit can be configured to emit near-ultraviolet light being light in a near-ultraviolet wavelength band as the irradiation light.

The first wavelength band can be a near-ultraviolet to blue wavelength band, and the second wavelength band can be a blue to red wavelength band.

The light receiving unit can include a CMOS image sensor (CIS) that receives the first reflected light and a CIS that receives the second reflected light, include a CIS having a first pixel region receiving the first reflected light and a second pixel region receiving the second reflected light, or include a CIS having a pixel provided with a first on-chip filter that transmits the wavelength band of the first reflected light and a pixel provided with a second on-chip filter that transmits the wavelength band of the second reflected light, the CIS receiving the first reflected light in a pixel provided with the first on-chip filter and receiving the second reflected light in a pixel provided with the second on-chip filter.

The object can be a living body, and the indicator can be skin autofluorescence.

An information processing method according to an aspect of the present technology includes: emitting irradiation light including a predetermined irradiation wavelength band, receiving, at a plurality of pixels, first reflected light being a reflected light in a first wavelength band obtained by reflection of the emitted irradiation light on a predetermined object and second reflected light being reflected light in a second wavelength band obtained by reflection of the irradiation light on the object; and obtaining a value of a predetermined indicator relating to a region in a predetermined range of the object on the basis of a received light amount of each of the received first reflected light and the received second reflected light.

In the optical apparatus and the information processing method according to an aspect of the present technology, irradiation light including a predetermined irradiation wavelength band is emitted, first reflected light being a reflected light in a first wavelength band obtained by reflection of the emitted irradiation light on a predetermined object and second reflected light being reflected light in a second wavelength band obtained by reflection of the irradiation light on the object are received at a plurality of pixels; and a value of a predetermined indicator relating to a region in a predetermined range of the object is obtained on the basis of a received light amount of each of the received first reflected light and the received second reflected light.

Effects of the Invention

According to the present technology, measurement using light can be performed. Furthermore, according to the present technology, it is possible to more easily obtain an indicator value.

BRIEF DESCRIPTION OF DRAWINGS

FIG. 8 is a diagram illustrating an example of a state of SAF calculation.

FIG. 26 is a diagram illustrating an example of an absorption rate for each wavelength.

FIG. 28 is a diagram illustrating an example of calculation of a melanin amount influence degree.

MODE FOR CARRYING OUT THE INVENTION

Hereinafter, modes (hereinafter, referred to as embodiments) for carrying out the present disclosure will be described. In addition, the description will be made in the following order.

1. Measurement of Indicator Relating to Advanced Glycation Endproducts
2. First Embodiment (Measurement Apparatus: Brightness Adjustment)
3. Second embodiment (Measurement Apparatus: Indicator Value Correction)
4. Third embodiment (Measurement Apparatus: Indicator Value Output Control)
5. Application Example
6. Others

1. Measurement of Indicator Relating to Advanced Glycation Endproducts

<AGEs Measurement Instrument>

Figure 1:
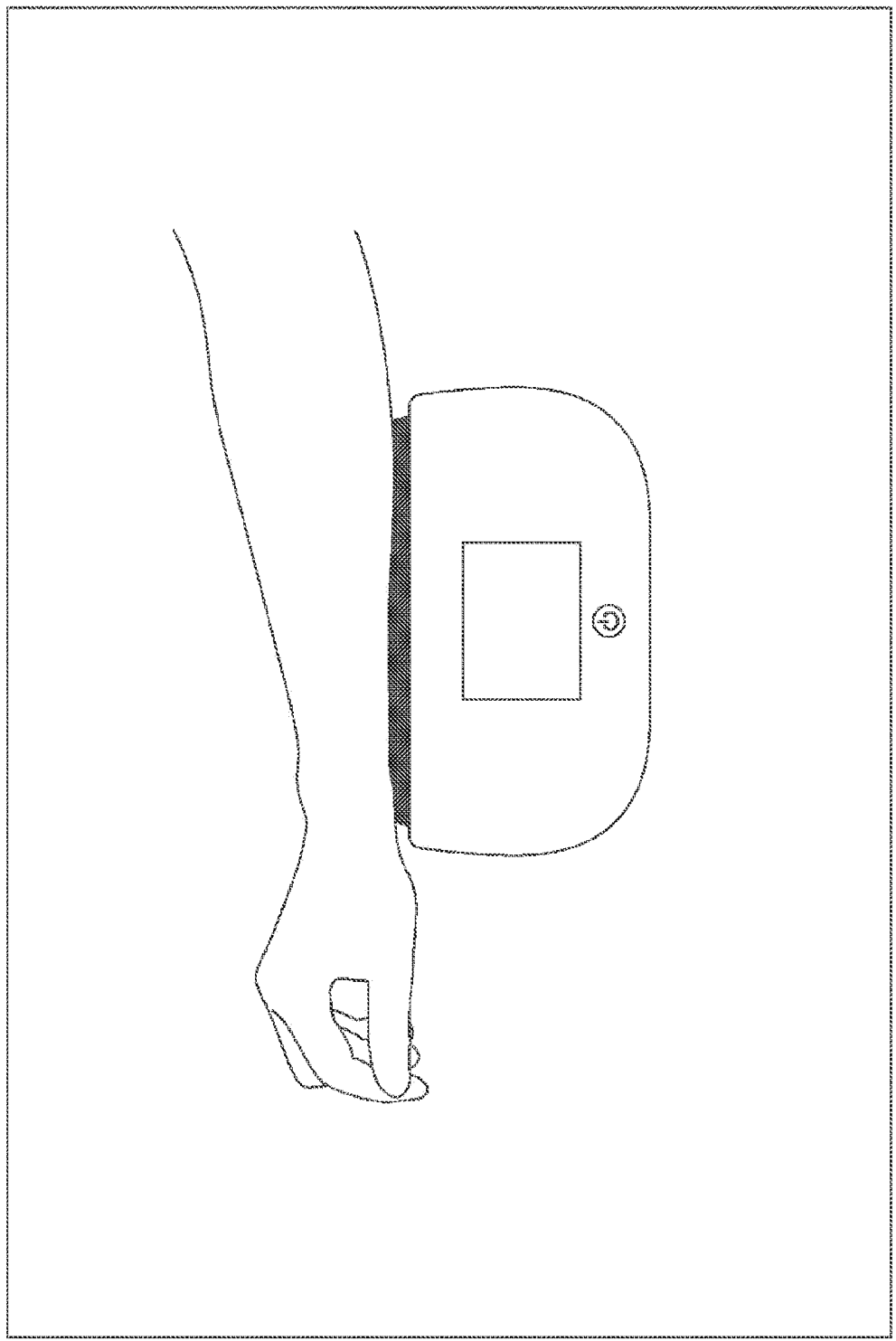
FIG. 1 is a diagram illustrating an example of a measurement instrument in the related art.
Figure 2:
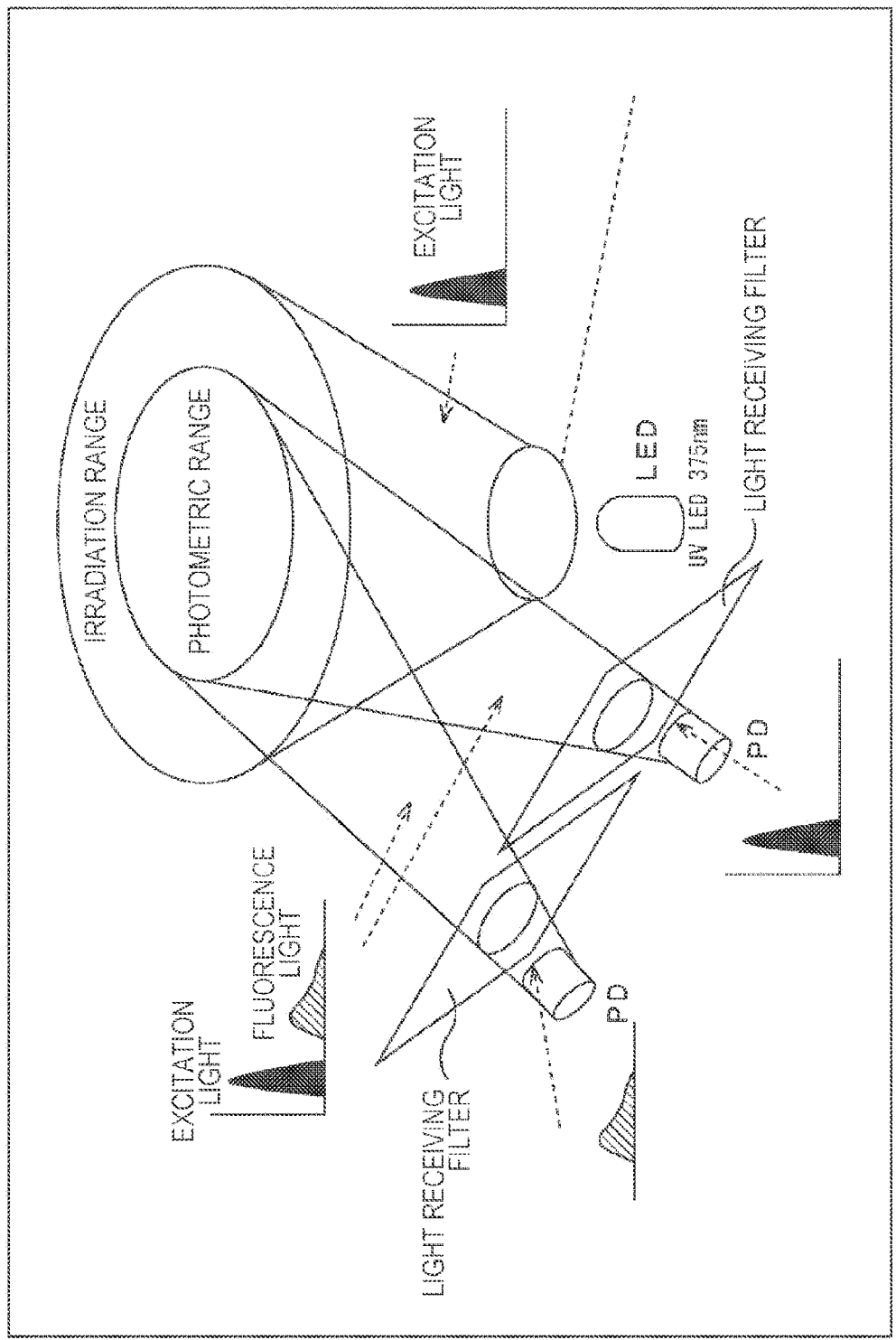
FIG. 2 is a diagram illustrating a configuration of a measurement instrument in the related art.

For example, as illustrated in FIG. 1, there is a device that irradiates an object with irradiation light, receives reflected light, and measures an indicator relating to advanced glycation endproducts (AGEs). In the AGEs measurement instrument illustrated in FIG. 1, light is irradiated to the surface of a human body (arm) which is an object placed on the upper portion of the device, and an indicator relating to the AGEs such as AGEs amount is measured from the reflected light, As illustrated in FIG. 2, the AGEs measurement instrument has a light emitting diode (LED), and the arm is irradiated with irradiation light emitted from the LED (FIG. 1). For example, an LED emits light (also referred to as near-ultraviolet light or excitation light) in a near-ultraviolet wavelength band (for example, about 330 nm to about 420 nm, also called an excitation wavelength).

By this irradiation light (near-ultraviolet light), the AGEs existing in the arms emit fluorescence light. The wavelength of this fluorescence light is outside the near-ultraviolet wavelength band (for example, about 430 nm to about 560 nm). A photodetector (PD) of the AGE measurement instrument performs light measurement in the photometric range within the irradiation range where the arm irradiated with the irradiation light from the LED. At this time, a predetermined wavelength is measured by using a filter. That is, one PD of the AGEs measurement instrument measures the light in the near-ultraviolet wavelength band, and the other PD measures the light outside the near-ultraviolet wavelength band.

The AGEs measurement instrument obtains an indicator relating to the AGEs by using the results of the light measurement of each wavelength band by these PDs (photodetectors). Therefore, in this case, since the light measurement is performed by the PD, only the indicator as the point can be obtained. For this reason, in a case where measurement error factors such as stains exist at the measurement position (the portion that reflects light) of the object, sufficiently accurate measurement cannot be performed. In such a case, troublesome work such as shifting the measurement position and performing the measurement is required.

<Indicator Measurement of Region>

In view of this, irradiation light including a predetermined irradiation wavelength band is emitted, a first reflected light which is reflected light in the first wavelength band obtained from reflection of the emitted irradiation light on a predetermined object and a second reflected light which is reflected light in the second wavelength band obtained from reflection of the irradiation light on the object are received by a plurality of pixels, and a value of a predetermined indicator relating to a region within a predetermined range of the object is obtained on the basis of the respective received light amounts of the first reflected light and the second reflected light.

For example, the optical apparatus includes: a light emitting unit that emits irradiation light including a predetermined irradiation wavelength band; a light receiving unit that receives, at a plurality of pixels, first reflected light which is reflected light in a first wavelength band obtained from reflection of the irradiation light emitted by the light emitting unit on a predetermined object and second reflected light which is reflected light in a second wavelength band obtained from reflection of the irradiation light on the object; and an indicator processing unit that obtaining a value of a predetermined indicator relating to a region of a predetermined range of the object on the basis of the respective received light amounts of the first reflected light and the second reflected light received by the light receiving unit.

With such a configuration, it is possible to more easily obtain the indicator value relating to the AGEs.

2. First Embodiment

<Measurement Apparatus>

Figure 3:
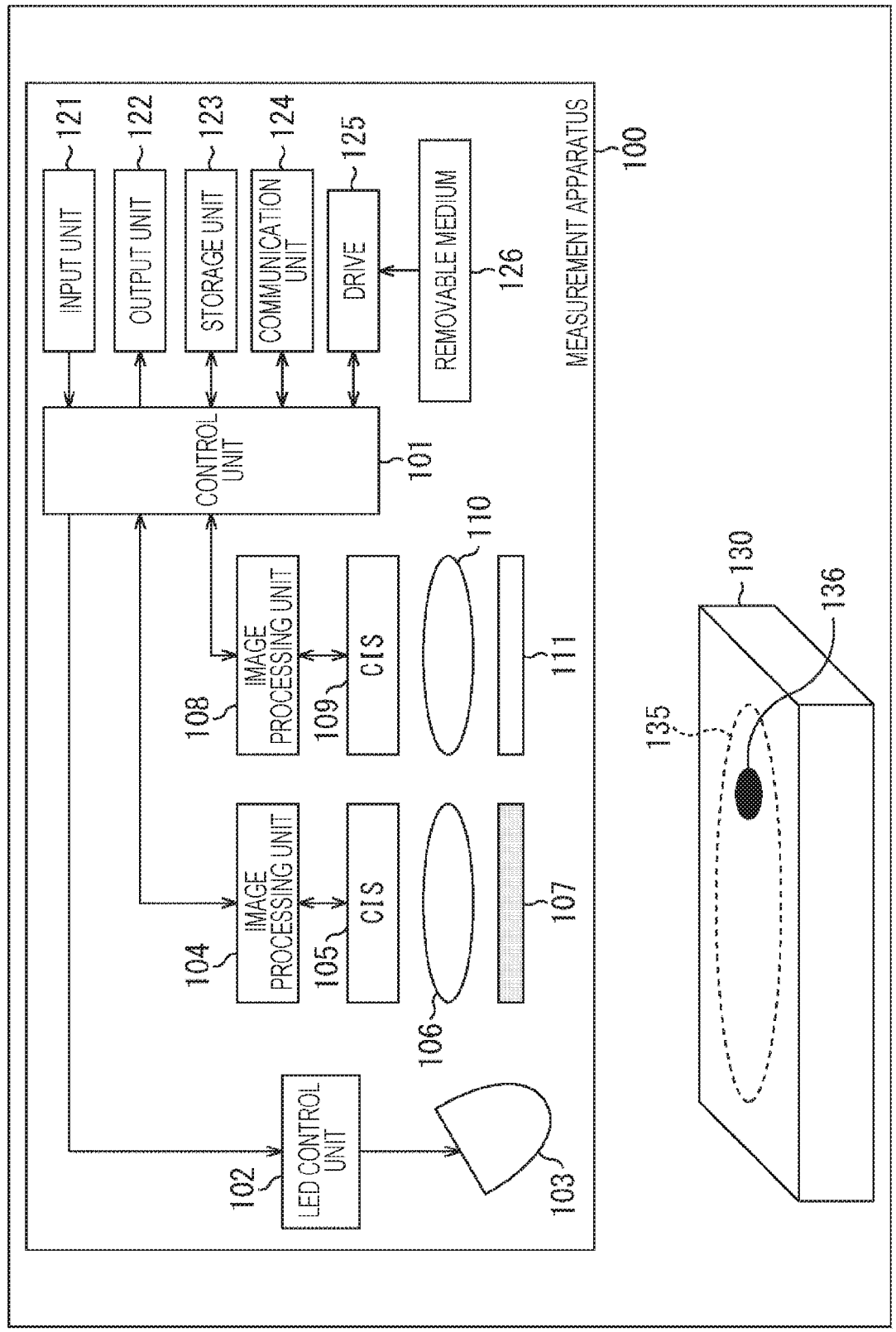
FIG. 3 is a block diagram illustrating a main configuration example of a measurement apparatus.

FIG. 3 is a block diagram illustrating a main configuration example of a measurement apparatus which is an embodiment of an optical apparatus to which the present technology is applied. The measurement apparatus 100 illustrated in FIG. 3 is an apparatus for using a portion of the human body 130 (the skin thereof) as the measurement target region 135, measuring light with respect to the measurement target region 135, and an indicator relating to advanced glycation endproducts (AGEs) included in the human body 130 (the measurement target region 135 thereof) on the basis of the result of the light measurement. As illustrated in FIG. 3, the measurement apparatus 100 includes a control unit 101, an LED control unit 102, an LED 103, an image processing unit 104, a complementary metal oxide semiconductor (CMOS) image sensor (CIS) 105, a lens 106, a filter 107, an image processing unit 108, a CIS 109, a lens 110, and a filter 111. Furthermore, the measurement apparatus 100 includes an input unit 121, an output unit 122, a storage unit 123, a communication unit 124, and a drive 125. A removable medium 126 can be attached to the drive 125.

The control unit 101 controls each processing unit of the measurement apparatus 100 and performs processes related to control in measurement. The LED control unit 102 controls light emission of the LED 103 under the control of the control unit 101. The LED 103 is an embodiment of a light emitting unit that emits irradiation light to irradiate an object, and is controlled by the LED control unit 102 to emit light having a near-ultraviolet wavelength band (for example, about 300 nm to about 420 nm) (near-ultraviolet light) and irradiates the human body 130 (a region including the measurement target region 135 thereof) with the irradiation light. The LED 103 is controlled by the LED control unit 102 and can emit light with arbitrary light intensity at arbitrary timing for an arbitrary time period. That is, the LED 103 can emit irradiation light having an arbitrary light amount.

A portion of the irradiation light causes excitation of predetermined substances such as AGEs contained in the skin of the human body 130. A predetermined substance such as AGEs emits fluorescence light when returning to the ground state by absorbing the energy of irradiation light (near-ultraviolet light). That is, the near-ultraviolet light contained in the irradiation light becomes excitation light, and thus, fluorescence light is emitted. The wavelength band of this emitted fluorescence light (also referred to as emitted light) is a wavelength band (for example, about 430 nm to about 600 nm) different from the near-ultraviolet wavelength band. That is, wavelength shift occurs.

The measurement apparatus 100 measures the light in the two wavelength bands to measure the indicators relating to the AGEs on the basis of the results of the light measurement in the two wavelength bands. That is, the measurement apparatus 100 receives the first reflected light, which is the reflected light in the first wavelength band obtained by reflection of the irradiation light on the human body 130 (the measurement target region 135 thereof) and the second reflected light, which is the reflected light in the second wavelength band, obtained by reflection of the irradiation light on the human body 130 (the measurement target region 135 thereof) and measures the indicators relating to the AGEs on the basis of the respective received light amounts. The image processing unit 104 to the filter 107 are configured to measure the first wavelength band. The image processing unit 108 to the filter 111 are configured to measure light in the second wavelength band.

The filter 107 is an embodiment of an optical filter that transmits the first reflected light and transmits light in the near-ultraviolet to blue wavelength band (near-ultraviolet light or blue light). The configuration of the filter 107 is arbitrary and may be configured with a plurality of optical filters. The lens 106 is an embodiment of an optical system that exerts an optical influence on the first reflected light transmitted through the filter 107 and is configured with an optical lens to collect light transmitted through the filter 107 in the pixel region of the CIS 105. In addition, the configuration of the lens 106 is arbitrary and may be configured with a plurality of optical members. For example, the lens 106 may include a plurality of optical lenses. Furthermore, for example, the lens 106 may include an optical member other than an optical lens such as a diaphragm.

The CIS 105 is one embodiment of a light receiving unit that receives a first reflected light to generate a first reflection image and has a pixel region in which a plurality of pixels is arranged and photoelectrically converts the light incident on each pixel to generate an image data. In the pixel region of the CIS 105, light transmitted through the filter 107 and the lens 106 is incident. The CIS 105 measures light measurement with respect to the measurement target region 135 in the near-ultraviolet to blue wavelength band. The CIS 105 generates an image data by using the result of light measurement of each pixel. That is, the CIS 105 captures an image of the measurement target region 135 of the human body 130 and generates an image data of captured images in the near-ultraviolet to blue wavelength bands. The captured image in the near-ultraviolet to blue wavelength band is also referred to as a UV reflection image or an excitation light image. The CIS 105 supplies the image data of the obtained UV reflection image to the image processing unit 104.

The image processing unit 104 performs arbitrary image processing on the image data and supplies the image data (image data of the UV reflection image) subjected to the image processing to the control unit 101.

The filter 111 is an embodiment of an optical filter that transmits the second reflected light, and transmits light in the blue or red wavelength band (light in a wavelength band other than near-ultraviolet to blue). The configuration of the filter 111 is arbitrary and may be configured with a plurality of optical filters. The lens 110 is an embodiment of an optical system that exerts an optical influence on the second reflected light transmitted through the filter 111 and is configured with an optical lens to collect the light transmitted through the filter 111 in the pixel region of the CIS 109. In addition, the configuration of the lens 110 is arbitrary and may be configured with a plurality of optical members. For example, the lens 110 may include a plurality of optical lenses. Furthermore, for example, the lens 110 may include an optical member other than an optical lens such as a diaphragm.

The CIS 109 is an embodiment of a light receiving unit that receives a second reflected light to generate a second reflection image and has a pixel region in which a plurality of pixels is arranged and photoelectrically converts the light incident on each pixel to generate an image data. In the pixel region of the CIS 109, light transmitted through the filter 111 and the lens 110 is incident. The CIS 109 measures the measurement target region 135 in the blue to red wavelength band. The CIS 105 generates an image data by using the result of light measurement of each pixel. That is, the CIS 109 captures an image of the measurement target region 135 of the human body 130, and generates an image data of a captured image in the blue to red wavelength band. The captured image in the blue to red wavelength bands is also referred to as a fluorescence image or a radiation image. The CIS 109 supplies the image data of the obtained fluorescence image to the image processing unit 108.

The image processing unit 108 performs arbitrary image processing on the image data and supplies the image data (image data of the fluorescence image) subjected to the image processing to the control unit 101.

As described above, in the measurement apparatus 100, the CIS 105 and the CIS 109 are used as the light receiving units, so that the it is possible to perform light measurement on the measurement target region 135 of the skin of the human body 130 with respect to two wavelength bands (near-ultraviolet to blue and blue to red). Since the CIS 105 and the CIS 106 are multipixels, the measurement apparatus 100 can obtain the distribution of the results of light measurement (a plurality of results of light measurement) in the measurement target region 135. Therefore, for example, even in a case where an error factor such as a stain 136 exists in the measurement target region 135, the measurement apparatus 100 suppresses the influence of the error factor by using, for example, the results of light measurement with respect to the other portions, so that it is possible to correctly obtain the indicator relating to the AGEs. Therefore, a complicated work such as shifting the measurement position can be suppressed, and a desired indicator value can be more easily obtained.

The input unit 121 performs processing related to the input of information (programs, data, and the like), instructions, and the like. For example, the input unit 121 may have an arbitrary input device such as a jog dial (trademark), a key, a button, or a touch panel, and an operation input to the input device by a user or the like may be received and a signal (user instruction) corresponding to the operation input may be supplied to the control unit 101. Furthermore, for example, the input unit 121 may have an external input terminal, and information supplied from the outside of the measurement apparatus 100 (another apparatus or the like connected through the external input terminal may be supplied to the control unit 101. Furthermore, for example, the input unit 121 may have an input device such as a camera or a microphone, so that a user's gesture, voice, and the like may be received as a user instruction and these user instructions may be supplied to the control unit 101.

The output unit 122 performs processing related to the output of information (programs, data, and the like) and the like. For example, the output unit 122 may have a monitor for displaying an image, and the information supplied from the control unit 101 may be displayed on the monitor as an image. Furthermore, for example, the output unit 122 may have a speaker that outputs sound, and the information supplied from the control unit 101 may be output from the speaker as sound. Furthermore, for example, the output unit 122 may have an external output terminal, and arbitrary information (programs, data, and the like) supplied from the control unit 101 may be supplied to the outside of the measurement apparatus 100 (another apparatus or the like connected through the external output terminal).

The storage unit 123 performs processing related to storage of information. For example, the storage unit 123 may have an arbitrary storage medium such as a flash memory, a solid state drive (SSD), or a hard disk, and arbitrary information (programs, data, and the like) supplied from the control unit 101 is stored in the storage medium. Furthermore, for example, the storage unit 123 may read the information stored in the storage medium and supply the information to the control unit 101.

The communication unit 124 performs processing related to communication. For example, the communication unit 124 may have a communication interface in accordance with an arbitrary standard such as a wired local area network (LAN), a wireless LAN, Bluetooth (registered trademark), near field communication (NFC), infrared communication, high-definition multimedia interface (HDMI (registered trademark)), or universal serial bus (USB), may communicate with other devices via the communication interface to supply the arbitrary information (programs, data, and the like) supplied from the control unit 101 to other devices or may acquire arbitrary information (programs, data, and the like) from another devices to supply the arbitrary information to the control unit 101.

The drive 125 performs processing related to the removable medium 126 attached to the drive 125 itself. The removable medium 126 is a medium that is removable from the drive 125, which is configured with any storage medium such as a magnetic disk, an optical disk, a magneto-optical disk, or a semiconductor memory. The drive 125 drives the removable medium 126 attached to the drive and reads and writes information from and to the removable medium 126. For example, the drive 125 may drive the removable medium 126 attached to the drive, as necessary, to readout arbitrary information (programs, data, and the like) written in the removable medium 126 and supply the information to the control unit 101. Furthermore, the drive 125 may write arbitrary information supplied from the control unit 101 in the removable medium 126.

<Control Unit>

Figure 4:
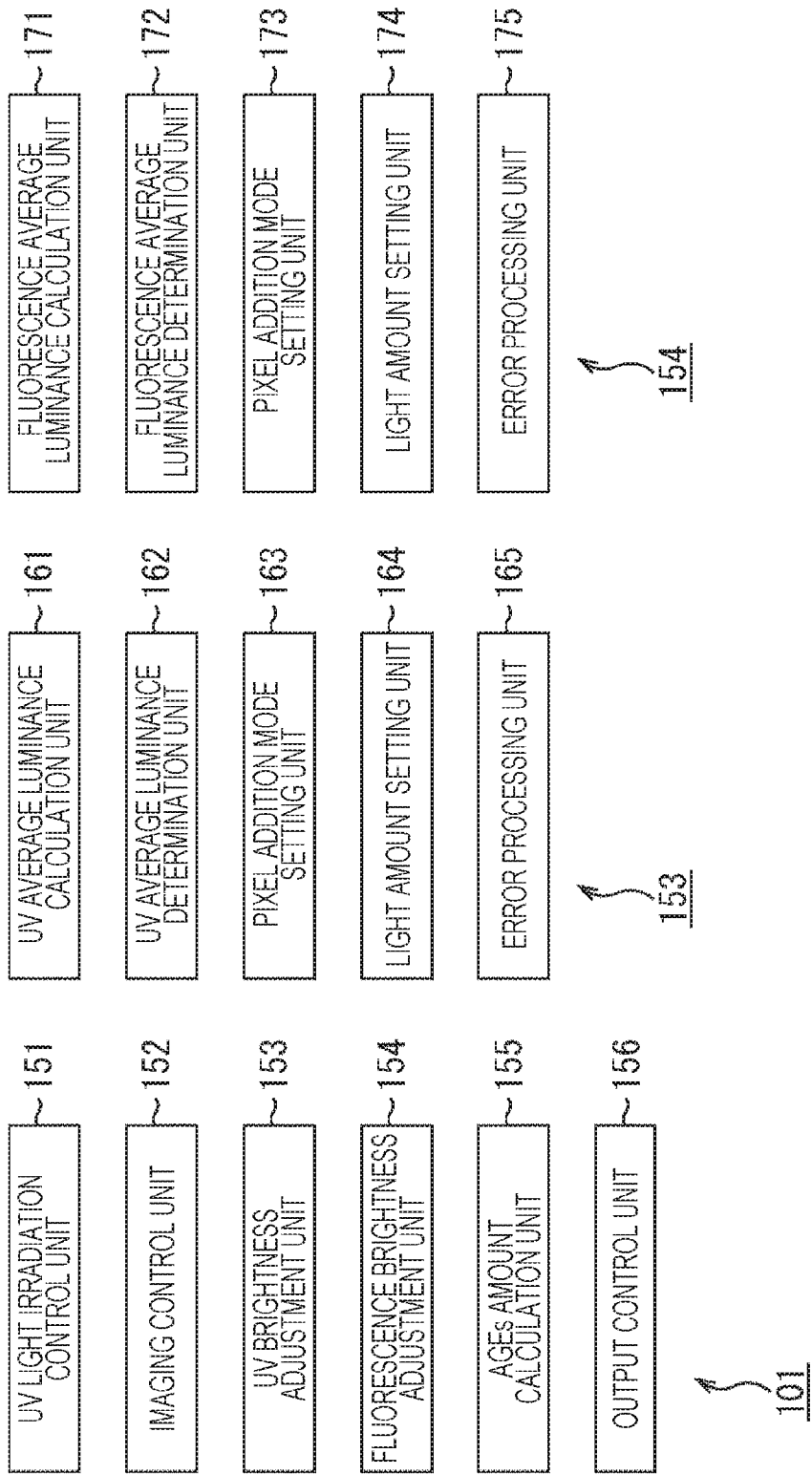
FIGS. 4A, 4B, and 4C are functional block diagrams illustrating functions realized by the control unit.

FIGS. 4A, 4B, and 4C are functional block diagrams illustrating an example of main functions realized by the control unit 101 executing programs and the like. As illustrated in FIG. 4A, by executing a program, the control unit 101 can have functions of, for example, a UV light irradiation control unit 151, an imaging control unit 152, a UV brightness adjustment unit 153, a fluorescence brightness adjustment unit 154, an AGEs amount calculation unit 155, and an output control unit 156. The UV light irradiation control unit 151 performs control relating to the emission of the irradiation light. The imaging control unit 152 performs processing related to the imaging. The UV brightness adjustment unit 153 performs processing related to the brightness adjustment of the UV reflection image obtained by imaging. The fluorescence brightness adjustment unit 154 performs processing related to the brightness adjustment of the fluorescence image obtained by imaging. The AGEs amount calculation unit 155 performs processing related to the calculation of the AGEs amount. The output control unit 156 performs control relating to output of information associated with the AGEs amount.

As described above, the measurement apparatus 100 irradiates the human body 130 with the irradiation light from the LED 103, receives the reflected light by the CIS 105 and the CIS 109, and obtains the image data of the UV reflection image and the fluorescence image. The control unit 101 calculates the AGEs amount that numerically represents the AGEs amount as an indicator relating to advanced glycation endproducts (AGEs) on the basis of the image data.

At this time, the control unit 101 may adjust the brightness of at least one of the UV reflection image or the fluorescence image so that the AGEs amount can be obtained more accurately. For example, the UV brightness adjustment unit 153 may adjust the brightness of the UV reflection image. Furthermore, for example, the fluorescence brightness adjustment unit 154 may adjust the brightness of the fluorescence image. Furthermore, for example, the UV brightness adjustment unit 153 may adjust the brightness of the UV reflection image, and the fluorescence brightness adjustment unit 154 may adjust the brightness of the fluorescence image.

In this brightness adjustment, for example, the UV brightness adjustment unit 153 may adjust the brightness of the UV reflection image by using the average luminance of the UV reflection image. Furthermore, for example, the fluorescence brightness adjustment unit 154 may adjust the brightness of the fluorescence image by using the average luminance of the fluorescence image.

The brightness adjustment may be performed, for example, by pixel addition. For example, in a case where the brightness (for example, the average luminance) of the UV reflection image is insufficient, the UV brightness adjustment unit 153 may add the surrounding pixel values to each pixel value of the UV reflection image. By applying such a pixel addition mode, each pixel value of the UV reflection image can be increased, and thus, the average luminance can be increased. Furthermore, in a case where the brightness of the UV reflection image is insufficient even if the pixel addition mode is applied, the UV brightness adjustment unit 153 may increase the number of surrounding pixels to which the pixel values are added. By increasing the number of pixels to which the pixel values are added with respect to each pixel, each pixel value of the UV reflection image can be further increased, and thus, the average luminance can be further increased.

Similarly, for example, in a case where the brightness (for example, the average luminance) of the fluorescence image is insufficient, the fluorescence brightness adjustment unit 154 may apply the pixel addition mode. Then, in a case where the brightness of the fluorescence image is still insufficient, the fluorescence brightness adjustment unit 154 may further increase the number of surrounding pixels to which the pixel values are added.

In addition, as the number of pixels to which the pixel values are added is increased, the range of pixels influencing each other is increased, so that the difference between the pixel values of the UV reflection image and the fluorescence image before and after the pixel addition is increased (deterioration of the UV reflection image and the fluorescence image is increased). For this reason, there is a possibility that calculation of the accurate AGEs amount becomes more difficult. For this reason, an upper limit may be set for the number of surrounding pixels to which pixel values are to be added, so that deterioration of the UV reflection image or fluorescence image due to the pixel addition may not be increased more than a certain amount.

In addition, a method of adjusting the brightness is arbitrary, and the method may be other than such a pixel addition mode. For example, if the light amount of the irradiation light is increased or decreases, the light amount of the reflected light also naturally is increased and decreases. Therefore, for example, the UV brightness adjustment unit 153 or the fluorescence brightness adjustment unit 154 may adjust the light amount of the irradiation light, so that the brightness of the UV reflection image or the fluorescence image is adjusted. In addition, a method of controlling the light amount is arbitrary. For example, the light amount may be increased or decreased by increasing or decreasing the irradiation time of the irradiation light. Furthermore, for example, the light amount may be increased or decreased by increasing or decreasing the light intensity of the irradiation light.

In addition, in order to suppress the influence on the human body 130 and the occurrence of failure of the measurement apparatus 100 (that is, in order to improve the safety and reliability of the measurement apparatus 100), an upper limit may be set to the light amount of the irradiation light.

In addition, the method using the pixel addition mode described above and the method using the light amount control of the irradiation light may be combined. For example, first, the brightness adjustment may be performed by the method using the pixel addition mode, and in a case where the brightness is still insufficient even though the upper limit of the number of pixels to be added is reached, the light amount of the irradiation light may be increased. Of course, conversely, in a case where the light amount of the irradiation light is first increased and the brightness is still insufficient even though the upper limit of the light amount is reached, the brightness adjustment may be performed by applying the pixel addition mode.

<UV Brightness Adjustment Unit>

FIG. 4B is a functional block diagram illustrating an example of main functions of the UV brightness adjustment unit 153. As illustrated in FIG. 4B, the UV brightness adjustment unit 153 may have functions of, for example, a UV average luminance calculation unit 161, a UV average luminance determination unit 162, a pixel addition mode setting unit 163, a light amount setting unit 164, and an error processing unit 165. The UV average luminance calculation unit 161 performs processing related to the calculation of the average luminance of the UV reflection image. The UV average luminance determination unit 162 performs processing related to the determination on the average luminance of the UV reflection image. The pixel addition mode setting unit 163 performs processing related to the setting of the pixel addition mode of the UV reflection image. The light amount setting unit 164 performs processing related to the setting of the light amount of the irradiation light. The error processing unit 165 performs processing related to error processing.

<Fluorescence Brightness Adjustment Unit>

FIG. 4C is a functional block diagram illustrating an example of main functions of the fluorescence brightness adjustment unit 154. As illustrated in FIG. 4C, the fluorescence brightness adjustment unit 154 may have functions of, for example, a fluorescence average luminance calculation unit 171, a fluorescence average luminance determination unit 172, a pixel addition mode setting unit 173, a light amount setting unit 174, and an error processing unit 175. The fluorescence average luminance calculation unit 171 performs processing related to the calculation of the average luminance of the fluorescence image. The fluorescence average luminance determination unit 172 performs processing related to determination on the average luminance of the fluorescence image. The pixel addition mode setting unit 173 performs processing related to the setting of the pixel addition mode of the fluorescence image. The light amount setting unit 174 performs processing related to the setting of the light amount of the irradiation light. The error processing unit 175 performs processing related to error processing.

<Flow of AGEs Amount Calculation Process>

Next, an example of a flow of various processes executed by the measurement apparatus 100 will be described. First, an example of a flow of the AGEs amount calculation process executed by the control unit 101 will be described with reference to a flowchart of FIG. 5.

If the AGEs amount calculation process is started, the UV light irradiation control unit 151 controls the LED 103 through the LED control unit 102 in step S101 to irradiate the human body 130 (the skin thereof) located at a predetermined position with respect to the measurement apparatus 100 with the near-ultraviolet light. In step S102, the imaging control unit 152 controls the CIS 105 and the CIS 109 to image the measurement target region 135 of the human body 130 (the skin thereof). That is, the imaging control unit 152 causes the CIS 105 to generate an image data of the UV reflection image. In addition, the imaging control unit 152 causes the CIS 109 to generate an image data of the fluorescence image.

In step S103, the UV brightness adjustment unit 153 adjusts the brightness of the UV reflection image. In step S104, the fluorescence brightness adjustment unit 154 adjusts the brightness of the fluorescence image. Details of these processes will be described later.

In step S105, the AGEs amount calculation unit 155 calculates the AGEs amount by using the image data of the UV reflection image or the fluorescence image. A method of calculating the AGEs amount will be described later.

In step S106, the output control unit 156 causes the AGEs amount calculated in step S105 to be output. The output of the AGEs amount will be described later.

Upon completion of the process of step S106, the AGEs amount calculation process is ended.

<Flow of UV Reflection Image Brightness Adjustment Process>

Next, an example of a flow of the UV reflection image brightness adjustment process executed in step S103 of FIG. 5 will be described with reference to a flowchart of FIG. 6.

If the UV reflection image brightness adjustment process is started, in step S111, the UV average luminance calculation unit 161 calculates the average luminance of the UV reflection image (the average of the pixel values of the respective pixels). In addition, in the following description, the average luminance of the UV reflection image is also referred to as "$I_{UV}$ with overline". As illustrated in step S111 of FIG. 6, the "$I_{UV}$ with overline" illustrates that the overline ($^-$) is attached to the $I_{UV}$.

In step S112, the UV average luminance determination unit 162 determines whether or not the average luminance ($I_{UV}$ with overline) calculated in step S111 is larger than a predetermined threshold value $Th_{UV}$. In a case where it is determined that the average luminance ($I_{UV}$ with overline) is larger than the predetermined threshold value $Th_{UV}$, that is, in a case where it is determined the UV reflection image is sufficiently bright, the UV reflection image brightness adjustment process is ended, and the process returns to FIG. 5 and proceeds to step S104 (Return 1).

In addition, in a case where it is determined in step S112 that the average luminance ($I_{UV}$ with overline) is equal to or smaller than the predetermined threshold value $Th_{UV}$, that is, in a case where it is determined that the brightness of the UV reflection image is not sufficient, the process proceeds to step S113.

In step S113, the pixel addition mode setting unit 163 determines whether or not the pixel addition mode can be set. In a case where it is determined that the pixel addition mode has not yet been set or in a case where it is determined that the pixel addition mode is set but the number of pixels to which the pixel values are added has not reached the upper limit (the number of pixels can be still extended), the process proceeds to step S114.

In step S114, the pixel addition mode setting unit 163 sets the pixel addition mode in which the pixel value of the surrounding pixels is added to the pixel value of each pixel of the UV reflection image. In addition, in a case where the pixel addition mode has already been set, the pixel addition mode setting unit 163 increases the number of pixels to be added. Upon completion of the process of step S114, the UV reflection image brightness adjustment process is ended, the process returns to FIG. 5 and returns to step S101, and the subsequent processes are repeated (Return 2). That is, irradiation light irradiation and imaging are performed with new settings, and the UV reflection image brightness adjustment process is performed again.

In addition, in step S113, in a case where it is determined that the pixel addition mode cannot be set, or in a case where it is determined that the pixel addition mode has already been set and the number of pixels to which the pixel values are added has reached the upper limit (the number of pixels cannot be further extended) the process proceeds to step S115.

In step S115, the light amount setting unit 164 updates the light amount t of the irradiation light emitted by the LED 103. That is, the light amount setting unit 164 controls, for example, the LED control unit 102 to increase the light intensity of the irradiation light or increase the irradiation time to increase the light amount t of the irradiation light.

In step S116, the light amount setting unit 164 determines whether or not the updated light amount t is smaller than a predetermined threshold value $t_{Th}$. The predetermined threshold value $t_{Th}$ denotes the upper limit of the light amount t. That is, in a case where it is determined that the light amount t is smaller than the threshold value $t_{Th}$, that is, in a case where it is determined the light amount t has not reached the upper limit, the UV reflection image brightness adjustment process is ended, the process returns to FIG. 5 and returns to step S101, and the subsequent processes are repeated (Return 2). That is, the irradiation light irradiation and the imaging are performed with new settings, and the UV reflection image brightness adjustment process is performed again.

In addition, in a case where it is determined in step S116 that the light amount t is equal to or larger than the threshold value $t_{Th}$, that is, in a case where it is determined the light amount t has reached the upper limit, the process proceeds to step S117.

In step S117, the error processing unit 165 performs predetermined error processing. In this case, since it is not possible to make the UV reflection image bright any more, the error processing unit 165 performs error processing such as, for example, notifying the user to the message. The content of this error processing is arbitrary. Upon completion of the error processing, the UV reflection image brightness adjustment process is ended, the process returns to FIG. 5, and furthermore, the AGEs amount calculation process is ended (Return 3).

<Flow of Fluorescence Image Brightness Adjustment Process>

Next, an example of a flow of the fluorescence image brightness adjustment process executed in step S104 of FIG. 5 will be described with reference to a flowchart of FIG. 7. The fluorescence image brightness adjustment process is executed basically in a similar manner as the UV reflection image brightness adjustment process in FIG. 6.

That is, if the fluorescence image brightness adjustment process is started, in step S121, the fluorescence average luminance calculation unit 171 calculates the average luminance of the fluorescence image (the average of the pixel values of the respective pixels). In addition, in the following description, the average luminance of this fluorescence image is also referred to as "$I_{FL}$ with overline". This "$I_{FL}$ with overline" represents that the overline ($^-$) is attached to $I_{FL}$ as illustrated in step S121 of FIG. 7.

In step S122, the fluorescence average luminance determination unit 172 determines whether or not the average luminance ($I_{FL}$ with overline) calculated in step S121 is larger than a predetermined threshold value $Th_{FL}$. In a case where it is determined that the average luminance ($I_{FL}$ with overline) is larger than the predetermined threshold value $Th_{FL}$, that is, in a case where it is determined the fluorescence image is sufficiently bright, the fluorescence image brightness adjustment process is ended, and the process returns to FIG. 5 and proceeds to step S105 (Return 1).

In addition, in a case where it is determined in step S122 that the average luminance ($I_{FL}$ with overline) is equal to or smaller than the predetermined threshold value $Th_{FL}$, that is, in a case where it is determined that the brightness of the fluorescence image is not sufficient, the process proceeds to step S123.

In step S123, the pixel addition mode setting unit 173 determines whether or not the pixel addition mode can be set. In a case where it is determined that the pixel addition mode has not yet been set or in a case where it is determined that the pixel addition mode is set but the number of pixels to which the pixel values are added has not reached the upper limit (the number of pixels can be still extended), the process proceeds to step S124.

In step S124, the pixel addition mode setting unit 173 sets the pixel addition mode in which the pixel value of the surrounding pixels is added to the pixel value of each pixel of the fluorescence image. In addition, in a case where the pixel addition mode has already been set, the pixel addition mode setting unit 173 increases the number of pixels to be added. Upon completion of the processing in step S124, the fluorescence image brightness adjustment process is ended, the process returns to FIG. 5 and returns to step S101, and the subsequent processes are repeated (Return 2). That is, the irradiation light irradiation and the imaging are performed with new settings, and the UV reflection image brightness adjustment process and the fluorescence image brightness adjustment process are performed again.

In addition, in step S123, in a case where it is determined that the pixel addition mode cannot be set, or in a case where it is determined that the pixel addition mode has already been set and the number of pixels to which the pixel values are added has reached the upper limit (the number of pixels cannot be further extended) the process proceeds to step S125.

In step S125, the light amount setting unit 174 updates the light amount t of the irradiation light emitted by the LED 103. That is, the light amount setting unit 174 controls, for example, the LED control unit 102 to increase the light intensity of the irradiation light or increase the irradiation time to increase the light amount t of the irradiation light.

In step S126, the light amount setting unit 174 determines whether or not the updated light amount t is smaller than a predetermined threshold value $t_{Th}$. In a case where it is determined that the light amount t is smaller than the threshold value $t_{Th}$, that is, in a case where it is determined the light amount t has not reached the upper limit, the fluorescence image brightness adjustment process is ended, and the process returns to FIG. 5 and returns to step S101, and the subsequent processes are repeated (Return 2). That is, the irradiation of irradiation light and the imaging are performed with new settings, and the UV reflection image brightness adjustment process and the fluorescence image brightness adjustment process are performed again.

In addition, in a case where it is determined in step S126 that the light amount t is equal to or larger than the threshold value $t_{Th}$, that is, in a case where it is determined the light amount t has reached the upper limit, the process proceeds to step S127.

In step S127, the error processing unit 175 performs predetermined error processing. In this case, since the fluorescence image cannot be brightened any more, the error processing unit 175 performs error processing such as, for example, notifying the user to the message. The content of the error processing is arbitrary. Upon completion of the error processing, the fluorescence image brightness adjustment process is ended, the process returns to FIG. 5, and the AGEs amount calculation process is further completed (Return 3).

<SAF>

Figure 5:
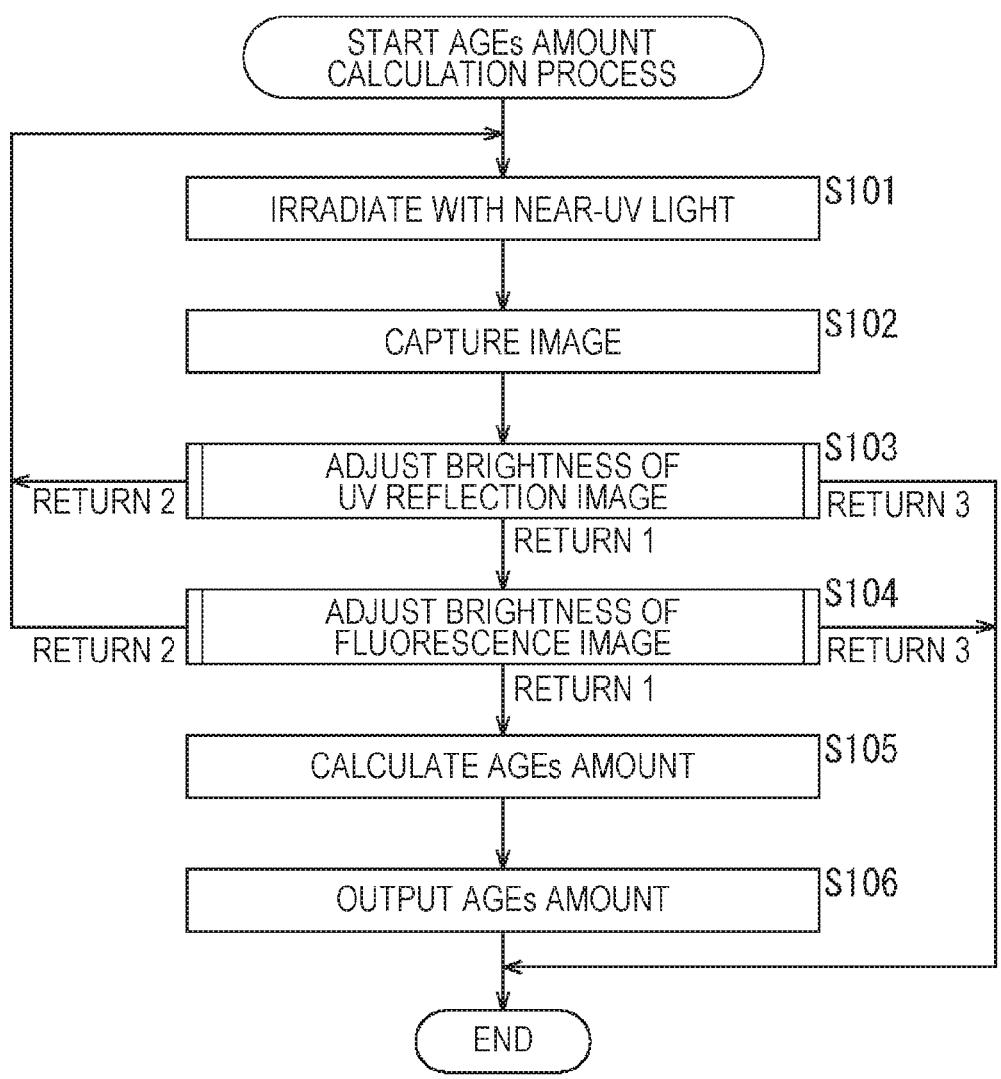
FIG. 5 is a flowchart illustrating an example of a flow of an AGEs amount calculation process.

By using the UV reflection image or the fluorescence image of which brightness has been adjusted as described above, the AGEs amount calculation unit 155 calculates the AGEs amount (step S105 in FIG. 5). The AGEs amount calculation unit 155 calculates skin autofluorescence (SAF) (also referred to as an AF value) as an indicator indicating the AGEs amount. The SAF is obtained, for example, by the following Formula (1).

[Mathematical Formula 1]

$$AF_E(\lambda_{exc}, S) = 100 \frac{\langle I_{em}\rangle(\lambda_{exc}, S)}{\langle I_{exc}\rangle(\lambda_{exc}, S)} \qquad (1)$$

In Formula (1), $AF_E$ ($\lambda_{exc}$, s) represents an AF value measured by an excitation emission matrix scanner (EEMS) (a spectrometer with 1 nm resolution) when the subject s is irradiated with the excitation light wavelength $\lambda_{exc}$. In addition, $\langle I_{em}\rangle$ ($\lambda_{exc}$, s) represents a light intensity in the wavelength range of 420 nm to 600 nm measured when the subject s is irradiated with the excitation light wavelength $\lambda_{exc}$. In addition, $\langle I_{exc}\rangle$ ($\lambda_{exc}$, represents a light intensity in the wavelengths range of 300 nm to 420 nm measured when the subject s is irradiated with the excitation light wavelength $\lambda_{exc}$. For example, in the graph 180 illustrating the relationship between the wavelength and the light intensity of the reflected light detected in the light receiving unit (CIS 105 and CIS 109) in FIG. 8, the light intensity $\langle I_{exc}\rangle$ ($\lambda_{exc}$, s) represents the area of the portion (indicated by dark gray) of the wavelength region shorter than the wavelength 420 indicated by the straight line 181, and The light intensity $\langle I_{em}\rangle$ ($\lambda_{exc}$, s) represents the area of the portion (indicated by dark gray) of the wavelength region longer than the wavelength 420 indicated by the straight line 181.

For example, the light intensity $\langle I_{em}\rangle$ ($\lambda_{exc}$, s) can be obtained from the UV reflection image obtained in the CIS 105. In addition, the light intensity $\langle I_{exc}\rangle$ ($\lambda_{exc}$, s) can be obtained from the fluorescence image obtained in the CIS 109. That is, the AGEs amount calculation unit 155 calculates the AF value $AF_E$ ($\lambda_{exc}$, s) by using the image data of the UV reflection image and the fluorescence image. In particular, the amount of reflection of the fluorescence light is often small, and thus, there is a high possibility that the brightness of the fluorescence image is insufficient. If the brightness of the UV reflection image or the fluorescence image is insufficient, the above-mentioned light intensity values tend to be inaccurate, and thus, there is a high possibility that it becomes difficult to obtain a sufficiently accurate AF value. Therefore, by adjusting the brightness of the UV reflection image and the fluorescence image as described above, the AGEs amount calculation unit 155 can more accurately obtain the AF value.

<Output>

The output control unit 156 causes, for example, the output unit 122 to output the AGEs amount (for example, SAF) calculated as described above. For example, the output control unit 156 displays the AGEs amount on a monitor (a display device) included in the output unit 122. In this case, for example, the AGEs amount calculation unit 155 obtains the AF value for each pixel (or each partial region), and the output control unit 156 may express the AF value of each pixel (or each partial region) by color or density and display the AF values on the monitor of the output unit 122 as an image. That is, in this case, the distribution of AF values is displayed as an image.

Figure 9:
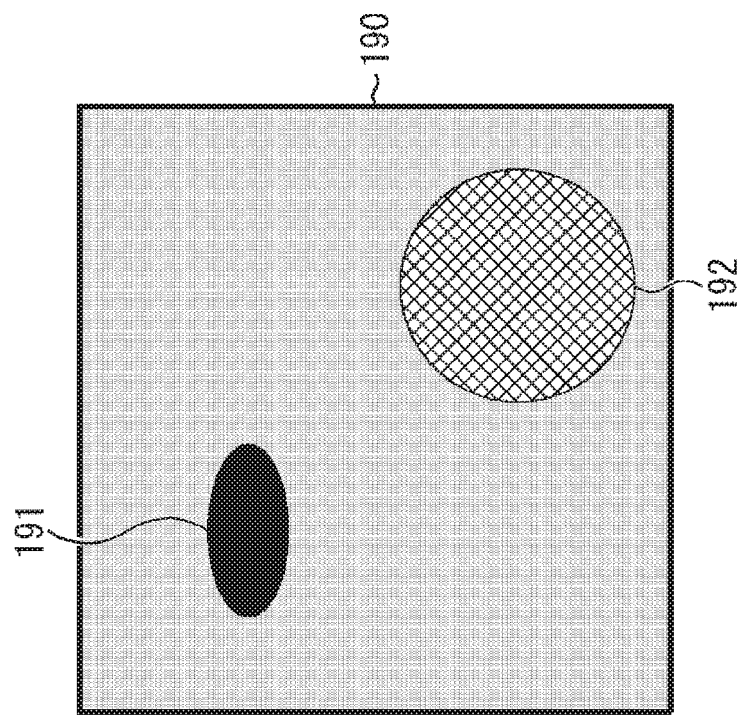
FIG. 9 is a diagram illustrating an example of an image of a measurement result.

The image 190 illustrated in FIG. 9 is an example of an image illustrating the distribution of AF values. That is, the distribution of the AF values in the measurement target region 135 (the image 190 is the region of (the skin of) the human body 130 corresponding to the viewing angle of the CIS 105 and the CIS 109) appears in the measurement target region 135. For example, in the case of obtaining the AF value by receiving reflected light with one PD as in the case of the related art, there is a possibility that the obtained AF value is a singular point of the skin, and in order to obtain a more accurate AGEs amount, a complicated work such as measuring at plural places is required. On the other hand, in the measurement apparatus 100, since the reflected light is received by the CIS, it is possible to perform light measurement on the measurement target region 135 (surface) at a time, and it is possible to obtain the distribution of the AF value in that region. For this reason, it is possible to obtain the AGEs amount in a wider range, and it is possible to suppress the influence of the singular point of the skin. That is, more accurate AGEs amount can be more easily obtained.

However, if all the obtained AF values of each pixel (or each partial region) are represented by numerical values, there is a possibility that it will become difficult for the user to view. In addition, there is a possibility that it is difficult for a general user who does not have expert knowledge to intuitively grasp what meaning the values have (for example, whether the AGEs amount is large or small) even if the user views the AF values as numerical values. Therefore, the output control unit 156 causes the image 190 as illustrated in FIG. 9 to be displayed on the monitor, and thus, the user can easily (intuitively) grasp the state of the distribution of the AF values (that is, AGEs) in the measurement target region 135 from color, concentration, or the like.

In addition to this image 190, statistical values (an average value, a total value, and the like) of the AF values of the entire measurement target region 135 may be displayed. If this image 190 is displayed with a graphical user interface (GUI), for example, if the user specifies a position in this image 190, the AF value (numerical value) of the position (a pixel or a partial region thereof) may be allowed to be displayed. Furthermore, for example, if the user specifies a partial region in the image 190, the statistical value of the AF value in the partial region may be allowed to be displayed.

In addition, in general, in some cases, the melanin pigment may be deposited on the skin (human body 130) or the redness may be generated, and thus, there is a possibility that such a portion may be included in the measurement target region 135. For example, in the image 190, the melanin 191 indicates a portion in which the melanin pigment is deposited on the skin (human body 130), and the redness 192 indicates a portion of the redness which is generated in the skin (human body 130). It is difficult to obtain an accurate AGEs amount in such a portion (a singular point of the skin) of the melanin 191, the redness 192, and the like. For this reason, there is a possibility that the AF value of such a part is different from that of the surroundings. That is, in the image 190, there is a high possibility that the melanin 191 and the redness 192 distinguishably occur as color or density. Therefore, in the image 190, the user can more easily (intuitively) distinguish a portion where the melanin pigment in the measurement target region 135 is not deposited or the redness is not generated.

Therefore, for example, in the case of displaying the AF value or the statistical value thereof at a desired position in the image 190, the user can specify the position where a correct AF value is obtained while more easily avoiding the singular points such as melanin 191 and redness 192 of the skin. Furthermore, in the case of calculating the statistical value of the AF value, the measurement apparatus 100 can obtain the statistical value excluding such singular points of the skin.

In other words, in the image 190, the user can easily grasp the state of distribution (number, shape, size, color, and the like) of the singular points of the skin such as the melanin 191 and the redness 192.

In addition, instead of the image 190, the output control unit 156 may cause the AF value and the statistical values (for example, an average value, a total value, and the like) of each pixel (each partial region) to be displayed on the monitor of the output unit 122 or to be output from the speaker included in the output unit 122 as sound or the like.

In addition, the output control unit 156 may cause the AF value or a predetermined indicator calculated by using the AF value to be supplied as data to another apparatus through an external terminal included in the output unit 122. Furthermore, the output control unit 156 may cause the AF value or a predetermined indicator calculated by using the AF value to be supplied as data to another apparatus through the communication unit 124. Furthermore, the output control unit 156 may cause the AF value or a predetermined indicator calculated by using the AF value to be stored as data in the storage unit 123 or may cause the AF value or the predetermined indicator to be written in the removable medium 126 through the drive 125.

<Omission of Method of Controlling Light Amount of Irradiation Light>

In addition, the above description, an example in which the method of using the pixel addition mode and the method of controlling the light amount of the irradiation light are combined at the time of brightness adjustment has been described, but the method of controlling the light amount of the irradiation light may be omitted.

Figure 10:
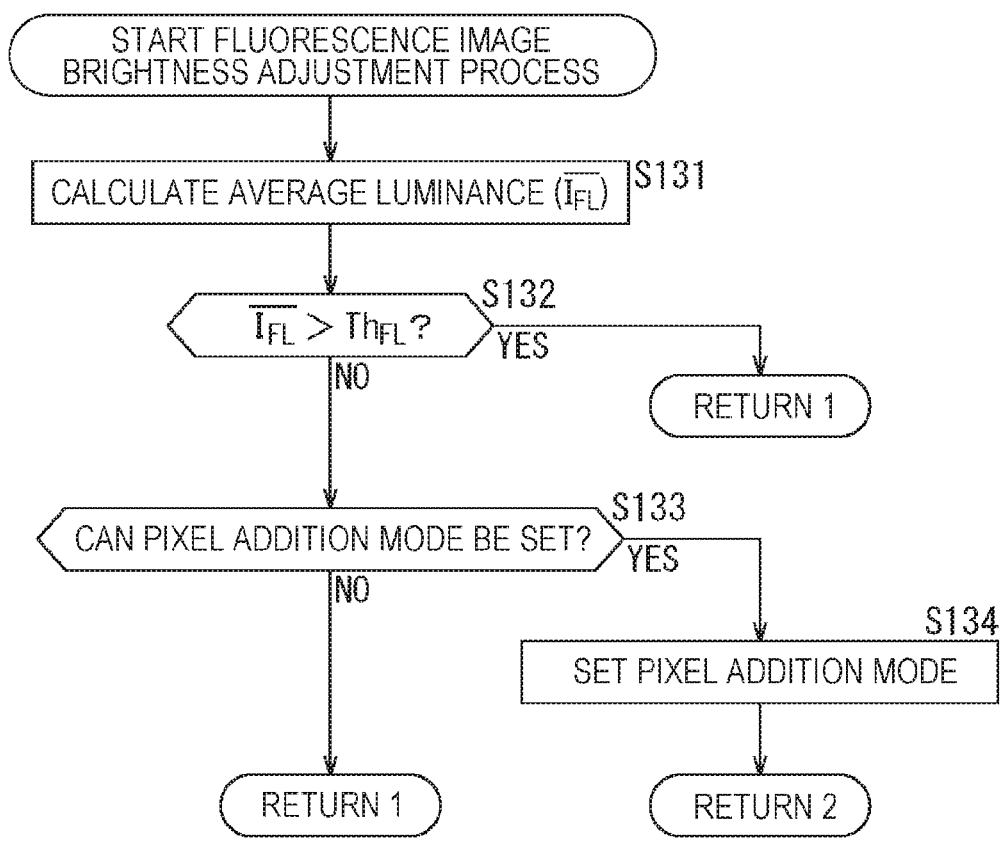
FIG. 10 is a flowchart illustrating an example of a flow of a fluorescence image brightness adjustment process.

An example of a flow of the fluorescence image brightness adjustment process in this case will be described with reference to a flowchart of FIG. 10. In this case, the fluorescence brightness adjustment unit 154 performs the processes of steps S131 to S134 basically in a manner similar to those of the processes of steps S121 to S124 in FIG. 7.

That is, if the fluorescence image brightness adjustment process is started, in step S131, the fluorescence average luminance calculation unit 171 calculates the average luminance ($I_{FL}$ with overline) of the fluorescence image, and in step S132 the fluorescence average luminance determination unit 172 determines whether or not the average luminance ($I_{FL}$ with overline) is larger than a predetermined threshold value $Th_{FL}$. In a case where it is determined that the average luminance ($I_{FL}$ with overline) is larger than the predetermined threshold value $Th_{FL}$, the fluorescence image brightness adjustment process is ended, and the process returns to FIG. 5 and proceeds to step S105 (Return 1).

In addition, in a case where it is determined in step S132 that the average luminance ($I_{FL}$ with overline) is equal to or smaller than the predetermined threshold value $Th_{FL}$, in step S133, the pixel addition mode setting unit 173 determines whether or not the pixel addition mode can be set, In a case where it is determined that the pixel addition mode can still be set or in a case where it is determined that the number of pixels to which the pixel values are added can be increased in the pixel addition mode, in step S134, the pixel addition mode setting unit 173 sets the pixel addition mode or increases the number of pixels to which the pixel values are added in the pixel addition mode. Upon completion of the process of step S134, the fluorescence image brightness adjustment process is ended, the process returns to FIG. 5 and returns to step S101, and the subsequent processes are repeated (Return 2).

In addition, in a case where it is determined in step S133 that the pixel addition mode cannot be set or in a case where it is determined that the number of pixels cannot be increased any more in the pixel addition mode, the fluorescence image brightness adjustment process is ended, and the process returns to FIG. 5 and proceeds to step S105 (Return 1).

That is, in this case, in a case where the brightness of the fluorescence image is not sufficient even if the number of pixels to which the pixel values are added in the pixel addition mode has reached the upper limit, the further brightness adjustment is abandoned without increasing the light amount of the irradiation light, and the process proceeds. That is, although the brightness is insufficient, since the process is progressed in a state where the brightness adjustment is performed to the maximum extent (in a state where the brightness is as high as possible), the AGEs amount is more accurately obtained than that in a case where the brightness adjustment is not performed. In addition, in this case, since the light amount control of the irradiation light is omitted, the AGEs amount can be obtained at a higher speed and a lower load. Furthermore, in this case, since the light amount of the irradiation light is not increased, that is, since the light intensity is not increased, the AGEs amount can be obtained more safely. In addition, increase in power consumption can be suppressed.

In addition, in this case, in the UV reflection image brightness adjustment process, the method using the pixel addition mode and the method using the light amount control of the irradiation light may be combined. In addition, similarly to the case of the above-described fluorescence image brightness adjustment process, in the UV reflection image brightness adjustment process, the method of controlling the light amount of the irradiation light may be omitted.

Furthermore, only in the UV reflection image brightness adjustment process, the method of controlling the light amount of the irradiation light may be omitted; and in the fluorescence image brightness adjustment process, the method using the pixel addition mode and the method using the light amount control of the irradiation light may be combined.

<Omission of Method Using Pixel Addition Mode>

On the contrary, the method using the pixel addition mode may be omitted, and the brightness adjustment may be performed by using the method of controlling the light amount of the irradiation light. For example, in the fluorescence image brightness adjustment process, the brightness adjustment may be performed by using only the method of controlling the light amount of the irradiation light; and in the UV reflection image brightness adjustment process, the brightness adjustment may be performed by combination of the method using the pixel addition mode and the method using the light amount control of the irradiation light. Furthermore, for example, in the UV reflection image brightness adjustment process, the brightness adjustment may be performed by using only the method of controlling the light amount of the irradiation light; and in the fluorescence image brightness adjustment process, the brightness adjustment may be performed by combination of the method using the pixel addition mode and the method using the light amount control of the irradiation light.

Furthermore, for example, in one of the UV reflection image brightness adjustment process and the fluorescence image brightness adjustment process, the brightness adjustment may be performed by using only the method of controlling the light amount of the irradiation light, and in the other thereof, the brightness adjustment may be performed by the method of using the pixel addition mode.

<Brightness Adjustment Using Contrast>

In the above description, the brightness of the image is determined by using the average luminance, but the parameter used for this determination is arbitrary as long as the parameter is information associated with the image, and the parameter may be a parameter other than the average luminance. For example, the contrast of the image may be used. For example, the fluorescence brightness adjustment unit 154 may adjust the brightness of the fluorescence image by using the contrast of the fluorescence image.

<Fluorescence Brightness Adjustment Unit>

Figure 11:
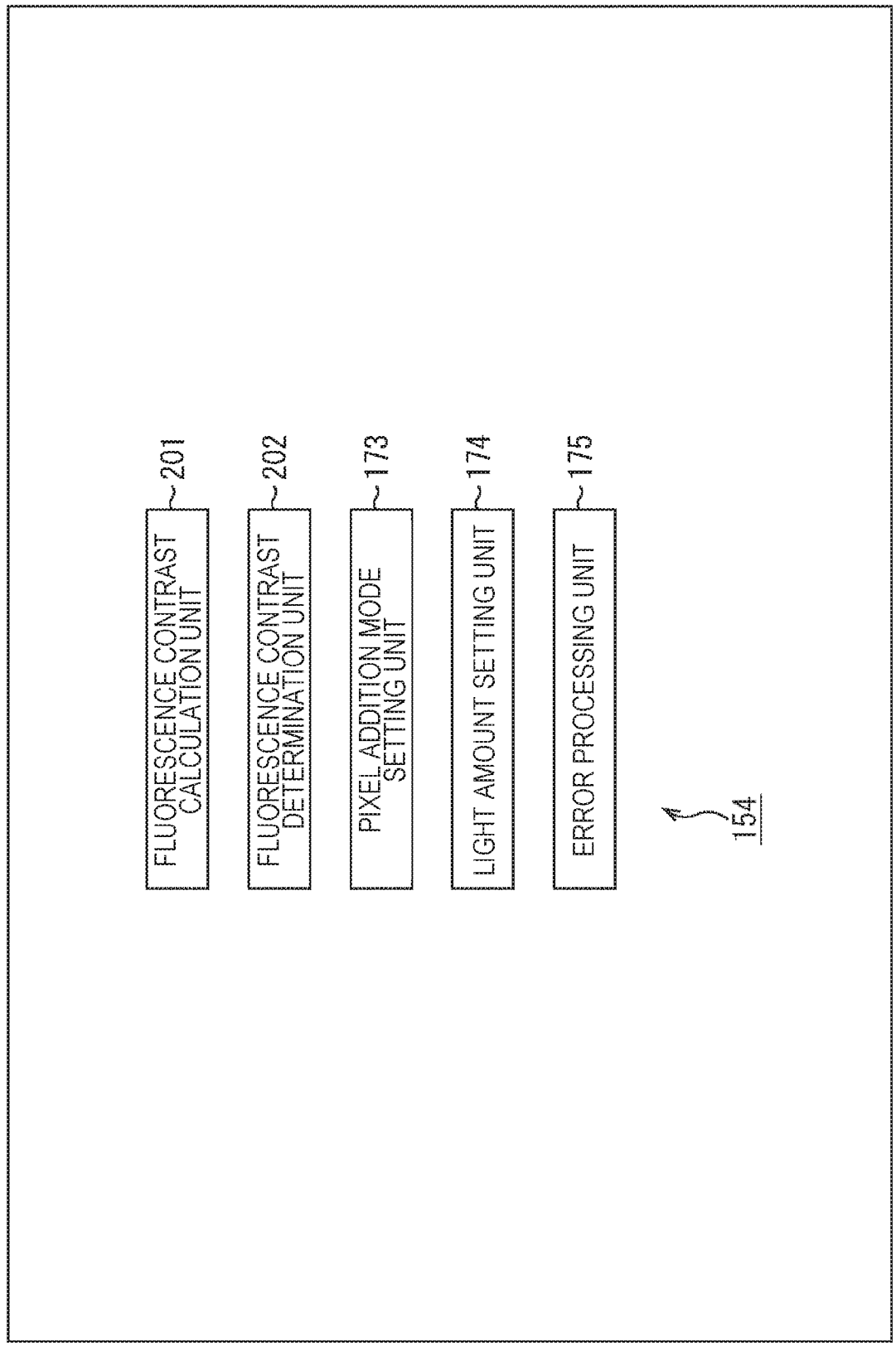
FIG. 11 is a functional block diagram illustrating a main configuration example of the fluorescence brightness adjustment unit.

FIG. 11 is a functional block diagram illustrating an example of main functions of the fluorescence brightness adjustment unit 154 in this case. As illustrated in FIG. 11, in this case, the fluorescence brightness adjustment unit 154 may have functions of, for example, the fluorescence contrast calculation unit 201, the fluorescence contrast determination unit 202, and the pixel addition mode setting unit 173 to the error processing unit 175. The fluorescence contrast calculation unit 201 performs processing related to the calculation of the contrast of the fluorescence image. The fluorescence contrast determination unit 202 performs processing related to the determination on the contrast of the fluorescence image.

<Flow of Fluorescence Image Brightness Adjustment Process>

Figure 12:
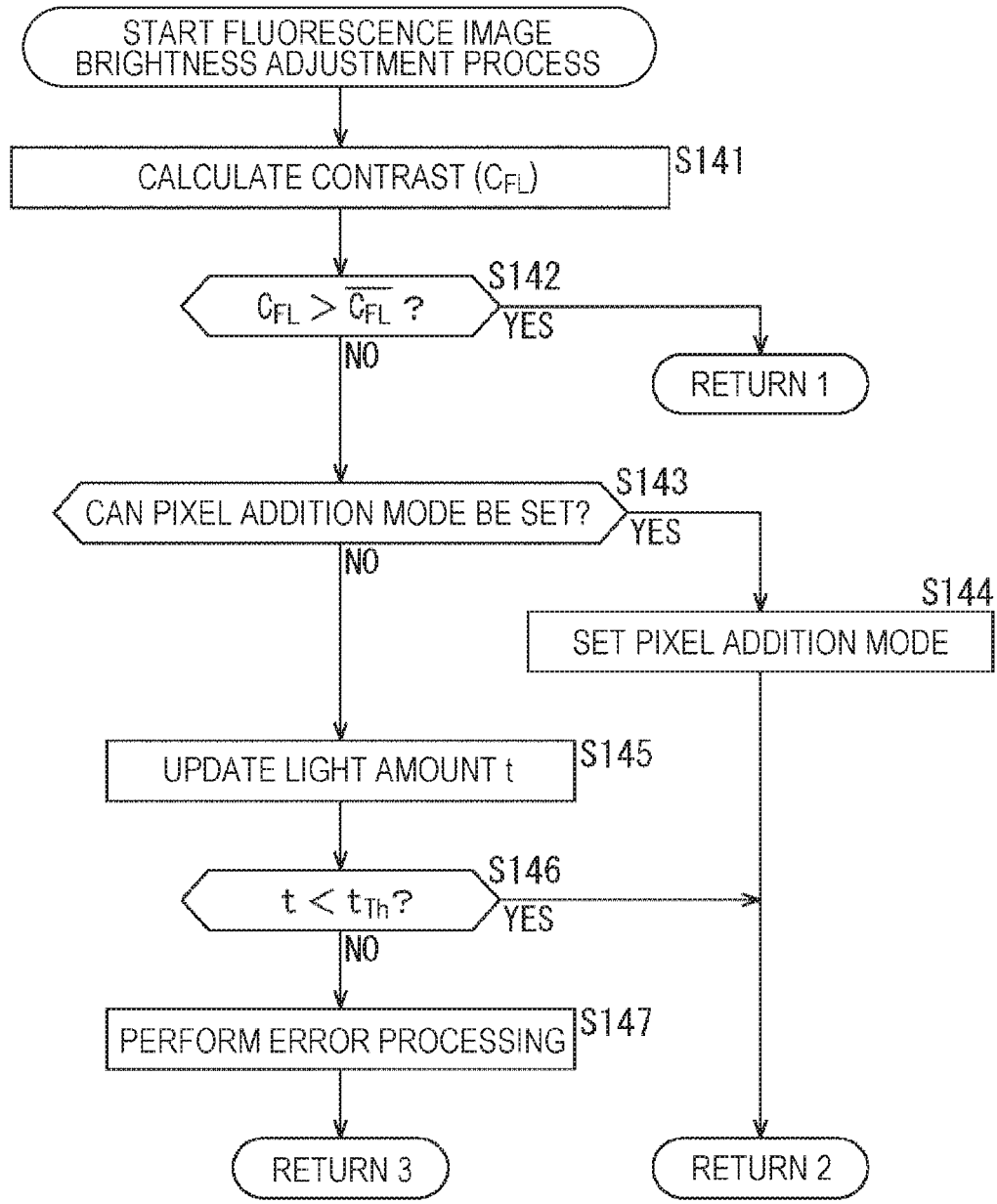
FIG. 12 is a flowchart illustrating an example of a flow of a fluorescence image brightness adjustment process.

An example of a flow of the fluorescence image brightness adjustment process in this case will be described with reference to a flowchart of FIG. 12. If the fluorescence image brightness adjustment process is started, the fluorescence contrast calculation unit 201 calculates the contrast ($C_{FL}$) of the fluorescence image in step S141.

In step S142, the fluorescence contrast determination unit 202 determines whether or not the contrast ($C_{FL}$) calculated in step S141 is larger than the average contrast ($C_{FL}$ with overline) of the fluorescence image obtained so far. In a case where it is determined that the contrast ($C_{FL}$) is larger than the average contrast ($C_{FL}$ with overline), that is, in a case where it is determined the fluorescence image is sufficiently bright, the fluorescence image brightness adjustment process is ended, and the process returns to FIG. 5 and proceeds to step S105 (Return 1).

In addition, in a case where it is determined in step S142 that the contrast ($C_{FL}$) is equal to or smaller than the average contrast ($C_{FL}$ with overline), that is, in a case where it is determined the brightness of the fluorescence image is not sufficient, the process proceeds to step S143.

Figure 7:
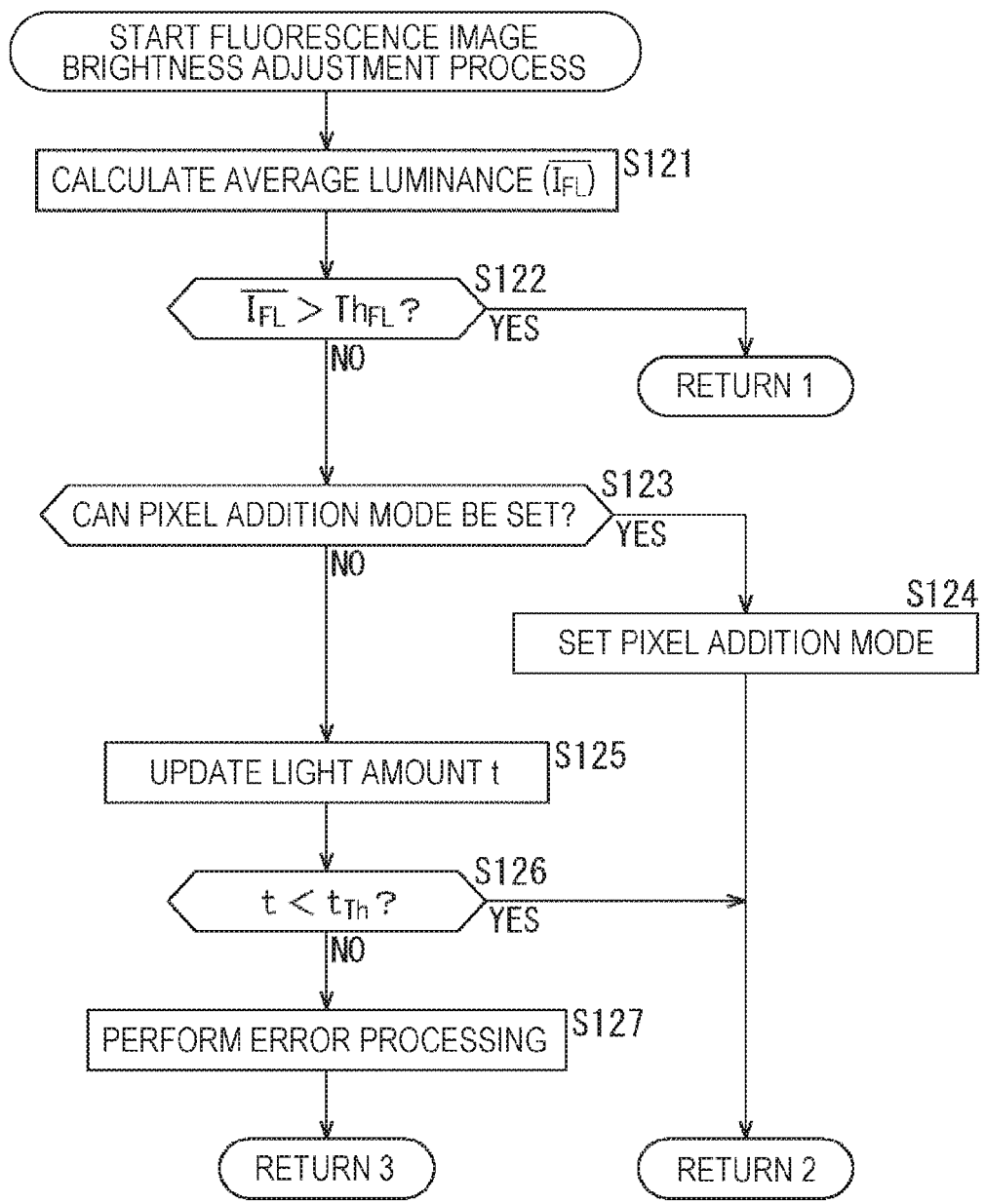
FIG. 7 is a flowchart illustrating an example of a flow of a fluorescence image brightness adjustment process.

The processes of steps S143 to S147 are executed in a manner similar to those of the processes of steps S123 to S127 of FIG. 7.

In this manner, by adjusting the brightness of the fluorescence image by using the contrast, the SAF (AF value) can be obtained more accurately, similarly to a case where the brightness of the fluorescence image is adjusted by using the average luminance.

In addition, similarly to the case of the above-described fluorescence image brightness adjustment process, in the UV reflection image brightness adjustment process, the brightness of the UV reflection image may be adjusted by using the contrast of the UV reflection image. Furthermore, the contrast may be used in one of the UV reflection image brightness adjustment process and the fluorescence image brightness adjustment process, and the average luminance may be used in the other.

<Omission of Method of Controlling Light Amount of Irradiation Light>

Figure 13:
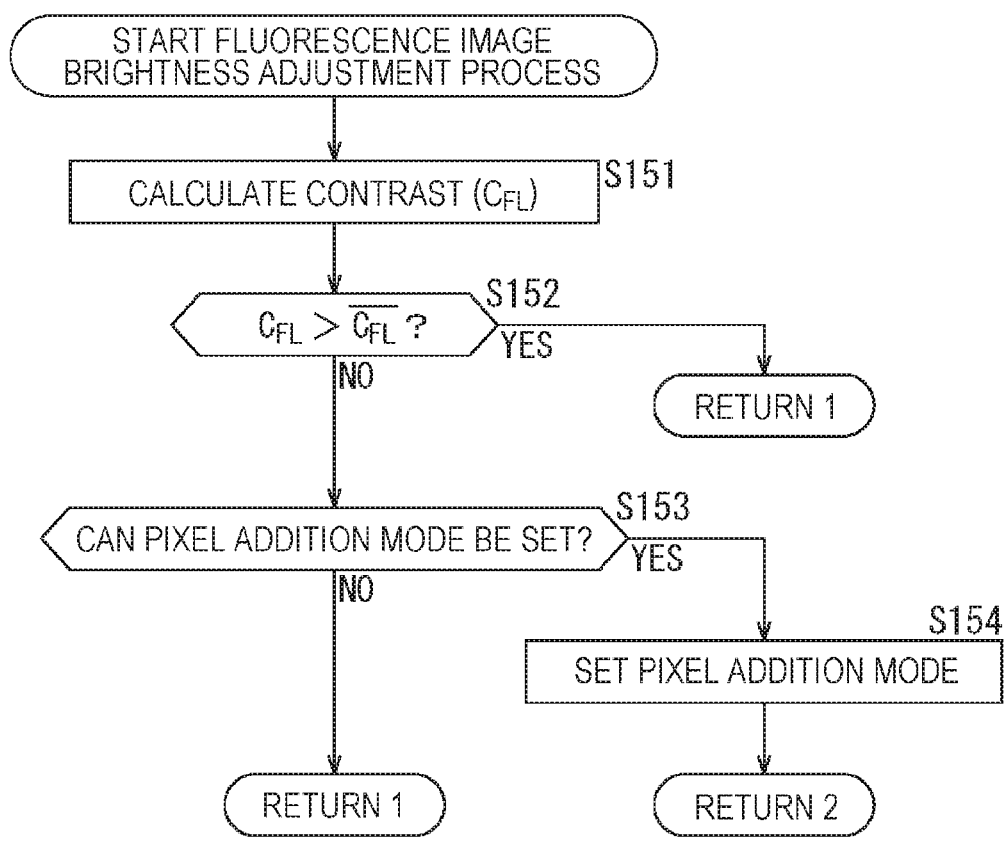
FIG. 13 is a flowchart illustrating an example of a flow of a fluorescence image brightness adjustment process.

Of course, even in a case where the contrast is used, the method of controlling the light amount of the irradiation light may be omitted. An example of a flow of the fluorescence image brightness adjustment process in this case will be described with reference to a flowchart of FIG. 13. In this case, the fluorescence brightness adjustment unit 154 performs the processes of steps S151 to S154 basically in a manner similar to those of the processes of steps S141 to S144 of FIG. 12.

That is, if the fluorescence image brightness adjustment process is started, in step S151, the fluorescence contrast calculation unit 201 calculates the contrast ($C_{FL}$) of the fluorescence image, and in step S152, the fluorescence contrast determination unit 202 determines whether or not the contrast ($C_{FL}$) Is larger than the average contrast ($C_{FL}$ with overline) of the fluorescence image obtained so far. In a case where it is determined that the contrast ($C_{FL}$) is larger than the average contrast ($C_{FL}$ with overline), the fluorescence image brightness adjustment process is ended, and the process returns to FIG. 5 and proceeds to step S105 (Return 1).

In addition, in a case where it is determined in step S152 that the contrast ($C_{FL}$) is equal to or smaller than the average contrast ($C_{FL}$ with overline), in step S153, the pixel addition mode setting unit 173 determines whether or not the pixel addition mode can be set, In a case where it is determined that the pixel addition mode can still be set or in a case where it is determined that the number of pixels to which the pixel values are added can be increased in the pixel addition mode, in step S154, the pixel addition mode setting unit 173 sets the pixel addition mode or increases the number of pixels to which the pixel values are added in the pixel addition mode. Upon completion of the process of step S154, the fluorescence image brightness adjustment process is ended, the process returns to FIG. 5 and returns to step S101, and the subsequent processes are repeated (Return 2).

In addition, in a case where it is determined in step S153 that the pixel addition mode cannot be set or in a case where it is determined that the number of pixels cannot be increased any more in the pixel addition mode, the fluorescence image brightness adjustment process is ended, and the process returns to FIG. 5 and proceeds to step S105 (Return 1).

That is, in this case, in a case where the brightness of the fluorescence image is not sufficient even if the number of pixels to which the pixel values are added in the pixel addition mode has reached the upper limit, the further brightness adjustment is abandoned without increasing the light amount of the irradiation light, and the process proceeds. That is, although the brightness is insufficient, since the process is progressed in a state where the brightness adjustment is performed to the maximum extent (in a state where the brightness is as high as possible), the AGEs amount is more accurately obtained than that in a case where the brightness adjustment is not performed. In addition, in this case, since the light amount control of the irradiation light is omitted, the AGEs amount can be obtained at a higher speed and a lower load. Furthermore, in this case, since the light amount of the irradiation light is not increased, that is, the light intensity is not increased, the AGEs amount can be obtained more safely. In addition, increase in power consumption can be suppressed.

In addition, in this case, in the UV reflection image brightness adjustment process, the method using the pixel addition mode and the method using the light amount control of the irradiation light may be combined. In addition, similarly to the case of the above-described fluorescence image brightness adjustment process, in the UV reflection image brightness adjustment process, the method of controlling the light amount of the irradiation light may be omitted.

Furthermore, only in the UV reflection image brightness adjustment process, the method of controlling the light amount of the irradiation light may be omitted; and in the fluorescence image brightness adjustment process, the method using the pixel addition mode and the method using the light amount control of the irradiation light may be combined.

<Omission of Method Using Pixel Addition Mode>

On the contrary, the method using the pixel addition mode may be omitted, and the brightness adjustment may be performed by using the method of controlling the light amount of the irradiation light. For example, in the fluorescence image brightness adjustment process, the brightness adjustment may be performed by using only the method of controlling the light amount of the irradiation light; and in the UV reflection image brightness adjustment process, the brightness adjustment may be performed by combination of the method using the pixel addition mode and the method using the light amount control of the irradiation light. Furthermore, for example, in the UV reflection image brightness adjustment process, the brightness adjustment may be performed by using only the method of controlling the light amount of the irradiation light; and in the fluorescence image brightness adjustment process, the brightness adjustment may be performed by combination of the method using the pixel addition mode and the method using the light amount control of the irradiation light.

Furthermore, for example, in one of the UV reflection image brightness adjustment process and the fluorescence image brightness adjustment process, the brightness adjustment may be performed by using only the method of controlling the light amount of the irradiation light; and in the other thereof, the brightness adjustment may be performed by using only the method using the pixel addition mode.

<Combined Use of Average Luminance and Contrast>

In addition, the brightness of the image may be determined by using both the contrast and the average luminance of the image. For example, by determining the brightness by using each of the contrast and the average luminance, even in a case where it is determined that the brightness is sufficient in both determinations (or at least one determination), the calculation of the SAF may be performed. Furthermore, a new parameter including both the contrast and the average luminance may be calculated, and the brightness may be determined by using the parameter.

<Brightness Adjustment Using Control of Exposure Time>

In the above description, the method of using the pixel addition mode and the method using the light amount control of the irradiation light are described as the method of the brightness adjustment, but the method of the brightness adjustment is arbitrary, and other methods may be used. For example, the brightness of the UV reflection image or the fluorescence image may be adjusted by controlling the exposure time of the light receiving unit (CIS 105 or CIS 109).

For example, in the initial setting, the exposure time of the light receiving unit (CIS 105 or CIS 109) bay be set to a normal time (also referred to as a short-accumulation mode), and in a case where the brightness is insufficient, the exposure time of the light receiving unit may be set to a longer time (also referred to as a long-accumulation mode). In a case where the brightness is still insufficient, the exposure time may be further increased.

In addition, as the exposure time is increased in this manner, any one of the pixel values is saturated, and the difference of the UV reflection image and the fluorescence image from the case of the short-accumulation mode is increased (deterioration of the UV reflection image or the fluorescence image is increased). For this reason, there is a possibility that it is more difficult to calculate the accurate AGEs amount. For this reason, an upper limit may be set for the exposure time so as not to increase the deterioration of the UV reflection image or the fluorescence image by the adjustment of the exposure time by a certain amount or more.

Furthermore, a method using the exposure time control and a method using the light amount control of the irradiation light may be combined. That is, instead of the above-described method using the pixel addition mode, the method the using exposure time control may be applied.

<UV Brightness Adjustment Unit>

Figure 14:
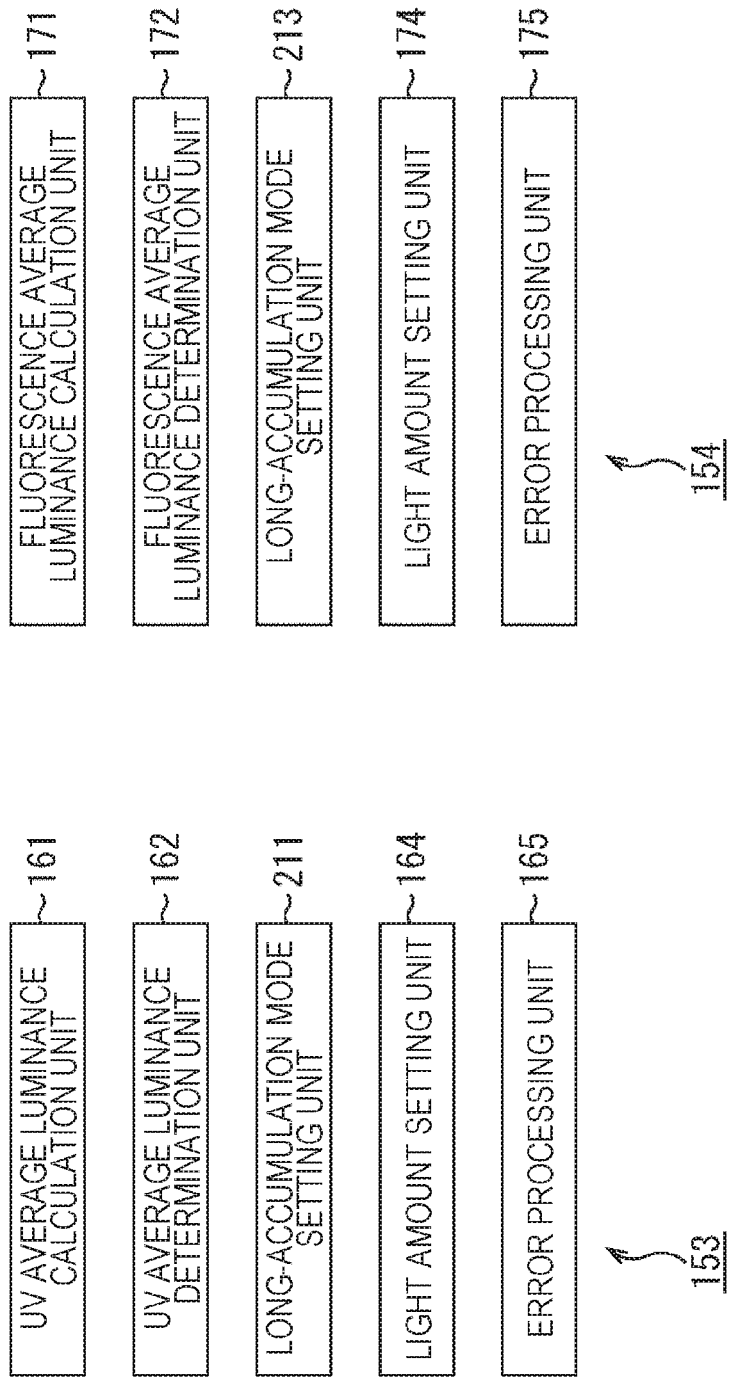
FIGS. 14A and 14B are functional block diagrams illustrating main configuration examples of a UV brightness adjustment unit and a fluorescence brightness adjustment unit.

FIG. 14A is a functional block diagram illustrating an example of main functions of the UV brightness adjustment unit 153 in this case. As illustrated in FIG. 14A, in this case, the UV brightness adjustment unit 153 may have functions of, for example, a UV average luminance calculation unit 161, a UV average luminance determination unit 162, a long-accumulation mode setting unit 211, a light amount setting unit 164, and an error processing unit 165. The long-accumulation mode setting unit 211 performs processing related to the setting of the exposure time of the CIS 105.

<Fluorescence Brightness Adjustment Unit>

FIG. 14B is a functional block diagram illustrating an example of main functions of the fluorescence brightness adjustment unit 154 in this case. In this case, as illustrated in FIG. 14B, in this case, the fluorescence brightness adjustment unit 154 may have functions of, for example, a fluorescence average luminance calculation unit 171, a fluorescence average luminance determination unit 172, a long-accumulation mode setting unit 213, a light amount setting unit 174, and an error processing unit 175. The long-accumulation mode setting unit 213 performs processing relating to the setting of the exposure time of the CIS 109.

<Flow of UV Reflection Image Brightness Adjustment Process>

Figure 15:
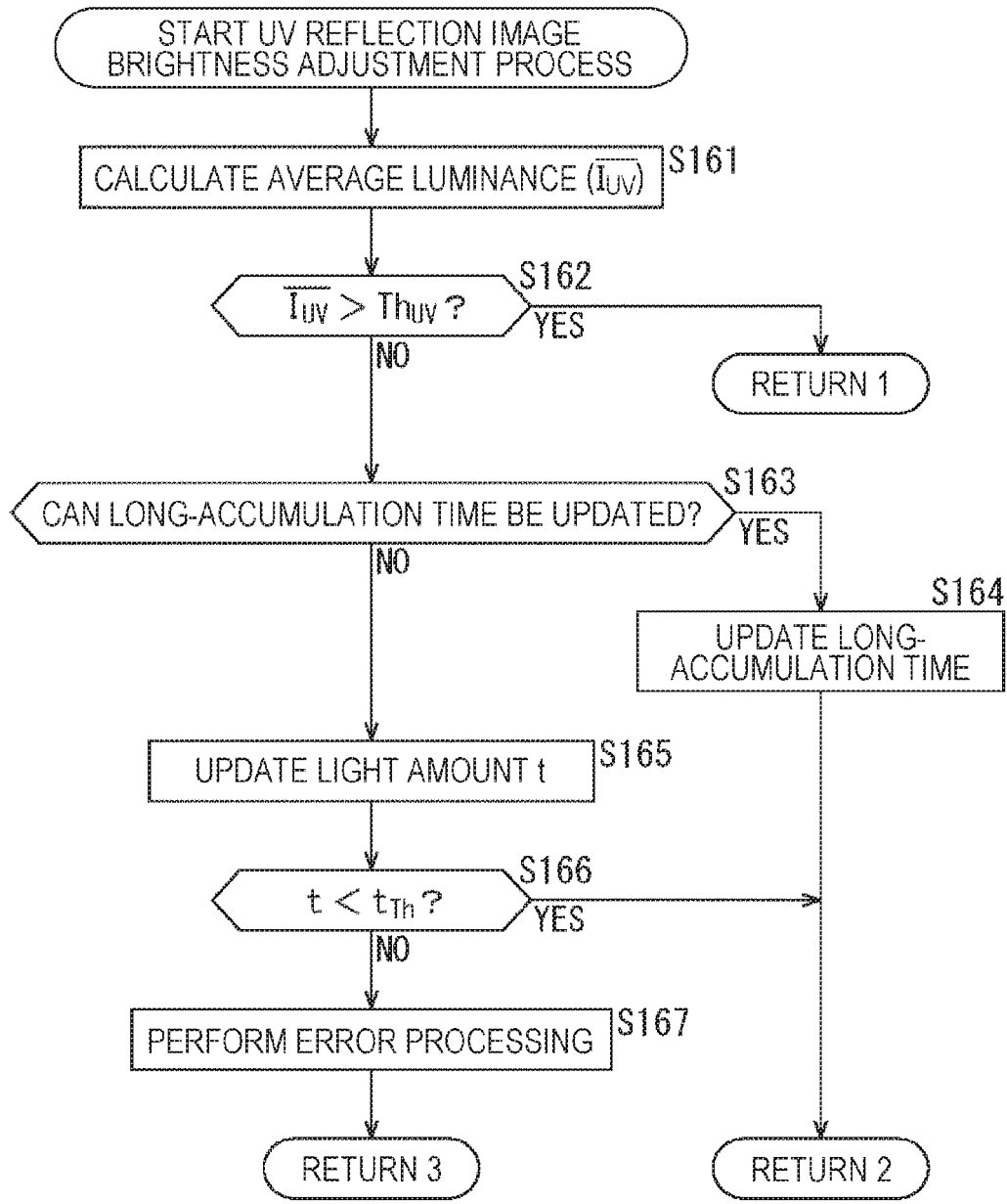
FIG. 15 is a flowchart illustrating an example of a flow of a UV reflection image brightness adjustment process.

Also in this case, the AGES amount calculation process is executed in a manner similar to that of the case described with reference to a flowchart of FIG. 5. Next, an example of a flow of a UV reflection image brightness adjustment process in this case will be described with reference to a flowchart of FIG. 15.

Figure 6:
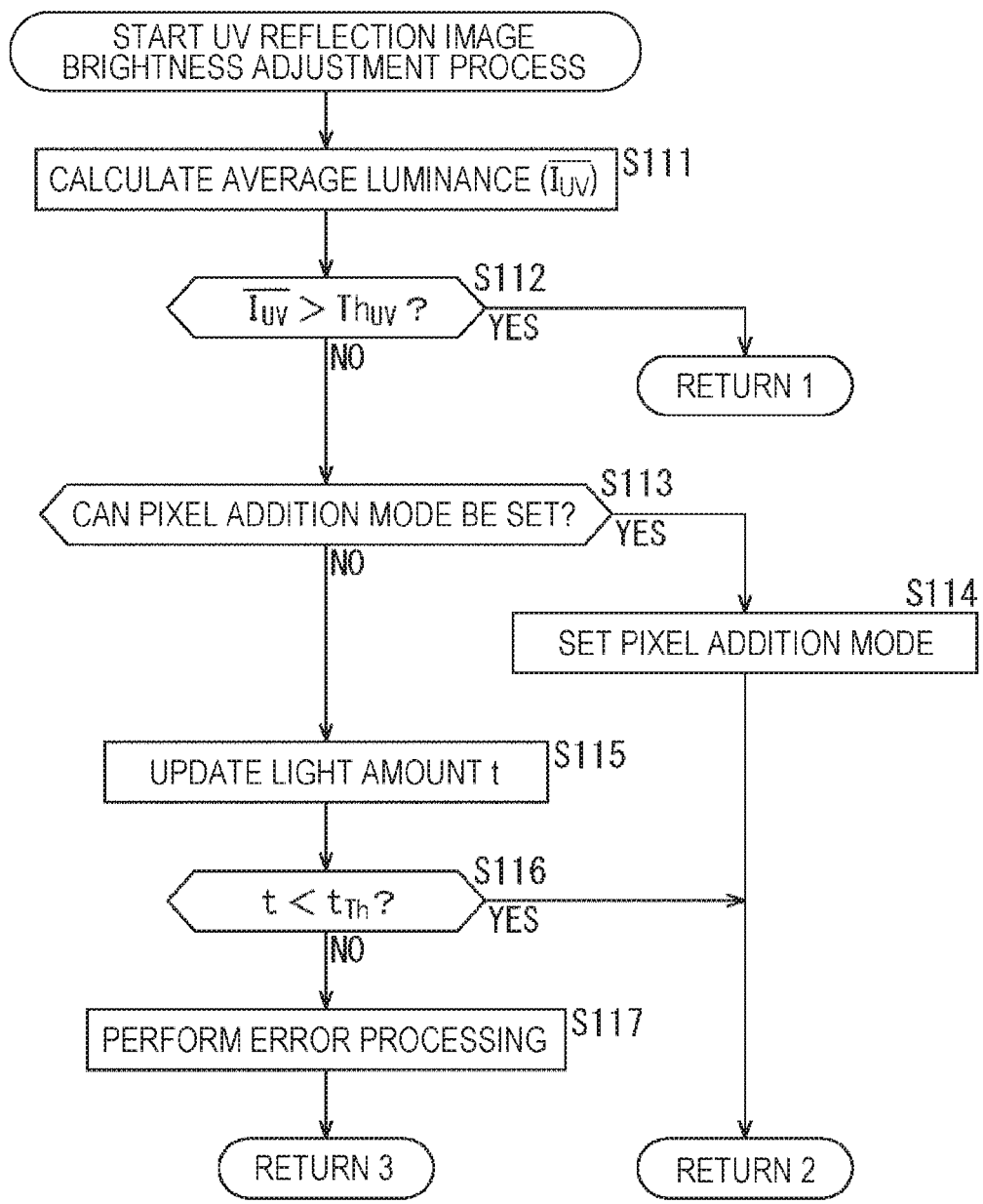
FIG. 6 is a flowchart illustrating an example of a flow of a UV reflection image brightness adjustment process.

The processes of steps S161 and S162 are executed in a manner similar to those of the processes of steps S111 and S112 in FIG. 6. Then, in step S162, in a case where it is determined that the average luminance ($\overline{I_{UV}}$ with overline) is equal to or smaller than the predetermined threshold value $Th_{UV}$, that is, in a case where it is determined the brightness of the UV reflection image is not sufficient, the process proceeds to step S163.

In step S163, the long-accumulation mode setting unit 211 determines whether or not the updating of the long-accumulation time is possible. In a case where it is determined that the short-accumulation mode has been set or in a case where it is determined that the long-accumulation mode is set but the exposure time has not reached the upper limit (the exposure time can be still extended), the process proceeds to step S164.

In step S164, the long-accumulation mode setting unit 211 updates the exposure time of the CIS 105 to increase the exposure time. That is, in a case where the current exposure time of the CIS 105 is of the short-accumulation mode, the long-accumulation mode setting unit 211 changes the mode to the long-accumulation mode, and in a case where the current exposure time is of the long-accumulation mode, the long-accumulation mode setting unit further increases the exposure time. Upon completion of the process of step S164, the UV reflection image brightness adjustment process is ended, the process returns to FIG. 5 and returns to step S101, and the subsequent processes are repeated (Return 2).

In addition, in a case where it is determined in step S163 that the updating of the long-accumulation time is impossible and the exposure time cannot be further increased, the process proceeds to step S165.

The processes from step S165 to step S167 are executed in a manner similar to those of the processes from step S115 to step S117 in FIG. 6.

<Flow of Fluorescence Image Brightness Adjustment Process>

Next, an example of a flow of a fluorescence image brightness adjustment process in this case will be described with reference to a flowchart of FIG. 16. In this case, the fluorescence image brightness adjustment process is basically executed in a manner similar to that of the UV reflection image brightness adjustment process in FIG. 15.

The processes of steps S171 and S172 are executed in a manner similar to those of the processes of steps S121 and S122 in FIG. 7. Then, in a case where it is determined in step S172 that the average luminance ($\overline{I_{FL}}$ with overline) is equal to or smaller than the predetermined threshold value $Th_{FL}$, that is, in a case where it is determined that the brightness of the fluorescence image is not sufficient, the process proceeds to step S173.

In step S173, the long-accumulation mode setting unit 213 determines whether or not the updating of the long-accumulation time is possible. In a case where it is determined that the short-accumulation mode has been set or in a case where it is determined that the long-accumulation mode is set but the exposure time has not reached the upper limit (the exposure time can be still extended), the process proceeds to step S174.

In step S174, the long-accumulation mode setting unit 213 updates the exposure time of the CIS 109 to increase the exposure time. That is, in a case where the current exposure time of the CIS 109 is in the short-accumulation mode, the long-accumulation mode setting unit 213 changes to the long-accumulation mode and further increases the exposure time in the case of the long-accumulation mode. Upon completion of the process of step S174, the fluorescence image brightness adjustment process is ended, the process returns to FIG. 5 and returns to step S101, and the subsequent processes are repeated (Return 2).

In addition, in a case where it is determined in step S173 that the updating of the long-accumulation time is impossible and the exposure time cannot be further increased, the process proceeds to step S175.

The processes of steps S175 to S177 are executed in a manner similar to those of the processes of steps S125 to S127 of FIG. 7.

As described above, by adjusting the brightness of the UV reflection image and the fluorescence image, the AGEs amount calculation unit 155 can more accurately obtain the AF value.

<Omission of Method of Controlling Light Amount of Irradiation Light>

In addition, in the above description, an example in which a combination of the method of controlling the exposure time and the method of controlling the light amount of the irradiation light is applied for the brightness adjustment has been described, but the method of controlling the light amount of the irradiation light may be omitted.

An example of a flow of the fluorescence image brightness adjustment process in this case will be described with reference to a flowchart of FIG. 17. In this case, the fluorescence brightness adjustment unit 154 performs the processes of steps S181 to S184 basically in a manner similar to those of the processes of steps S171 to S174 of FIG. 16.

In a case where it is determined in step S182 that the average luminance ($I_{FL}$ with overline) is larger than the predetermined threshold value $Th_{FL}$, the fluorescence image brightness adjustment process is ended, and the process returns to FIG. 5 and proceeds to step S105 (Return 1), In addition, upon completion of the process of step S184, the fluorescence image brightness adjustment process is ended, the process returns to FIG. 5 and returns to step S101, and the subsequent processes are repeated (Return 2).

Furthermore, in a case where it is determined in step S183 that the updating of the long-accumulation time is impossible and that the exposure time cannot be further increased, the fluorescence image brightness adjustment process is ended, the process returns to FIG. 5, and proceed to step S105 (Return 1).

That is, in this case, in a case where the brightness of the fluorescence image is not sufficient even if the exposure time has reached the upper limit, the further brightness adjustment is abandoned without increasing the light amount of the irradiation light, and the process proceeds. That is, although the brightness is insufficient, since the process is progressed in a state where the brightness adjustment is performed to the maximum extent (in a state where the brightness is as high as possible), the AGEs amount is more accurately obtained than that in a case where the brightness adjustment is not performed. In this case, since the control of the light amount of the irradiation light is omitted, the AGEs amount can be obtained at a higher speed and a lower load. Furthermore, in this case, since the light amount of the irradiation light is not increased, that is, the light intensity is not increased, the AGEs amount can be obtained more safely. In addition, increase in power consumption can be suppressed.

In addition, in this case, in the UV reflection image brightness adjustment process, the method of controlling the exposure time and the method of using the light amount control of the irradiation light may be combined. In addition, similarly to the case of the above-described fluorescence image brightness adjustment process, in the UV reflection image brightness adjustment process, the method of controlling the light amount of the irradiation light may be omitted.

Furthermore, only in the UV reflection image brightness adjustment process, the method of controlling the light amount of the irradiation light may be omitted; and in the fluorescence image brightness adjustment process, the method of controlling the exposure time and the method of using the light amount control of the irradiation light may be combined.

<Omission of Method of Controlling Exposure Time>

On the contrary, the method of controlling the exposure time may be omitted, and the brightness adjustment may be performed by using the method of controlling the light amount of the irradiation light. For example, in the fluorescence image brightness adjustment process, the brightness adjustment may be performed by using only the method of controlling the light amount of the irradiation light; and in the UV reflection image brightness adjustment process, the brightness adjustment may be performed by combination of the method of controlling the exposure time and the method using the light amount control of the irradiation light. In addition, for example, in the UV reflection image brightness adjustment process, the brightness adjustment may be performed by using only a method of controlling the light amount of the irradiation light, and in the fluorescence image brightness adjustment process, the brightness adjustment may be performed by combination of the method of controlling the exposure time and the method using the light amount control of the irradiation light.

Furthermore, for example, in one of the UV reflection image brightness adjustment process and the fluorescence image brightness adjustment process, the brightness adjustment may be performed by using only the method of controlling the light amount of the irradiation light; and in the other thereof, the brightness adjustment may be performed by using only the method controlling the exposure time.

<Brightness Adjustment Using Contrast>

Also in the case of applying the method of control ling the exposure time for the brightness adjustment, the parameter used for the brightness determination of the image is arbitrary as long as the parameter is information associated with the image, and the parameter may be a parameter other than the average luminance. For example, the fluorescence brightness adjustment unit 154 may perform the brightness adjustment of the fluorescence image by using the contrast of the fluorescence image.

<Fluorescence Brightness Adjustment Unit>

Figure 18:
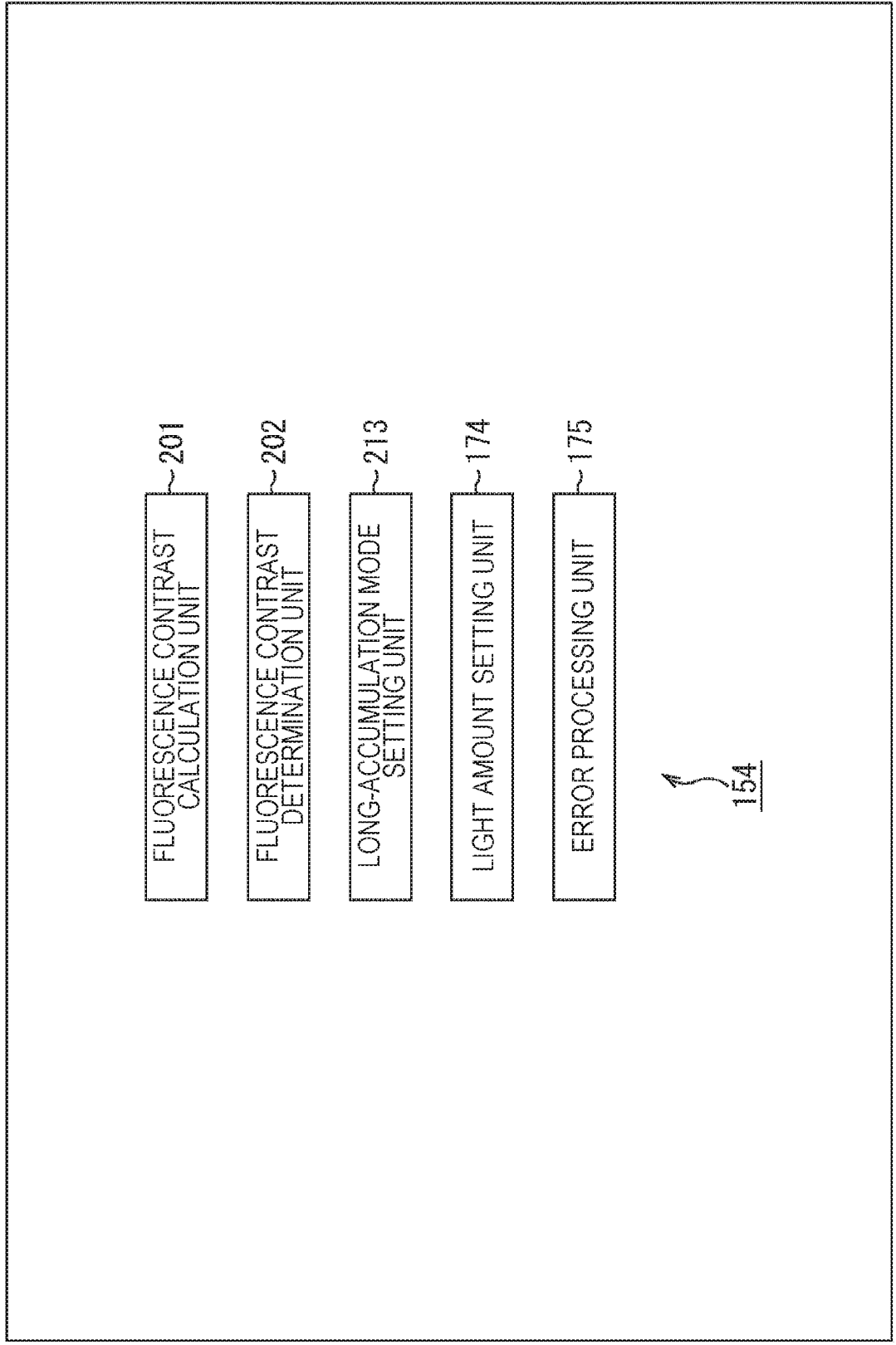
FIG. 18 is a functional block diagram illustrating a main configuration example of a fluorescence brightness adjustment unit.

FIG. 18 is a functional block diagram illustrating an example of main functions of the fluorescence brightness adjustment unit 154 in this case. As illustrated in FIG. 18, in this case, the fluorescence brightness adjustment unit 154 may have functions of, for example, a fluorescence contrast calculation unit 201, a fluorescence contrast determination unit 202, a long-accumulation mode setting unit 213, a light amount setting unit 174, and an error processing unit 175.

<Flow of Fluorescence Image Brightness Adjustment Process>

Figure 19:
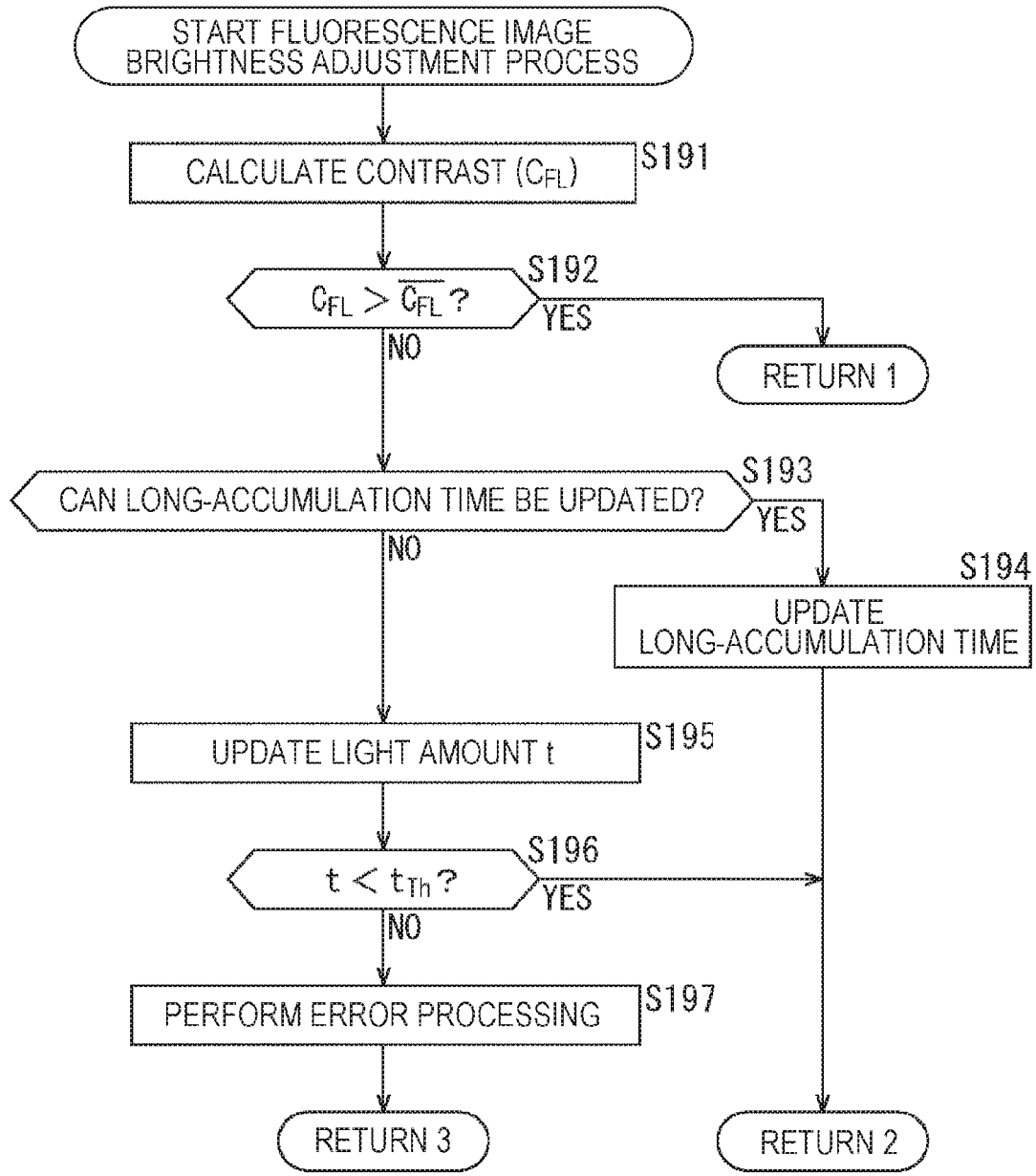
FIG. 19 is a flowchart illustrating an example of a flow of a fluorescence image brightness adjustment process.

An example of a flow of the fluorescence image brightness adjustment process in this case will be described with reference to a flowchart of FIG. 19. In this case, the fluorescence brightness adjustment unit 154 executes the processes of steps S191 and S192 in a manner similar to those of the processes of steps S141 and S142 of FIG. 12.

In a case where it is determined in step S192 that the contrast ($C_{FL}$) is larger than the average contrast ($C_{FL}$ with overline), that is, in a case where it is determined that the fluorescence image is sufficiently bright, the fluorescence image brightness adjustment process is ended, and the process returns to FIG. 5 and proceeds to step S105 (Return 1). In addition, in a case where it is determined in step S192 that the contrast ($C_{FL}$) is equal to or smaller than the average contrast ($C_{FL}$ with overline), that is, in a case where it is determined that the brightness of the fluorescence image is not sufficient, the process proceeds to step S193.

Figure 16:
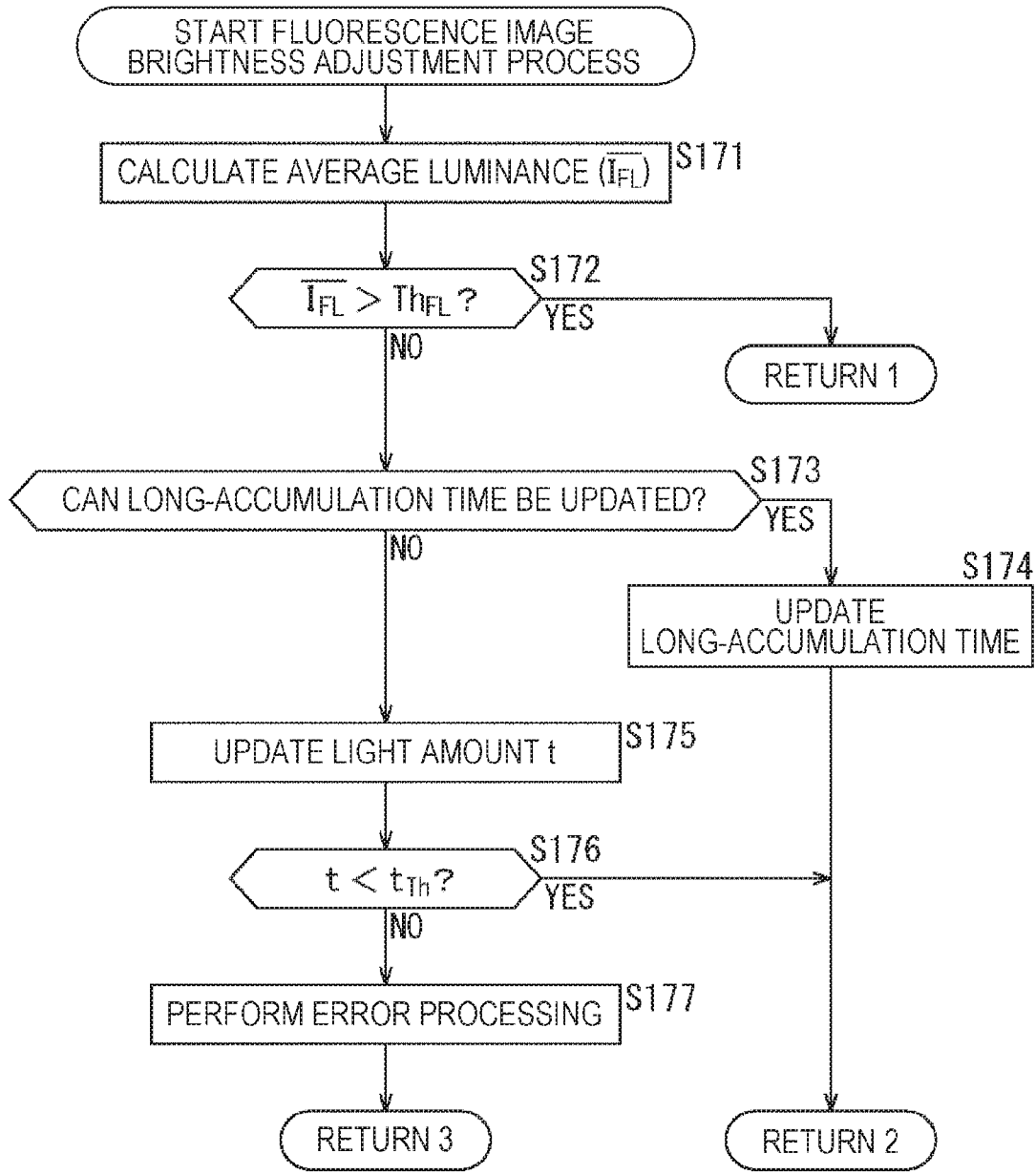
FIG. 16 is a flowchart illustrating an example of a flow of a fluorescence image brightness adjustment process.
Figure 17:
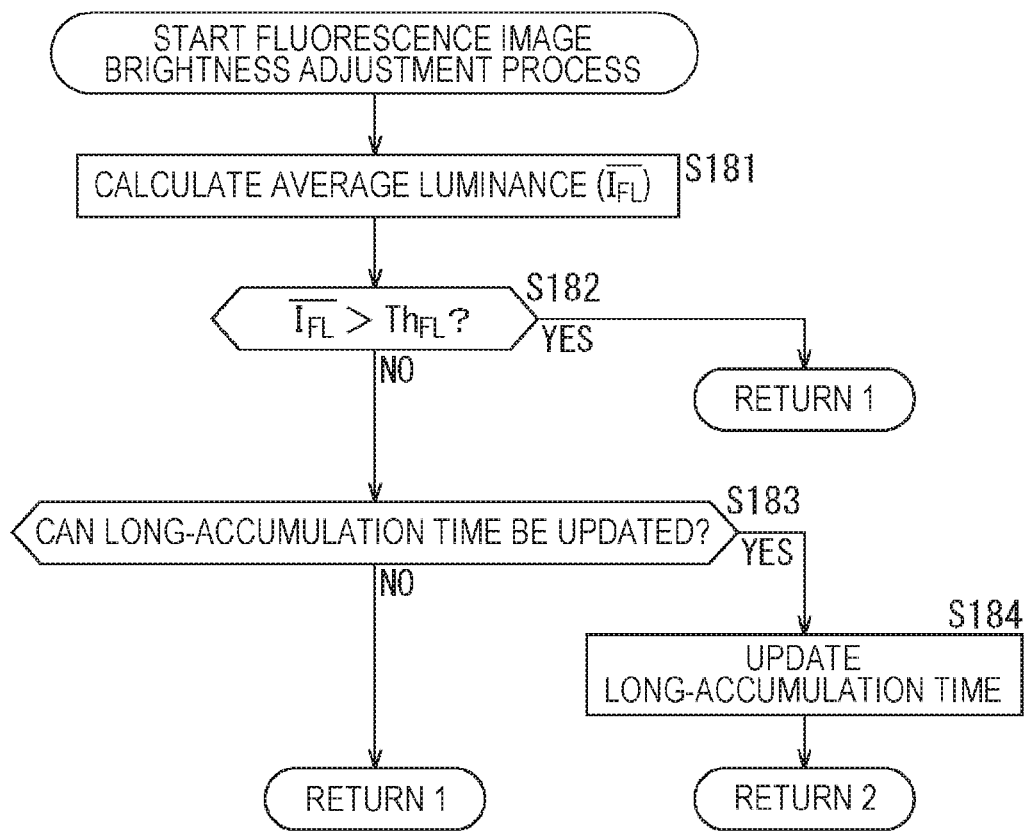
FIG. 17 is a flowchart illustrating an example of a flow of a fluorescence image brightness adjustment process.

The processes from step S193 to step S197 are executed in a manner similar to those of the processes from step S173 to step S177 in FIG. 16.

In this manner, by adjusting the brightness of the fluorescence image by using the contrast, the SAF (AF value) can be obtained more accurately, similarly to a case where the brightness of the fluorescence image is adjusted by using the average luminance.

In addition, in the UV reflection image brightness adjustment process, the brightness of the UV reflection image may be adjusted by using the contrast of the UV reflection image, similarly to the case of the above-described fluorescence image brightness adjustment process. Furthermore, the contrast may be used for any one of the UV reflection image brightness adjustment process and the fluorescence image brightness adjustment process, and the average luminance may be used for the other.

<Omission of Method of Controlling Light Amount of Irradiation Light>

Figure 20:
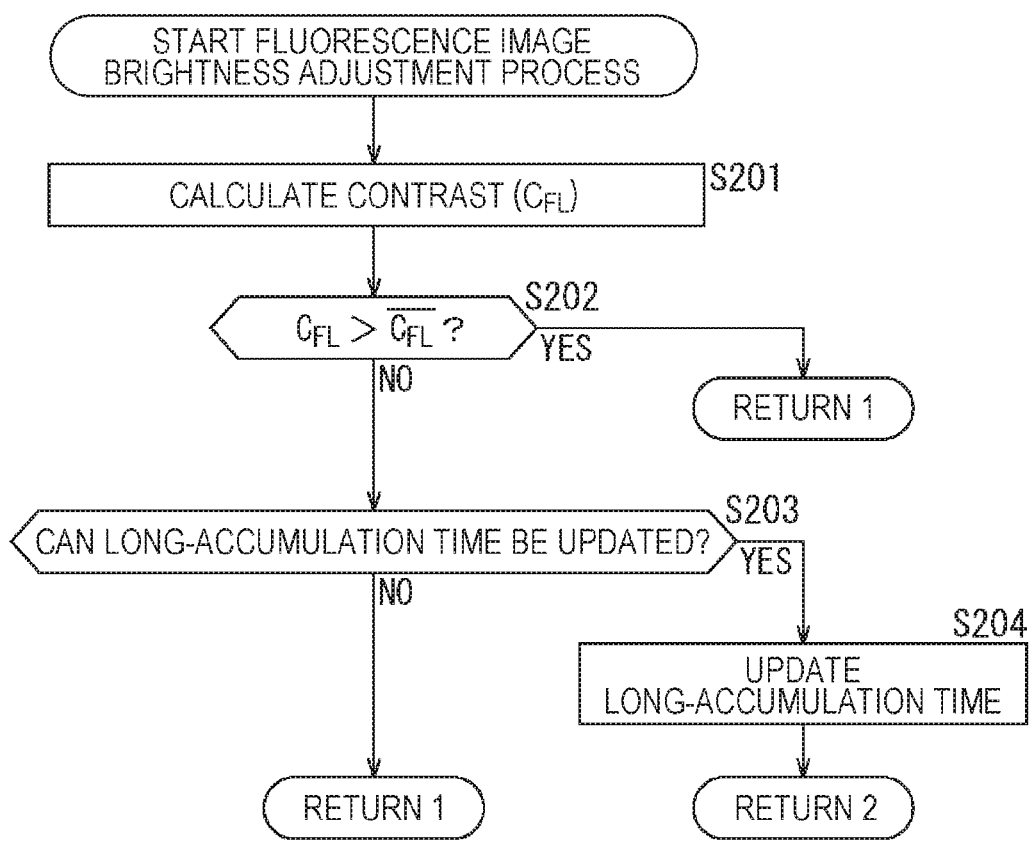
FIG. 20 is a flowchart illustrating an example of a flow of a fluorescence image brightness adjustment process.

Of course, even in a case where the contrast is used, the method of controlling the light amount of the irradiation light may be omitted. An example of a flow of the fluorescence image brightness adjustment process in this case will be described with reference to a flowchart of FIG. 20. In this case, the fluorescence brightness adjustment unit 154 performs the processes of steps S201 to S204 basically in a manner similar to those of the processes of steps S191 to S194 of FIG. 19.

In step S202, in a case where it is determined that the contrast ($C_{FL}$) is larger than the average contrast ($C_{FL}$ with overline), the fluorescence image brightness adjustment process is ended, and the process returns to FIG. 5 and the process proceeds to step S105 (Return 1).

In addition, upon completion of the process of step S204, the fluorescence image brightness adjustment process is ended, the process returns to FIG. 5 and returns to step S101, and the subsequent processes are repeated (Return 2).

Furthermore, in a case where it is determined in step S203 that the updating of the long-accumulation time is impossible and the exposure time cannot be further increased, the fluorescence image brightness adjustment process is ended, and the process returns to FIG. 5 and proceeds to step S105 (Return 1).

That is, in this case, in a case where the brightness of the fluorescence image is not sufficient even if the exposure time has reached the upper limit, the further brightness adjustment is abandoned without increasing the light amount of the irradiation light, and the process proceeds. That is, although the brightness is insufficient, since the process is progressed in a state where the brightness adjustment is performed to the maximum extent (in a state where the brightness is as high as possible), the AGEs amount is more accurately obtained than that in a case where the brightness adjustment is not performed. In this case, since the control of the light amount of the irradiation light is omitted, the AGEs amount can be obtained at a higher speed and a lower load. Furthermore, in this case, since the light amount of the irradiation light is not increased, that is, the light intensity is not increased, the AGEs amount can be obtained more safely. In addition, increase in power consumption can be suppressed.

In addition, in this case, in the UV reflection image brightness adjustment process, the method of controlling the exposure time and the method of using the light amount control of the irradiation light may be combined. In addition, similarly to the case of the above-described fluorescence image brightness adjustment process, in the UV reflection image brightness adjustment process, the method of controlling the light amount of the irradiation light may be omitted.

Furthermore, only in the UV reflection image brightness adjustment process, the method of controlling the light amount of the irradiation light may be omitted; and in the fluorescence image brightness adjustment process, the method of controlling the exposure time and the method of using the light amount control of the irradiation light may be combined.

<Omission of Method of Controlling Exposure Time>

On the contrary, the method of controlling the exposure time may be omitted, and the brightness adjustment may be performed by using the method of controlling the light amount of the irradiation light. For example, in the fluorescence image brightness adjustment process, the brightness adjustment may be performed by using only the method of controlling the light amount of the irradiation light; and in the UV reflection image brightness adjustment process, the brightness adjustment may be performed by combination of the method of controlling the exposure time and the method using the light amount control of the irradiation light. In addition, for example, in the UV reflection image brightness adjustment process, the brightness adjustment may be performed by using only the method of controlling the light amount of the irradiation light; and in the fluorescence image brightness adjustment process, the brightness adjustment may be performed by combination of the method of controlling the exposure time and the method using the light amount control of the irradiation light.

Furthermore, for example, in one of the UV reflection image brightness adjustment process and the fluorescence image brightness adjustment process, the brightness adjustment may be performed by using only the method of controlling the light amount of the irradiation light; and in the other thereof, the brightness adjustment may be performed by using only the method of controlling the exposure time.

<Combined Use of Average Luminance and Contrast>

In addition, in the case of applying the method of controlling the exposure time, the brightness of the image may be determined by using both the contrast and the average luminance of the image. For example, the brightness may be determined by using each of the contrast and the average luminance, and in a case where it is determined that the brightness is sufficient in both determinations (or at least one determination), the SAF may be calculated. Furthermore, new parameters including both the contrast and the average luminance may be calculated, and the brightness may be determined by using the parameters.

<Combination of Various Methods>

The brightness adjustment can be performed by using any method. That is, any of the method using the pixel addition mode, the method of controlling the light amount of the irradiation light, and the method of controlling the exposure time may be applied to the brightness adjustment. In addition, any arbitrary method other than these may be applied. Furthermore, a plurality of methods may be applied. For example, a combination of two or more of the above-described method using the pixel addition mode, the method of controlling the light amount of the irradiation light, and the method of controlling the exposure time may be applied. In addition, a combination with methods other than those described above may be applied.

In addition, the method of adjusting the brightness of the UV reflection image and the method of adjusting the brightness of the fluorescence image may be the same or different. For example, the number of methods applied to the brightness adjustment of the UV reflection image and the number of methods applied to the brightness adjustment of the fluorescence image may be different.

<Brightness Determination>

In addition, the parameter used for the brightness determination of an image is arbitrary as long as the parameter relates to the image, and parameters other than the average luminance and the contrast described above may be used. In addition, the brightness may be determined by using a plurality of parameters. Furthermore, the parameter used for the brightness determination of the UV reflection image and the parameter used for the brightness determination of the fluorescence image may be the same as each other or may be different from each other. For example, the number of parameters used for the brightness determination of the UV reflection image and the number of parameters used for the brightness determination of the fluorescence image may be the same as each other or may be different from each other.

<Unit of Brightness Adjustment>

The brightness adjustment of the UV reflection image or the fluorescence image described above may be performed on the entire image or may be performed for each predetermined partial region or for each pixel. In addition, such brightness adjustment may be performed only on a portion of the image.

In addition, for example, the target range for the brightness determination and the target range for the brightness adjustment may be different from each other. For example, the brightness determination may be performed on the basis of a predetermined portion of the image, and the brightness adjustment may be performed on the entire image. Furthermore, for example, the brightness determination may be performed on the entire image, and the brightness adjustment may be performed for each predetermined partial region or for each pixel.

3. Second Embodiment

<Correction of AGEs Amount>

As described above, the AGEs amount (predetermined indicator value) calculated on the basis of the reflected light in the two wavelength bands may be further corrected. For example, as described above, in some cases, melanin and redness may become error factors in a portion where a melanin pigment is deposited or a portion where redness occurs, and thus, it is difficult to accurately measure the AGEs amount. In a case where such an error factor is included within the measurement range, the AGEs amount (predetermined indicator value) may be corrected (updated) on the basis of the error factor so as to suppress the influence. With such a configuration, the measurement apparatus 100 can output a more accurate indicator value (AGEs amount).

<Control Unit>

Figure 21:
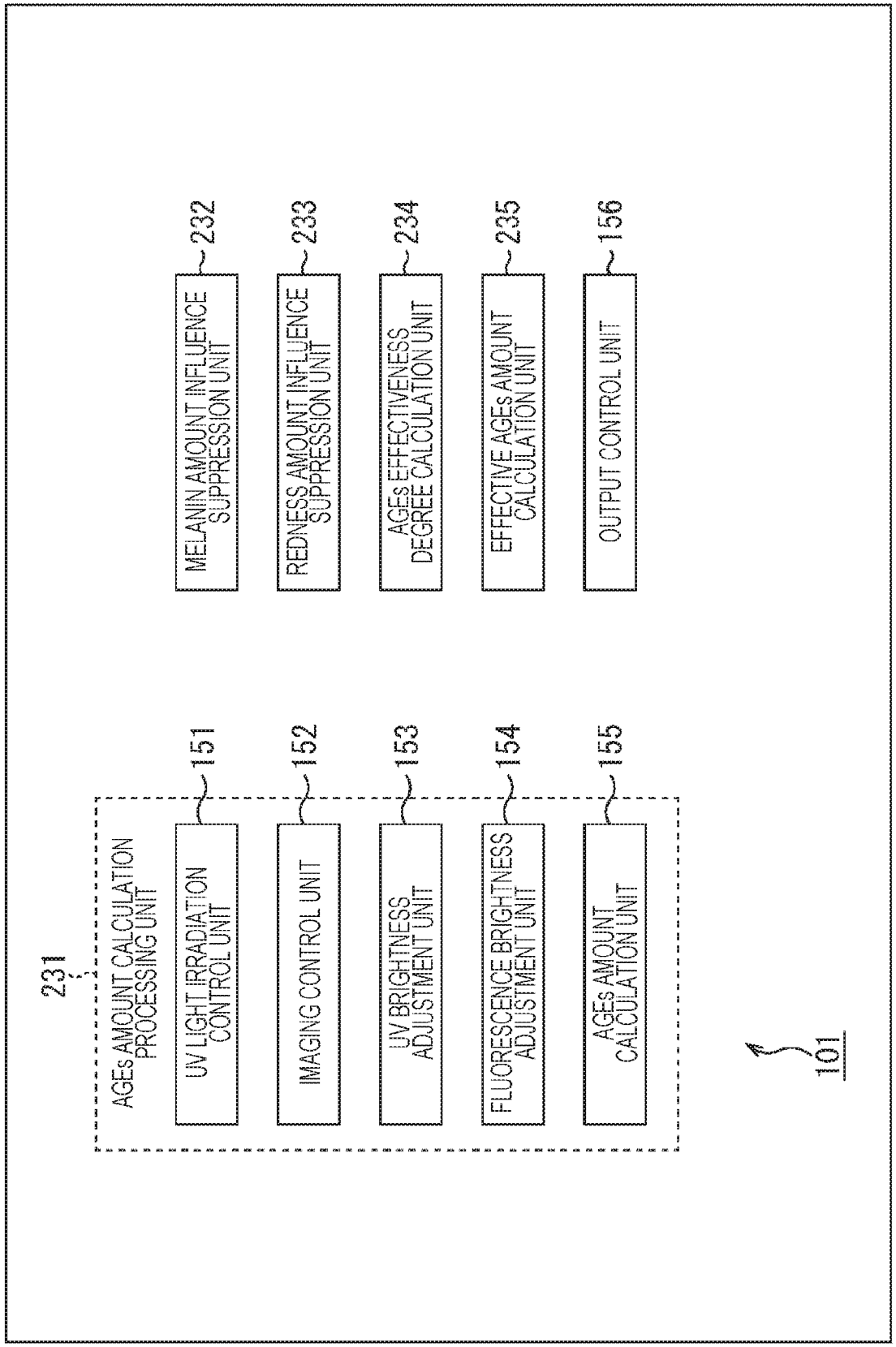
FIG. 21 is a functional block diagram illustrating functions realized by a control unit.

FIG. 21 is a functional block diagram illustrating an example of main functions realized by the control unit 101 executing a program and the like in this case. As illustrated in FIG. 21, in this case, by executing the program, the control unit 101 can have functions of, for example, an AGEs amount calculation processing unit 231, a melanin amount influence suppression unit 232, a redness amount influence suppression unit 233, an AGEs effectiveness degree calculation unit 234, an effective AGEs amount calculation unit 235, and an output control unit 156.

As described in the first embodiment, the AGEs amount calculation processing unit 231 performs processing relating to the calculation of the AGEs amount. That is, the AGEs amount calculation processing unit 231 has functions of the UV light irradiation control unit 151 to the AGEs amount calculation unit 155. The melanin amount influence suppression unit 232 performs processing relating to the suppression of the influence of the melanin on AGEs amount. The redness amount influence suppression unit 233 performs processing relating to the suppression of the influence of the redness on the AGEs amount. The AGEs effectiveness degree calculation unit 234 performs processing relating to the calculation of the AGEs effectiveness degree indicating the magnitude of the influence of the error factors (for example, melanin and redness) on the AGEs amount. The effective AGEs amount calculation unit 235 performs processing relating to the calculation of the effective AGEs amount obtained by correcting (updating) the AGEs amount on the basis of the error factors.

<Melanin Amount Influence Suppression Unit>

Figure 22:
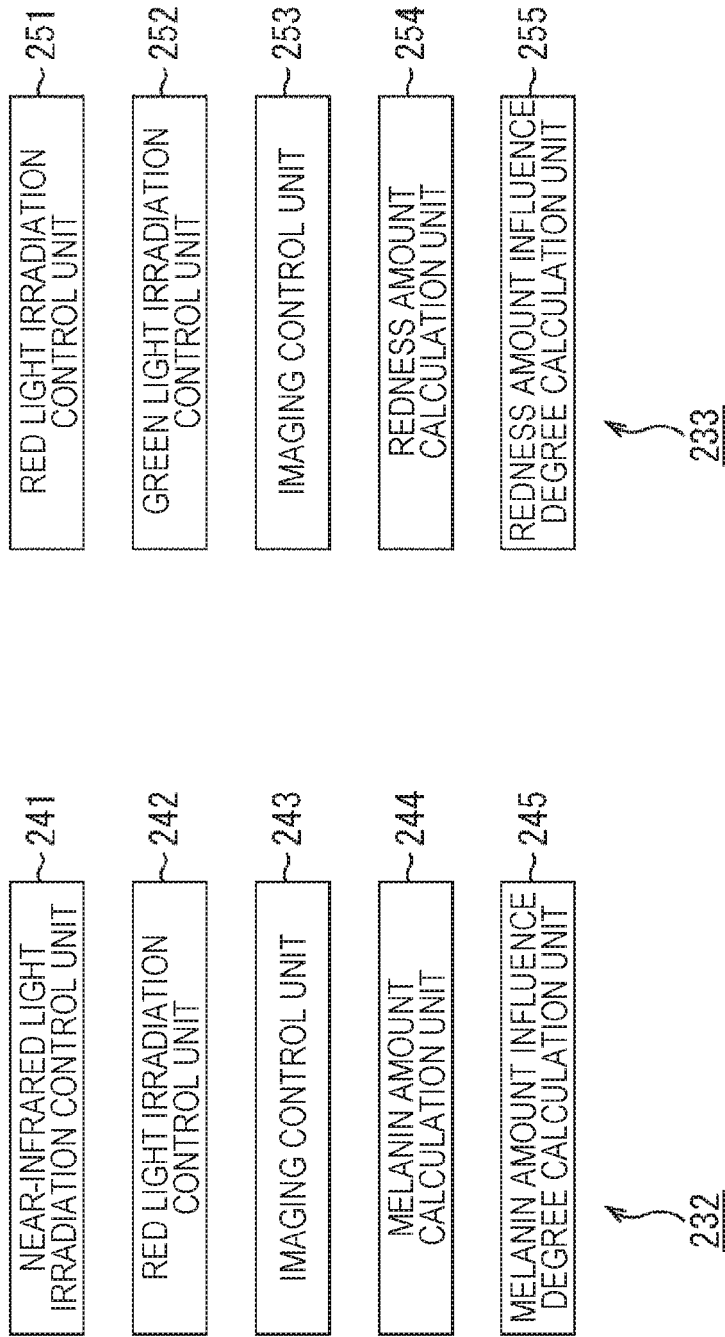
FIGS. 22A and 22B are functional block diagrams illustrating main configuration examples of a melanin amount influence suppression unit and a redness amount influence suppression unit.

FIG. 22A is a functional block diagram illustrating an example of main functions of the melanin amount influence suppression unit 232. As illustrated in FIG. 22A, the melanin amount influence suppression unit 232 may have functions of, for example, a near-infrared light irradiation control unit 241, a red light irradiation control unit 242, an imaging control unit 243, a melanin amount calculation unit 244, and a melanin amount influence degree calculation unit 245.

The near-infrared light irradiation control unit 241 performs control relating to the irradiation of near-infrared light (light having a wavelength of 880 nm). For example, the near-infrared light irradiation control unit 241 controls the LED 103 through the LED control unit 102 to emit near-infrared light (light having a wavelength of 880 nm) and to irradiate the human body 130 with the near-infrared light as irradiation light. In addition, in this embodiment, it is assumed that the LED 103 can emit light having an arbitrary wavelength and use the light as irradiation light.

The red light irradiation control unit 242 performs control relating to the irradiation of red light (light having a wavelength of 660 nm). For example, the red light irradiation control unit 242 controls the LED 103 through the LED control unit 102 to emit red light (light having a wavelength of 660 nm) and to irradiate the human body 130 with the red light as irradiation light.

The imaging control unit 243 performs control relating to the imaging of the measurement target region 135 by using the CIS 109. Since the filter 111 transmits the light having a wavelength band longer than that of blue, the filter can transmit reflected light of near-infrared light and red light. For example, under the control of the imaging control unit 243, the CIS 109 captures an image of the measurement target region 135 irradiated with the near-infrared light by the near-infrared light irradiation control unit 241 to generate an image data of the captured image of the near-infrared light (also, referred to as a captured near-infrared image). Furthermore, for example, under the control of the imaging control unit 243, the CIS 109 captures an image of the measurement target region 135 irradiated with red light by the red light irradiation control unit 242 to generate an image data of the captured image of the red light (also, referred to as a captured red image).

The melanin amount calculation unit 244 performs processing relating to the calculation of the melanin amount. The melanin amount influence degree calculation unit 245 performs processing relating to the calculation of the melanin amount influence degree indicating the magnitude of the influence of the melanin amount.

<Redness Amount Influence Suppression Unit>

FIG. 22B is a functional block diagram illustrating an example of main functions of the redness amount influence suppression unit 233. As illustrated in FIG. 22B, the redness amount influence suppression unit 233 may have functions of, for example, a red light irradiation control unit 251, a green light irradiation control unit 252, an imaging control unit 253, a redness amount calculation unit 254, and a redness amount influence degree calculation unit 255.

The red light irradiation control unit 251 performs control relating to the irradiation of red light (light having a wavelength of 660 nm). For example, the red light irradiation control unit 251 controls the LED 103 through the LED control unit 102 to emit red light (light having a wavelength of 660 nm) and to irradiate the human body 130 with the red light as irradiation light.

The green light irradiation control unit 252 performs control relating to the irradiation of green light (light having a wavelength of 570 nm). For example, the green light irradiation control unit 252 controls the LED 103 through the LED control unit 102 to emit green light (light having a wavelength of 570 nm) and to irradiate the human body 130 with the green light as irradiation light.

The imaging control unit 253 performs control relating to the imaging of the measurement target region 135 using the CIS 109. Since the filter 111 transmits the light having a wavelength band longer than that of blue, the filter can transmit reflected light of red light or green light. For example, under the control of the imaging control unit 253, the CIS 109 captures an image of the measurement target region 135 irradiated with the red light by the red light irradiation control unit 251 to generate an image data of the captured red image. Furthermore, for example, under the control of the imaging control unit 253, the CIS 109 captures an image of the measurement target region 135 irradiated with the green light by the green light irradiation control unit 252 to generate an image data of the captured green image of the green light (also, referred to as a captured green image).

The redness amount calculation unit 254 performs processing relating to the calculation of the redness amount. The redness amount influence degree calculation unit 255 performs processing relating to the calculation of the redness amount influence degree indicating the magnitude of the influence of the redness amount.

<Flow of Effective AGEs Amount Calculation Process>

Next, an example of a flow of various processes executed by the measurement apparatus 100 in this case will be described. First, an example of a flow of an effective AGEs amount calculation process executed by the control unit 101 will be described with reference to a flowchart of FIG. 23.

If the effective AGEs amount calculation process is started, the AGEs amount calculation processing unit 231 calculates the AGEs amount in step S221. A method of calculating the AGEs amount is arbitrary. For example, the AGEs amount calculation processing unit 231 calculates the AGEs amount by the method described in the first embodiment. That is, the AGEs amount calculation processing unit 231 executes the AGEs amount calculation process described with reference to the flowchart of FIG. 5, for example, and calculates the AGEs amount.

In step S222, the melanin amount influence suppression unit 232 executes a melanin amount influence suppression process and suppresses the influence of the melanin amount. Details of the melanin amount influence suppression process will be described later.

In step S223, the redness amount influence suppression unit 233 executes the redness amount influence suppression process and suppresses the influence of the redness amount. Details of the redness amount influence suppression process will be described later.

In step S224, the AGEs effectiveness degree calculation unit 234 calculates the AGEs effectiveness degree. A method of calculating the AGEs effectiveness degree will be described later.

In step S225, the effective AGEs amount calculation unit 235 calculates the effective AGEs amount. A method of calculating the effective AGEs amount will be described later.

In step S226, the output control unit 156 controls the output unit 122 and the like, for example, to output the effective AGEs amount calculated by the process of step S225.

Upon completion of the process of step S226, the effective AGEs amount calculation process is ended.

<Flow of Melanin Amount Influence Suppression Process>

Next, suppression of the influence on the melanin indicator (AGEs amount) will be described. An example of a flow of the melanin amount influence suppression process executed in step S222 of FIG. 23 will be described with reference to a flowchart of FIG. 24.

If the melanin amount influence suppression process is started, the near-infrared light irradiation control unit 241 of the melanin amount influence suppression unit 232 controls the LED 103 through the LED control unit 102 in step S231 to irradiate the human body 130 with the near-infrared light (wavelength 880 nm light) as irradiation light.

In step S232, the imaging control unit 243 controls the CIS 109 to image the measurement target region 135 irradiated with the near-infrared light. That is, the imaging control unit 243 causes the CIS 109 to receive the reflected light, photoelectrically converts the reflected light, and generates an image data of the captured near-infrared image.

In step S233, the red light irradiation control unit 242 controls the LED 103 through the LED control unit 102 to irradiate the human body 130 with red light (light having a wavelength of 660 nm) as irradiation light.

In step S234, the imaging control unit 243 controls the CIS 109 to image the measurement target region 135 irradiated with the red light. That is, the imaging control unit 243 causes the CIS 109 to receive the reflected light and photoelectrically convert the reflected light to generate an image data of the captured red image.

In step S235, the melanin amount calculation unit 244 executes the melanin amount calculation process to calculate the melanin amount by using the image data of the captured near-infrared image obtained in the process of step S232 and the image data of the captured red image obtained in the process of step S234. Details of the melanin amount calculation process will be described later.

In step S236, the melanin amount influence degree calculation unit 245 calculates the melanin amount influence degree by using the processing result of step S235. A method of calculating the melanin amount influence degree will be described later.

Figure 23:
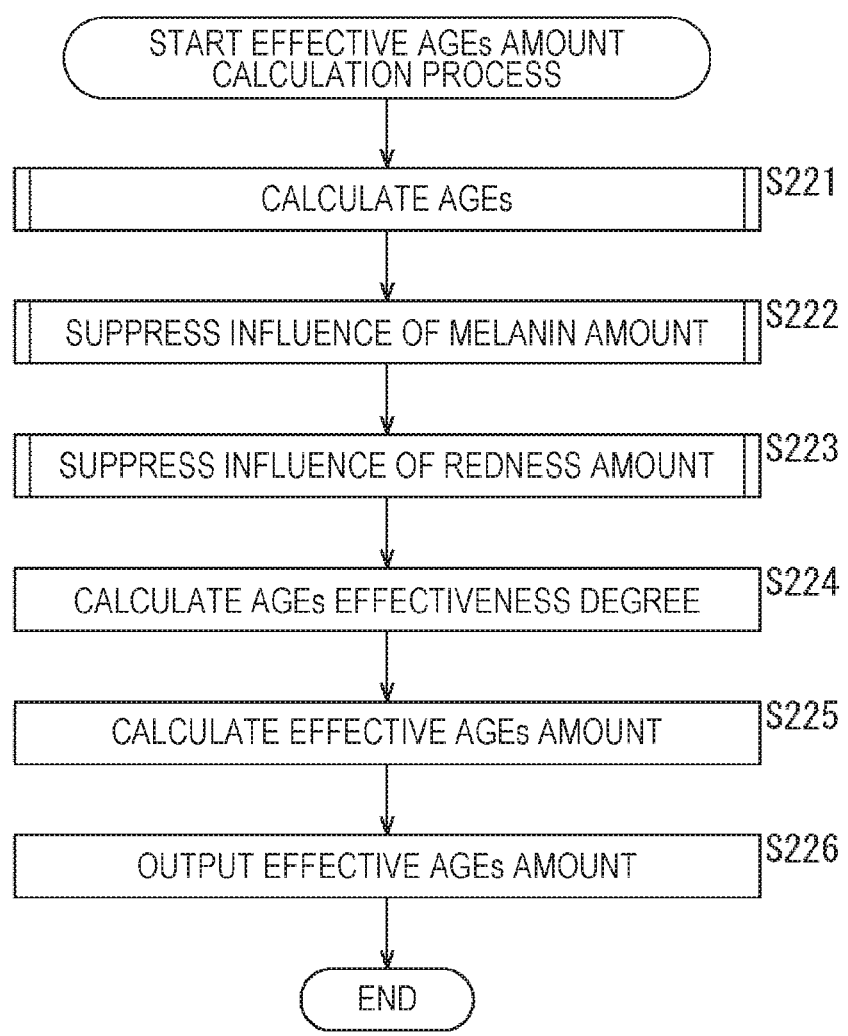
FIG. 23 is a flowchart illustrating an example of a flow of an effective AGEs amount calculation process.

If the melanin amount influence degree is calculated, the melanin amount influence suppression process is ended, and the process returns to FIG. 23.

<Flow of Melanin Amount Calculation Process>

Next, an example of a flow of the melanin amount calculation process executed in step S235 of FIG. 24 will be described with reference to a flowchart of FIG. 25.

If the melanin amount calculation process is started, in step S241, the melanin amount calculation unit 244 calculates a pigment concentration by using the captured near-infrared image and the captured red image. In step S242, the melanin amount calculation unit 244 visualizes the pigment concentration. Upon completion of the process of step S242, the melanin amount calculation process is ended, and the process returns to FIG. 24.

<Calculation of Melanin Amount>

Next, an example of a method of calculating the melanin amount will be described. Although the method of calculating the melanin amount is arbitrary, for example, as described with reference to a flowchart of FIG. 25, the pigment concentration may be calculated as the melanin amount by using the captured near-infrared image and the captured red image. That is, since the light absorption rate for each wavelength differs depending on the substance, the melanin amount is obtained on the basis of the characteristics of the light absorption rate for each wavelength of the melanin pigment.

For example, an example of the light absorption rate (%) (absorption rate distribution) for each wavelength (nm) of melanin pigment, hemoglobin, and collagen as examples of the substance existing in the human body 130 (skin) is illustrated in the graph of FIG. 26. In the graph of FIG. 26, the curve 261 illustrates the absorption rate distribution of the melanin pigment, the curve 262 illustrates the absorption rate distribution of the hemoglobin, and the curve 263 illustrates the absorption rate distribution of the collagen.

As illustrated in the graph of FIG. 26, the difference between the absorption rate of the light having a wavelength of 660 nm and the absorption rate of the light having a wavelength of 880 nm of the melanin pigment is large, but in the case of hemoglobin and collagen, the difference hardly occurs. Therefore, in a case where a difference occurs between the light intensity (log $I_{880}$) at a wavelength of 880 nm and the light intensity (log $I_{660}$) at a wavelength of 660 nm, the main factor of the difference is due to the difference in light absorption rate of melanin (marker 264 and marker 265). That is, by obtaining this difference, the melanin amount can be detected.

Therefore, the melanin amount calculation unit 244 calculates the melanin amount, for example, as expressed in the following Formula (2).

[Mathematical Formula 2]

$$\text{Melanin amount} = \alpha_{MX}(\log I_{880} - \log I_{660}) + \beta_{MX} \quad (2)$$

In Formula (2), $\alpha_{MX}$ and $\beta_{MX}$ are arbitrary coefficients. By obtaining the melanin amount by using the reflected light of two wavelengths in this manner, the melanin amount calculation unit 244 can more easily obtain a more accurate melanin amount. In addition, since the near-infrared light and the red light are detected for each pixel by the CIS 109, the melanin amount calculation unit 244 can calculate the melanin amount (pigment concentration) for each pixel as described above.

<Visualization of Melanin Amount>

The melanin amount calculation unit 244 visualizes the melanin amount (pigment concentration) of each pixel by collecting the melanin amount as an image data. This image data may be displayed, for example, on the monitor of the output unit 122 by the output control unit 156.

Figure 27B:
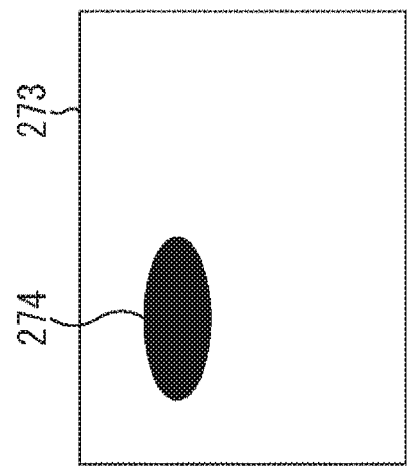
FIGS. 27A and 27B are diagrams illustrating an example of an analysis result of melanin.
Figure 27A:
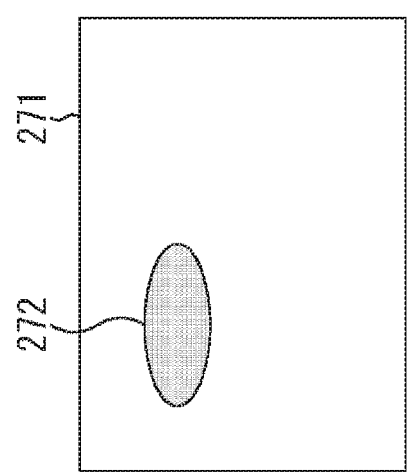

FIGS. 27A and 27B illustrate an example of a state of the image. As illustrated in FIG. 27A, in the case of the normal visible light image 271, there is a possibility that, when the deposition amount of the melanin pigment is small, the stain 272 has a non-dense color and becomes inconspicuous due to mixing with the skin color or the like. That is, it is difficult to grasp accurately the distribution state of the melanin from the normal visible light image 271. In other words, it is difficult to obtain an accurate melanin amount from this image data of visible light.

On the contrary, as illustrated in FIG. 27B, in the case of the image 273 obtained by converting the melanin amount obtained as described above into an image as a pixel value, since the change in pixel value due to other than the melanin pigment is suppressed, the stain 274 can be visually recognized more clearly. That is, the distribution of melanin can be more clearly represented in the image 273 than in the image 271, and thus, the distribution state of melanin can be more easily grasped.

As described above, the melanin amount calculation unit 244 may obtain the melanin amount for each pixel. In addition, the melanin amount calculation unit 244 may obtain the melanin amount for each partial region including a plurality of pixels. For example, the melanin amount calculation unit 244 may obtain statistical values (for example, a total value, an average value, and the like) for each partial region of the melanin amount for each pixel. In addition, the melanin amount calculation unit 244 may obtain the melanin amount for the entire image (the entire pixel region). For example, the melanin amount calculation unit 244 may obtain statistical values (for example, a total value, an average value, and the like) for the entire image of the melanin amount for each pixel. Furthermore, the melanin amount calculation unit 244 may obtain the melanin amount for a part of the image (pixel region).

In addition, the output control unit 156 may cause the data (for example, the above-described image data and statistical values) of the melanin amount (pigment concentration) generated by the melanin amount calculation unit 244 to be stored in the storage unit 123, may cause the data to be written in the removable medium 126, or may cause the data to be supplied to another apparatus through the output unit 122 or the communication unit 124.

<Melanin Amount Influence Degree>

Figure 24:
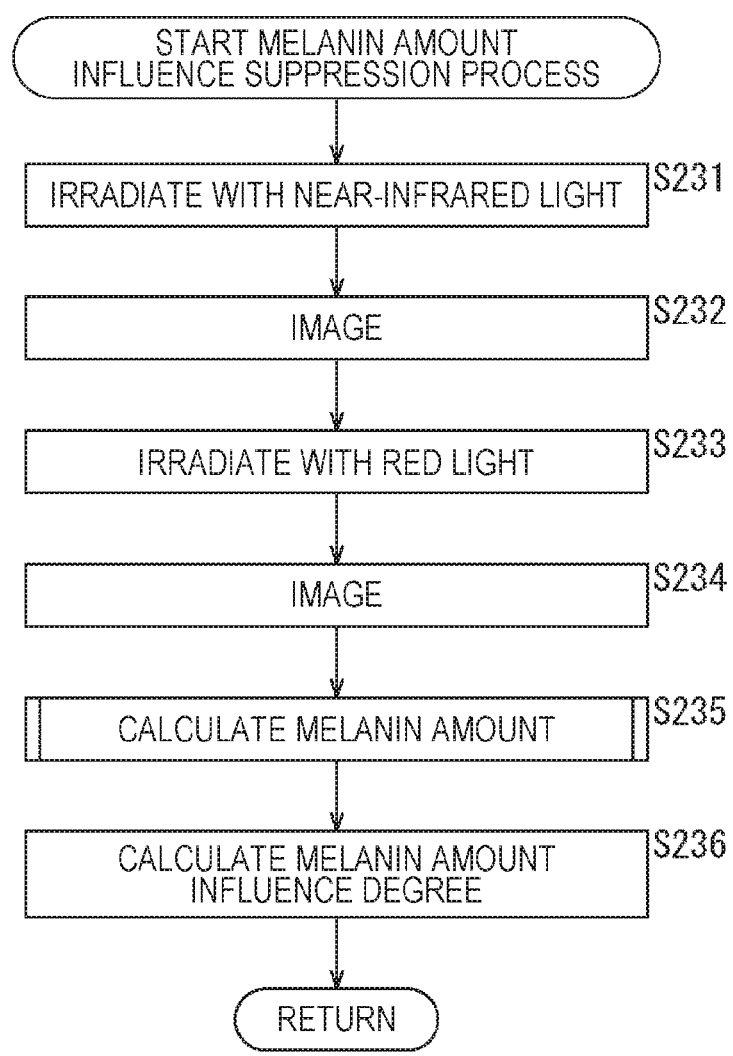
FIG. 24 is a flowchart illustrating an example of a flow of a melanin amount influence suppression process.
Figure 25:
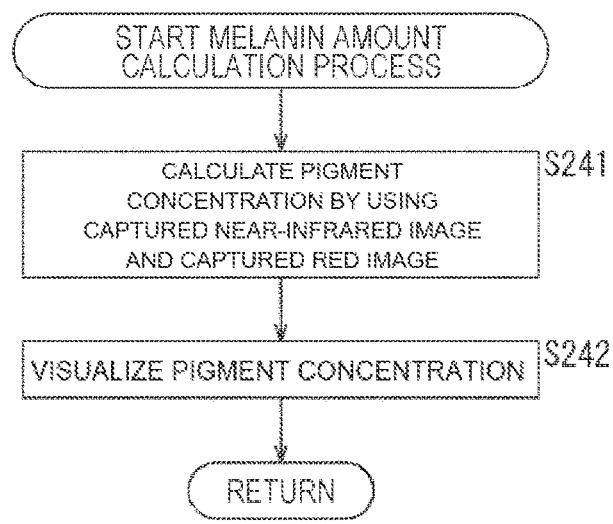
FIG. 25 is a flowchart illustrating an example of a flow of a melanin amount calculation process.

In step S236 of FIG. 24, the melanin amount influence degree calculation unit 245 calculates the melanin amount influence degree (Melanin influence degree, which is a parameter indicating the magnitude of the influence of the melanin amount on the AGEs amount, by using the melanin amount calculated. A method of calculating the melanin amount influence degree is arbitrary. For example, the melanin amount influence degree calculation unit 245 may calculate the melanin amount influence degree as expressed in the following Formula (3).

[Mathematical Formula 3]

$$\alpha_M = \begin{cases} 0: & \text{When } M < M_{min} \\ \dfrac{M - M_{min}}{M_{max} - M_{min}}: & \text{When } M_{min} \le M \le M_{max} \\ 1: & M > M_{max} \end{cases} \quad (3)$$

In Formula (3), $\alpha_M$ represents the melanin amount influence degree. In addition, M represents the melanin amount. $M_{min}$ indicates the minimum value of the melanin amount M in the range where the melanin amount influence degree $\alpha_M$ varies, and $M_{max}$ indicates the maximum value of the melanin amount M in the range where the melanin amount influence degree $\alpha_M$ varies. That is, the relationship between the melanin amount M and the melanin amount influence degree $\alpha_M$ is, for example, the curve 281 of the graph illustrated in FIG. 28.

As described in detail later, this melanin amount influence degree $\alpha_M$ is used for calculating the AGEs effectiveness degree. The melanin amount influence suppression unit 232 obtains the melanin amount influence degree in this manner, and thus, the measurement apparatus 100 can suppress the influence of the melanin amount on the AGEs amount.

In addition, the melanin amount influence degree calculation unit 245 may obtain such a melanin amount influence degree $\alpha_M$ for each pixel, may obtain the melanin amount influence degree for each partial region including a plurality of pixels, may obtain the melanin amount influence degree for the entire image (the entire pixel region), or may obtain the melanin amount influence degree for a part of the image (pixel region). Furthermore, the output control unit 156 may cause the data of the melanin amount influence degree $\alpha_M$ obtained by the melanin amount influence degree calculation unit 245 to be displayed on the monitor of the output unit 122, may cause the data to be stored in the storage unit 123, may cause the data to be written in the removable medium 126, or may cause the data to be supplied to another apparatus through the output unit 122 or the communication unit 124.

<Flow of Redness Amount Influence Suppression Process>

Next, suppression of the influence of the redness on the indicator (AGEs amount) will be described. An example of a flow of the redness amount influence suppression process executed in step S223 of FIG. 23 will be described with reference to a flowchart of FIG. 29.

If the redness amount influence suppression process is started, in step S251, the red light irradiation control unit 251 of the redness amount influence suppression unit 233 controls the LED 103 through the LED control unit 102 to irradiate the human body 130 with red light (light with a wavelength of 660 nm) as irradiation light.

In step S252, the imaging control unit 253 controls the CIS 109 to image the measurement target region 135 irradiated with the red light. That is, the imaging control unit 253 causes the CIS 109 to receive the reflected light and photoelectrically convert the reflected light to generate an image data of the captured red image. In addition, the image data of the captured red image (the image data of the captured red image generated in the process of step S234 in FIG. 24) generated during the process for suppressing the influence of the melanin amount may also be used for the process for suppressing the influence of the redness amount. In this case, the processes of steps S251 and S252 may be omitted.

In step S253, the green light irradiation control unit 252 controls the LED 103 through the LED control unit 102 to irradiate the human body 130 with green light (light having a wavelength of 570 nm) as irradiation light.

In step S254, the imaging control unit 253 controls the CIS 109 to image the measurement target region 135 irradiated with the green light. That is, the imaging control unit 253 causes the CIS 109 to receive the reflected light and photoelectrically convert the reflected light to generate an image data of the captured green image.

In step S255, the redness amount calculation unit 254 executes the redness amount calculation process to calculate the redness amount by using the image data of the captured red image obtained in the process of step S252 and the image data of the captured green image obtained in the process of step S254. Details of the redness amount calculation process will be described later.

In step S256, the redness amount influence degree calculation unit 255 calculates the redness amount influence degree by using the processing result of step S255. A method of calculating the redness amount influence degree will be described later.

If the redness amount influence degree is calculated, the redness amount influence suppression process is ended, and the process returns to FIG. 23.

<Flow of Redness Amount Calculation Process>

Next, an example of a flow of the redness amount calculation process executed in step S255 of FIG. 29 will be described with reference to a flowchart of FIG. 30.

If the redness amount calculation process is started, in step S261, the redness amount calculation unit 254 calculates the pigment concentration by using the captured red image and the captured green image. In step S262, the redness amount calculation unit 254 visualizes the pigment concentration. Upon completion of the process of step S262, the redness amount calculation process is ended, and the process returns to FIG. 29.

<Calculation of Redness Amount>

Next, an example of a method of calculating redness amount will be described. Although the method of calculating the redness amount is arbitrary, for example, as described with reference to a flowchart of FIG. 30, the pigment concentration may be calculated as the redness amount by using the captured red image and the captured green image. That is, since the light absorption rate for each wavelength differs depending on the substance, the redness amount is obtained on the basis of the characteristics of the light absorption rate for each wavelength of hemoglobin which is the main factor of redness.

For example, as illustrated in the graph of FIG. 26, the difference between the absorption rate of the light having a wavelength of 570 nm and the absorption rate of the light having a wavelength of 660 nm of hemoglobin is much larger than that of melanin pigment or collagen. Therefore, in a case where a difference occurs between the light intensity ($\log I_{660}$) at a wavelength of 660 nm and the light intensity ($\log I_{570}$) at a wavelength of 570 nm, the main factor of the difference is due to the difference in light absorption rate of hemoglobin (marker 266 and marker 267). That is, by obtaining this difference, the redness amount can be detected.

Therefore, the redness amount calculation unit 254 calculates the redness amount, for example, as expressed in the following Formula (4).

[Mathematical Formula 4]

$$\text{Redness amount} = \alpha_{EX}(\log I_{660} - \log I_{570}) + \beta_{EX} \quad (4)$$

In Formula (4), $\alpha_{EX}$ and $\beta_{EX}$ are arbitrary coefficients. By obtaining the redness amount by using the reflected light of two wavelengths in this manner, the redness amount calculation unit 254 can more easily obtain a more accurate redness amount. In addition, since the red light and the green light are detected for each pixel by the CIS 109, the redness amount calculation unit 254 can calculate the redness amount (pigment concentration) for each pixel as described above.

<Visualization of Redness Amount>

The redness amount calculation unit 254 visualizes the redness amount (pigment concentration) of each pixel by collecting the redness amount as image data. This image data may be displayed, for example, on the monitor of the output unit 122 by the output control unit 156.

Figure 31B:
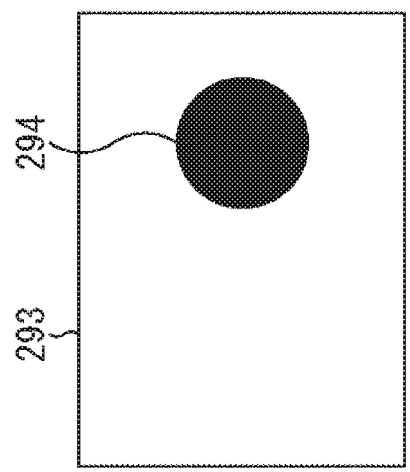
FIGS. 31A and 31B are diagrams illustrating an example of an analysis result of redness.
Figure 31A:
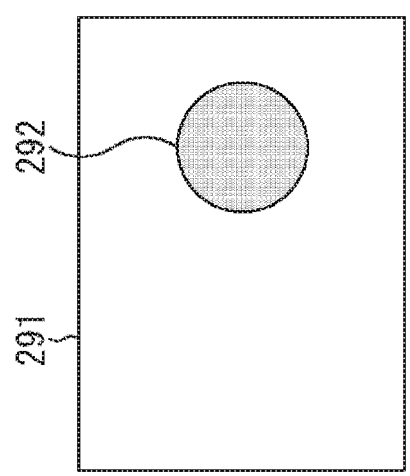

FIGS. 31A and 31B illustrate an example of a state of the image. As illustrated in FIG. 31A, in the case of the normal visible light image 291, there is a possibility that, when the amount of hemoglobin generated is small, the redness 292 has a non-dense color and becomes inconspicuous due to mixing with the skin color or the like. That is, it is difficult to grasp the accurate distribution state of redness (hemoglobin) from the normal visible light image 291. In other words, it is difficult to obtain an accurate redness amount from this image data of visible light.

On the contrary, as illustrated in FIG. 31B, in the case of the image 293 obtained by converting the redness amount obtained as described above into an image as a pixel value, since the change in pixel value due to other than the hemoglobin is suppressed, so the redness 294 can be visually recognized more clearly. That is, the distribution of redness (hemoglobin) can be more clearly represented in the image 293 than in the image 291, and thus, the distribution state of redness (hemoglobin) can be more easily grasped.

As described above, the redness amount calculation unit 254 can obtain the redness amount for each pixel. In addition, the redness amount calculation unit 254 may obtain the redness amount for each partial region including a plurality of pixels. For example, the redness amount calculation unit 254 may obtain statistical values (for example, a total value, an average value, and the like) for each partial region of the redness amount for each pixel. Furthermore, the redness amount calculation unit 254 may obtain the redness amount for the entire image (the entire pixel region). For example, the redness amount calculation unit 254 may obtain statistical values (for example, a total value, an average value, and the like) for the entire image of redness amount for each pixel. Furthermore, the redness amount calculation unit 254 may obtain the redness amount for a part of the image (pixel region).

In addition, the output control unit 156 may cause the data (for example, the above-described image data and statistical values) of the redness amount (pigment concentration) generated by the redness amount calculation unit 254 to be stored in the storage unit 123, may cause the data to be written in the removable medium 126, or may cause the data to be supplied to another apparatus through the output unit 122 or the communication unit 124.

<Redness Influence Degree>

Figure 29:
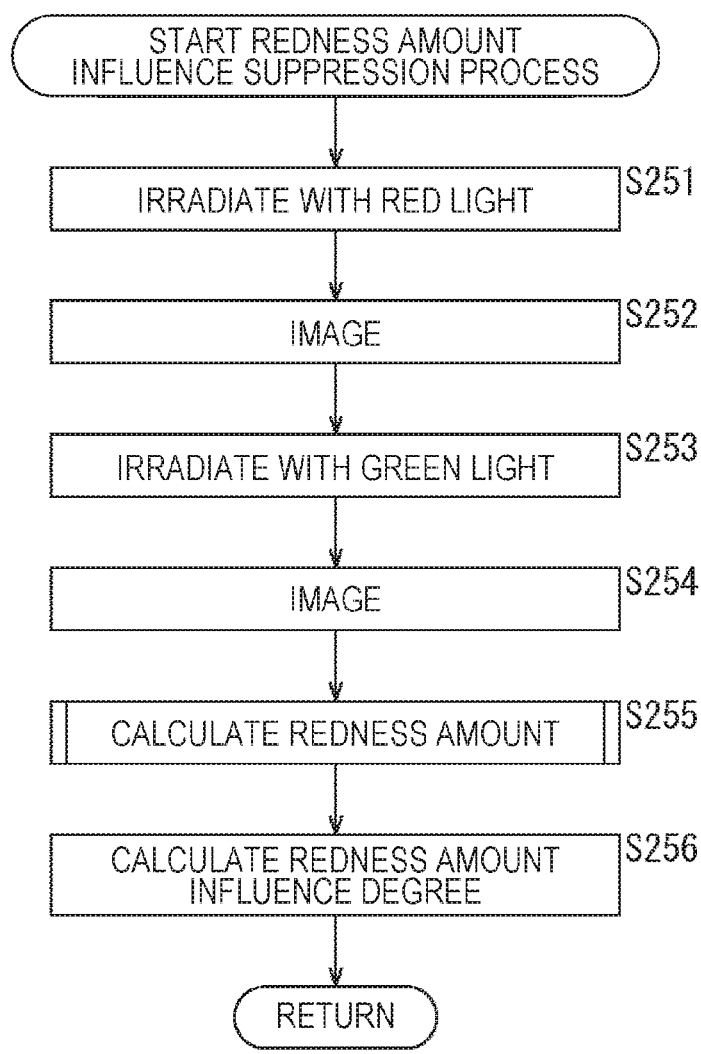
FIG. 29 is a flowchart illustrating an example of a flow of a redness amount influence suppression process.
Figure 30:
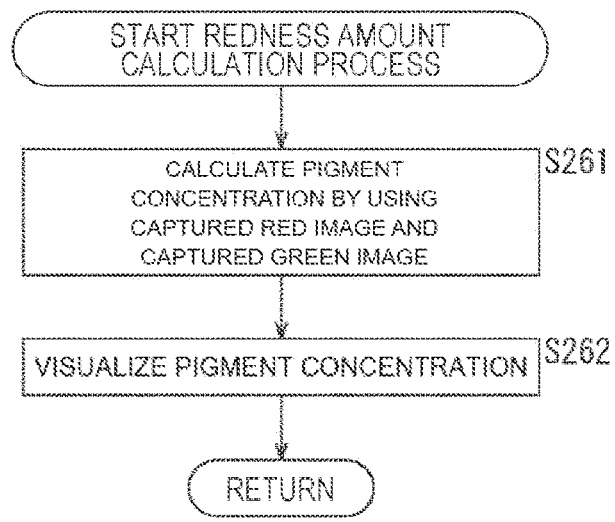
FIG. 30 is a flowchart illustrating an example of a flow of a redness amount calculation process.

In step S256 of FIG. 29, the redness amount influence degree calculation unit 255 calculates the redness amount influence degree, which is a parameter indicating the magnitude of the influence of the redness amount on the AGES amount, by using the redness amount calculated as described above. A method of calculating the redness amount influence degree is arbitrary. For example, the redness amount influence degree calculation unit 255 may calculate the redness amount influence degree as expressed in the following Formula (5).

[Mathematical Formula 5]

$$\alpha_E = \begin{cases} 0: & \text{When } E < E_{min} \\ \dfrac{E - E_{min}}{E_{max} - E_{min}}: & \text{When } E_{min} \le E \le E_{max} \\ 1: & E > E_{max} \end{cases} \quad (5)$$

Figure 32:
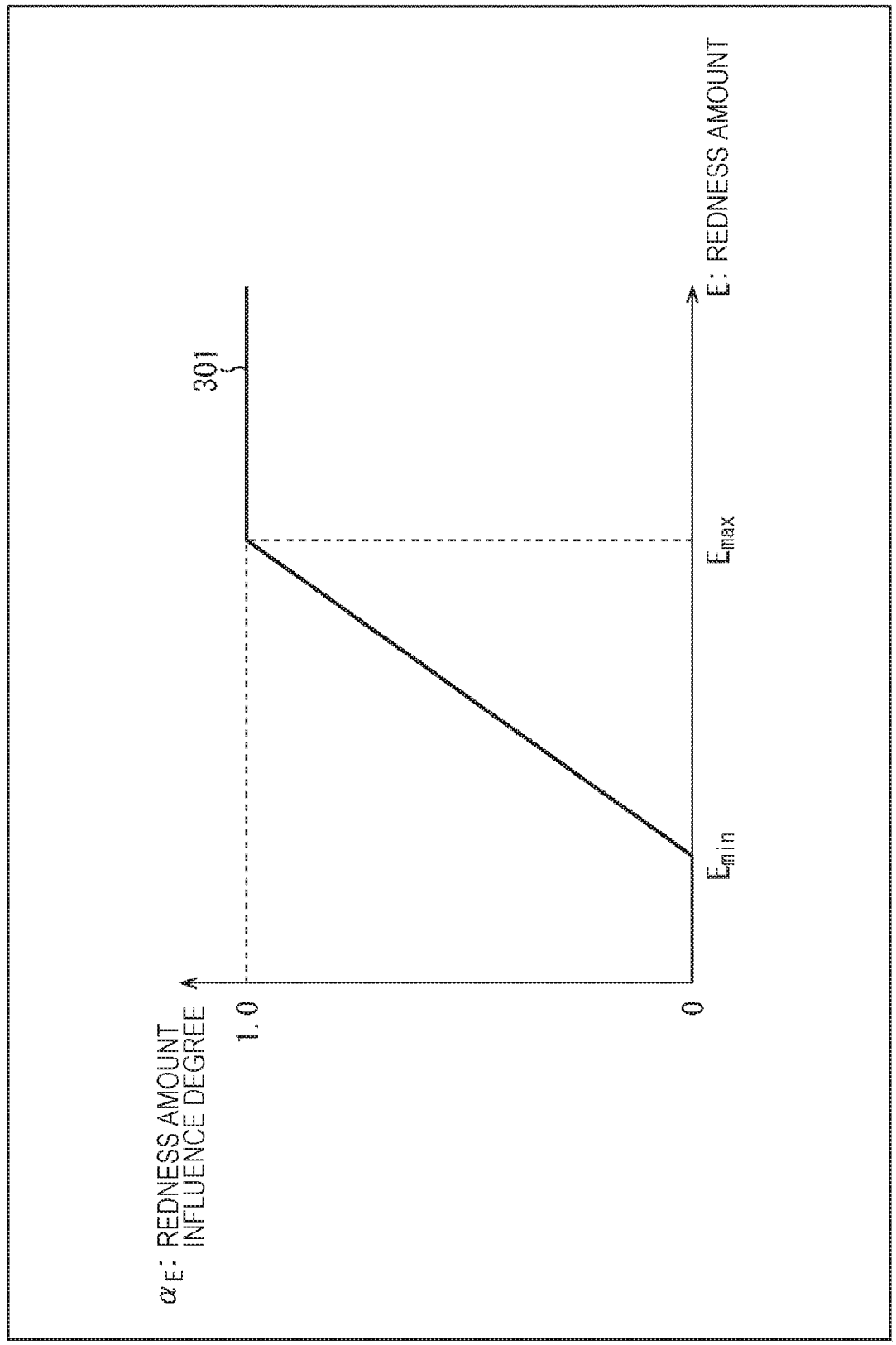
FIG. 32 is a diagram illustrating an example of calculation of a redness amount influence degree.

In Formula (5), $\alpha_E$ represents the degree of redness influence. In addition, E represents the redness amount. $E_{min}$ indicates the minimum value of the redness amount E in the range where the redness amount influence degree $\alpha_E$ varies, and $E_{max}$ indicates the maximum value of the redness amount E in the range in which the redness amount influence degree $\alpha_E$ varies. That is, the relationship between the redness amount E and the degree of redness influence degree $\alpha_E$ is, for example, the curve 301 of the graph illustrated in FIG. 32.

Although details will be described later, the redness amount influence degree $\alpha_E$ is used for calculating the AGEs effectiveness degree. The redness amount influence suppression unit 233 obtains the redness amount influence degree in this manner, and thus, the measurement apparatus 100 can suppress the influence of the redness amount on the AGEs amount.

In addition, the redness amount influence degree calculation unit 255 may obtain such a redness amount influence degree $\alpha_E$ for each pixel, may obtain the redness amount influence degree for each partial region including a plurality of pixels, may obtain the redness amount influence degree for the entire image (the entire pixel region), or may obtain the redness amount influence degree for apart of the image (pixel region). Furthermore, the output control unit 156 may cause the data of the melanin amount influence degree $\alpha_E$ obtained by the redness amount influence degree calculation unit 255 to be displayed on the monitor of the output unit 122, may cause the data to be stored in the storage unit 123, may cause the data to be written in the removable medium 126, or may cause the data to be supplied to another apparatus through the output unit 122 or the communication unit 124.

<AGEs Effectiveness Degree>

Next, the AGEs effectiveness degree will be described. As described above, the AGEs effectiveness degree calculation unit 234 calculates the AGEs effectiveness degree indicating the magnitude of the influence of the error factors (for example, melanin and redness) on the AGEs amount in step S224 of FIG. 23. A method of calculating the AGEs effectiveness degree is arbitrary. For example, the AGEs effectiveness degree calculation unit 234 may calculate the AGEs effectiveness degree by using the melanin amount influence degree $\alpha_M$ obtained by the process (melanin amount influence suppression process) of step S222 of FIG. 23 and the redness amount influence degree $\alpha_E$ obtained by the process (redness amount influence suppression process) of step S223 of FIG. 23, as expressed in the following Formula (6).

[Mathematical Formula 6]

$$\alpha_{AGE} = \begin{cases} 1.0 & (0 \le \gamma < \alpha) \\ \dfrac{\alpha_1 - \gamma}{\alpha_1 - \alpha_0} & (\alpha_0 \le \gamma \le \alpha_1) \\ 0.0 & (\gamma \ge \alpha_1) \end{cases} \quad (6)$$

Figure 33:
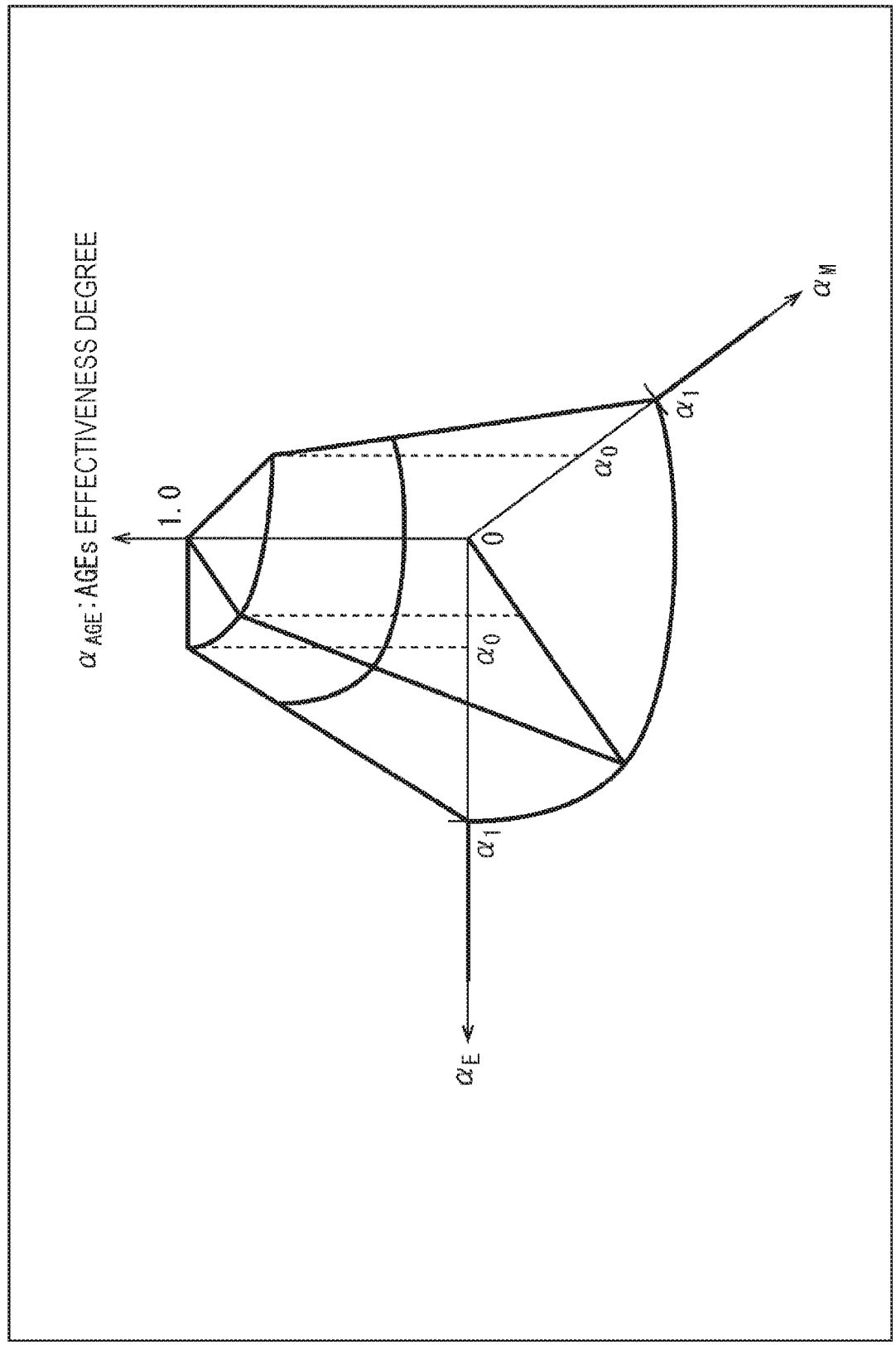
FIG. 33 is a diagram illustrating an example of a state of calculation of the AGEs effectiveness degree.

Herein, $\gamma = \sqrt{\alpha_M^2 + \alpha_E^2}$ $0 \le \alpha_0 \le \alpha_1 \le 1$ In Formula (6), $\alpha_{AGE}$ indicates the AGEs effectiveness degree. In addition, $\gamma$ is a coefficient obtained from the melanin amount influence degree $\alpha_M$ and the redness amount influence degree $\alpha_E$. In addition, $\alpha_0$ and $\alpha_1$ are arbitrary coefficients set under the condition as expressed in Formula (6). That is, the relationship between the AGEs effectiveness degree $\alpha_{AGE}$ and the melanin amount influence degree $\alpha_M$, and the relationship between the AGEs effectiveness degree $\alpha_{AGE}$ and the redness amount influence degree $\alpha_E$ are like, for example, the graph illustrated in FIG. 33.

In addition, the AGEs effectiveness degree calculation unit 234 may obtain such an AGEs effectiveness degree $\alpha_{AGE}$ for each pixel, may obtain the AGEs effectiveness degree for each partial region including a plurality of pixels, may obtain the AGEs effectiveness degree for the entire image (the entire pixel region), or may obtain the AGEs effectiveness degree for a part of the image (pixel region). In addition, the output control unit 156 may cause the data of the AGEs effectiveness degree $\alpha_{AGE}$ obtained by the AGEs effectiveness degree calculation unit 234 to be displayed on the monitor of the output unit 122, may cause the data to be stored in the storage unit 123, may cause the data to be written in the removable medium 126, or may cause the data to be supplied to another apparatus through the output unit 122 or the communication unit 124.

<Effective AGEs Amount>

Next, the effective AGEs amount will be described. As described above, in step S225 of FIG. 23, the effective AGEs amount calculation unit 235 calculates the effective AGEs amount obtained by correcting (updating) the AGEs amount on the basis of the error factors. A method of calculating the effective AGEs amount is arbitrary. For example, the effective AGEs amount calculation unit 235 may calculate the effective AGEs amount by using the AGEs effectiveness degree $\alpha_{AGE}$ obtained by the process of step S225 of FIG. 23 as expressed in the following Formula (7).

[Mathematical Formula 7]

$$AGE_{eff} = \alpha_{AGE} \cdot AGE \qquad (7)$$

In Formula (7), $AGE_{eff}$ indicates the effective AGEs amount. In addition, the AGE indicates the AGEs amount obtained by the process (AGEs amount calculation process) of step S221 of FIG. 23. In this manner, since the effective AGEs amount calculation unit 235 corrects the AGEs amount calculated by the AGEs amount calculation processing unit 231 by using the AGEs effectiveness degree $\alpha_{AGE}$ calculated by the AGEs effectiveness degree calculation unit 234, the measurement apparatus 100 can obtain a more accurate AGEs amount (effective AGEs amount $AGE_{eff}$) than that in the case of suppressing the influence of the error factor. In addition, since the measurement apparatus 100 receives the reflected light by using the CIS, it is possible to correct the AGEs amount without requiring complicated operations such as shifting the position and re-measuring. That is, the measurement apparatus 100 can more easily obtain an accurate AGEs amount.

In addition, the effective AGEs amount calculation unit 235 may obtain such an effective AGEs amount $AGE_{eff}$ for each pixel, may obtain the effective AGEs amount for each partial region including a plurality of pixels, may obtain the effective AGEs amount for the entire image (the entire pixel region), or may obtain the effective AGEs amount for apart of the image (pixel region). In addition, the output control unit 156 may cause the data of the effective AGEs amount $AGE_{eff}$ obtained by the effective AGEs amount calculation unit 235 to be displayed on the monitor of the output unit 122, may cause the data to be store in the storage unit 123, may cause the data to be written in the removable medium 126, or may cause the data to be supplied to another apparatus through the output unit 122 or the communication unit 124.

By executing each process and correcting the indicator value as described above, the measurement apparatus 100 can output a more accurate indicator value (AGEs amount).

<Irradiated Light/Reflected Light>

In addition, the wavelength of the irradiation light irradiated in the melanin amount influence suppression process (FIG. 24), the redness amount influence polarity process (FIG. 29), and the like according to the present embodiment is arbitrary as long as the wavelength of the irradiation light can be used to suppress the influence of the error factor on the indicator value and is not limited to the above example. In addition, the number of wavelengths of the irradiation light is likewise arbitrary, and the number of wavelengths is not limited to the above-described two wavelengths but may be three or more wavelengths. In other words, the wavelength of the reflected light received by the CIS 109 and the number of wavelengths thereof are arbitrary as long as the wavelength of the reflected light and the number of wavelengths thereof can be used to suppress the influence of the error factor on the indicator value and are not limited to the above example.

For example, the LED 103 may emit white light. In this case, a filter that transmits each wavelength light (in the above example, near-infrared light, red light, and green light) to be imaged in the CIS 109 is provided immediately after the LED 103, and the irradiation light can be separated in terms of wavelength by each filter so as to irradiate the human body 130. With such a configuration, it is not necessary to switch the wavelength of the irradiation light, and it is possible to generate images of a plurality of wavelengths by one irradiation. That is, it is possible to more easily generate images of a plurality of wavelengths. Additionally, since the near-ultraviolet light can also be extracted by using a filter in a similar manner, the white light is set as the irradiation light, so that the irradiation light can also be used for calculation of the AGEs amount.

In addition, in order to suppress the influence of the error factor on the indicator value, an LED that irradiates the irradiation light may be provided separately from the LED 103. In addition, an LED may be provided for each wavelength of the irradiation light.

In addition, in order to suppress the influence of the error factor on the indicator value, the CISs, the lenses, the filters, and the like for generating the image data may be provided separately from the CISs (for example, the CIS 105 and the CIS 109) used for calculating the AGEs amount, the lenses (for example, the lens 106 and the lens 110), the filters (for example, the filter 107 and the filter 111), and the like.

In addition, in the case of generating the image data for light having a plurality of wavelengths, a CIS, a lens, a filter, and the like may be provided for each wavelength. For example, in the case of generating each image data of a captured near-infrared image, a captured red image, and a captured green image, a filter and a lens that transmit near-infrared light (wavelength 880 nm), a CIS that receives and photoelectrically converts the near-infrared light, a filter and a lens that transmit red light (wavelength 660 nm), a CIS that receives and photoelectrically converts the red light, and a filter and a lens that transmit green light (wavelength 570 nm), a CIS that receives and photoelectrically converts the green light may be provided.

Furthermore, by switching the filters provided in front of the CIS, light of a plurality of wavelengths may be received in one CIS. For example, in the case of generating the image data of a captured near-infrared image, a filter that transmits near-infrared light (wavelength 880 nm) may be set; in the case of generating the image data of a captured red image, a filter that transmits red light (wavelength 660 nm) may be set; and in the case of generating the image data of a captured green image, a filter that transmits green light (wavelength 570 nm) may be set. In this case, it is possible to reduce the number of CISs as compared with a case where the CIS is provided for each wavelength, and it is possible to suppress an increase in cost and size of the casing. However, a configuration for switching filters is required. Furthermore, in the case of using a plurality of the CISs, it is possible to generate the image data at a higher speed.

In addition, since the filters are allowed to be switched, it is also possible to switch the filter 107, so that it is also possible to use the CIS 105 for generation of the image data in order to suppress the influence of the error factor on the indicator value. Additionally, both the CIS 105 and the CIS 109 can be used. For example, it is possible to generate the image data of a captured near-infrared image in the CIS 105 and to generate the image data of a captured red image in the CIS 109 concurrently therewith. Therefore, it is possible to generate the image data of light of plural wavelengths at a higher speed. That is, it is possible to correct the AGEs amount more quickly.

In addition, the reflected light of the same wavelength may be allowed to be received by a plurality of CISs.

4. Third Embodiment

<Output Control of AGEs Amount>

In the second embodiment, the AGEs effectiveness degree indicating the magnitude of the influence on the indicator value (AGEs amount) due to the error factors (for example, melanin and redness) is calculated, and the indicator value (AGEs amount) is corrected by using the AGEs effectiveness degree. Instead of correcting the indicator value (AGEs amount), the AGEs effectiveness degree may be used for output control of the indicator value (AGEs amount).

For example, in a case where the AGEs effectiveness degree is not sufficiently high, it may be determined that the reliability of the indicator value (AGEs amount) is low, and the indicator value (AGEs amount) may not be output. In other words, the indicator value (AGEs amount) may be output only in a case where the AGEs effectiveness degree is sufficiently high. In this manner, by controlling the output of the indicator value on the basis of a predetermined error factor, the measurement apparatus 100 can output a more accurate indicator value (AGEs amount).

<Control Unit>

Figure 34:
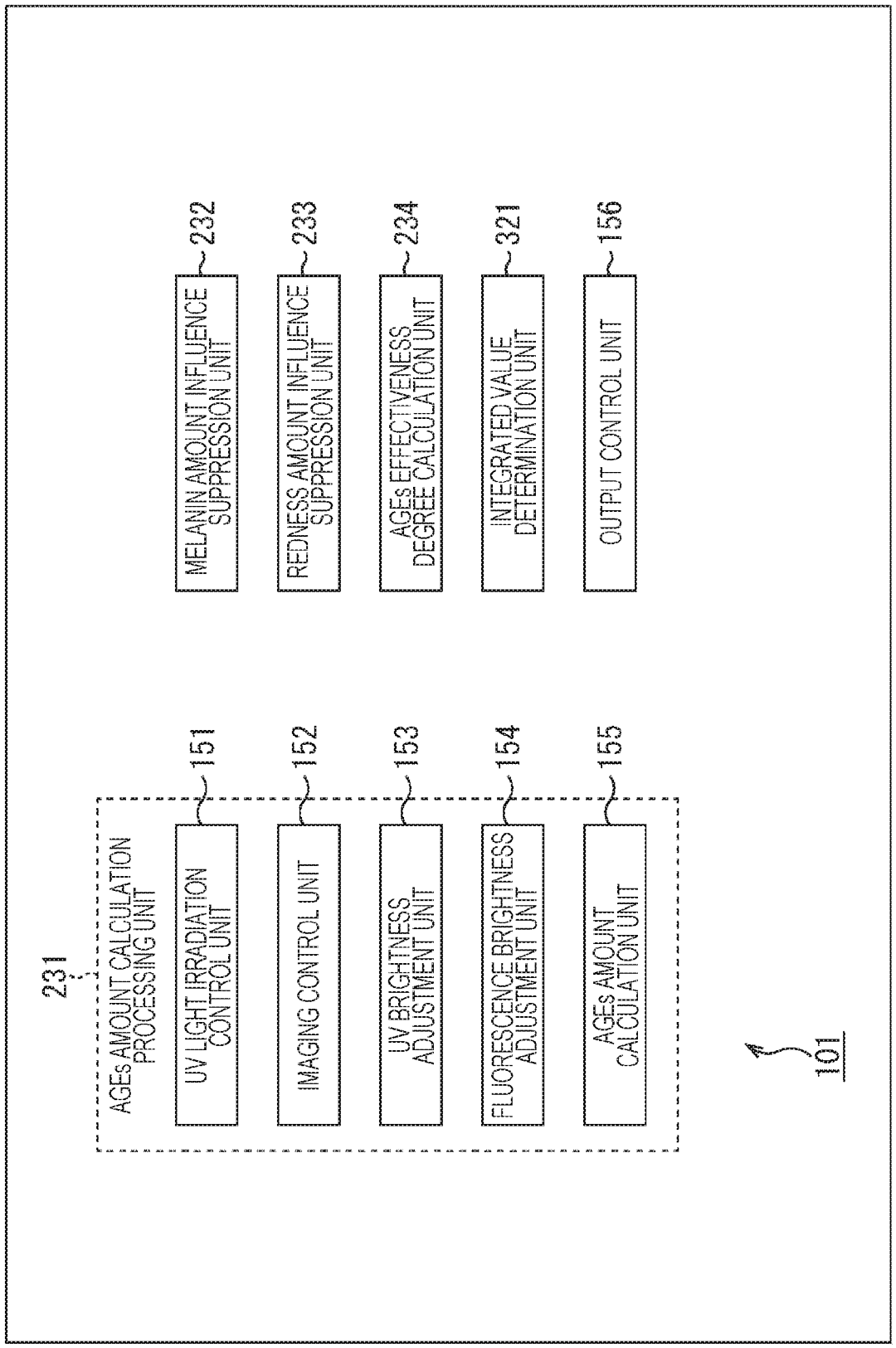
FIG. 34 is a functional block diagram illustrating functions realized by a control unit.

FIG. 34 is a functional block diagram illustrating an example of main functions realized by the control unit 101 in this case by executing a program and the like. As illustrated in FIG. 34, in this case, by executing the program, the control unit 101 can have functions of, for example, the AGEs amount calculation processing unit 231 to the AGEs effectiveness degree calculation unit 234, the integrated value determination unit 321, and the output control unit 156.

The integrated value determination unit 321 integrates the AGEs effectiveness degree generated by the AGEs effectiveness degree calculation unit 234 in the image and determines the magnitude of the integrated value.

<Flow of AGEs Amount Calculation Process>

Figure 35:
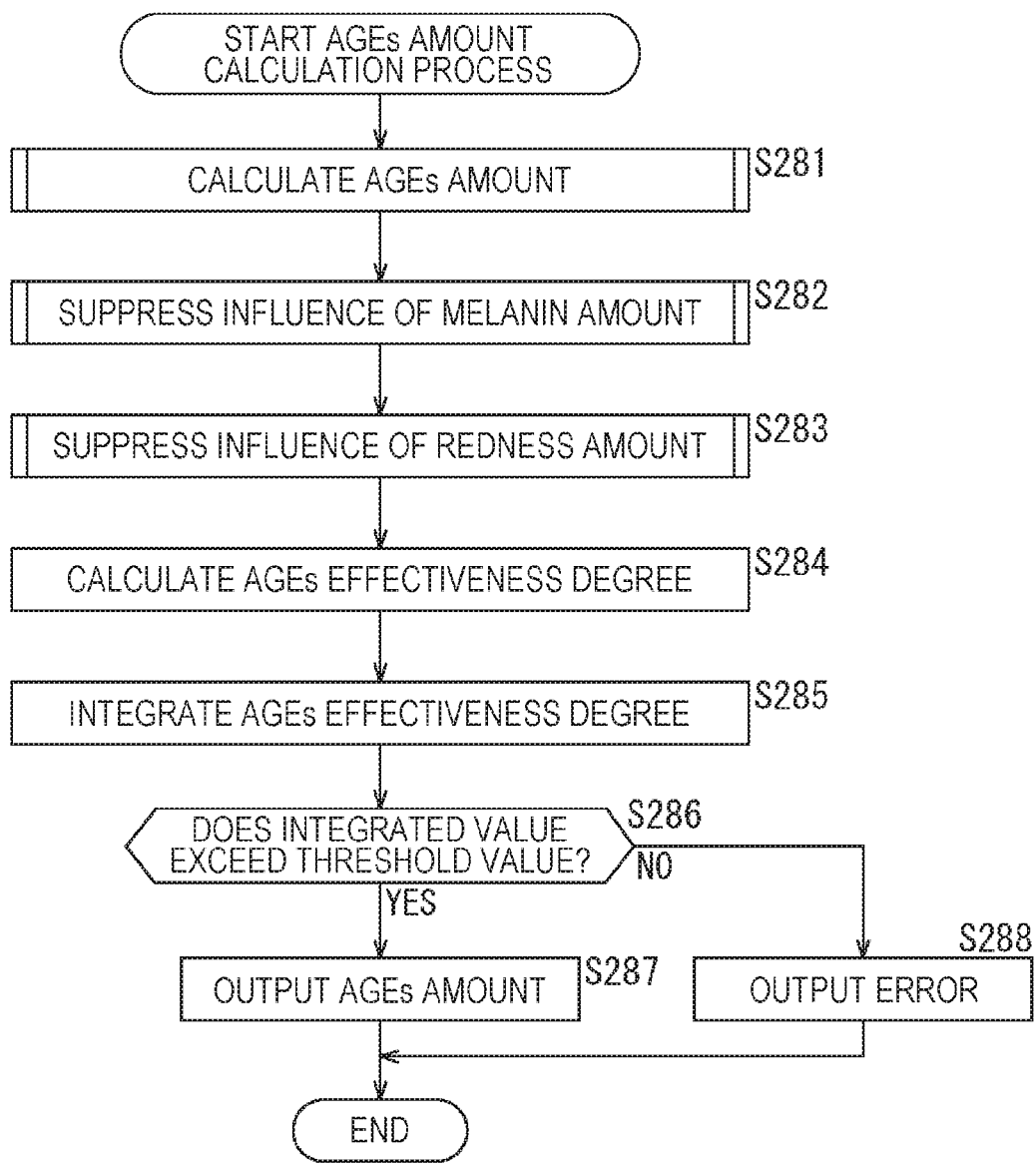
FIG. 35 is a flowchart illustrating an example of a flow of an AGEs amount calculation process.

Next, an example of a flow of various processes executed by the measurement apparatus 100 in this case will be described. First, an example of a flow of the AGEs amount calculation process executed by the control unit 101 will be described with reference to a flowchart of FIG. 35.

If the AGEs amount calculation process is started, the AGEs amount calculation processing unit 231 to the AGEs effectiveness degree calculation unit 234 execute the processes of steps S281 to S284 in a manner similar to those of the processes of steps S221 to S224 of FIG. 23. That is, the AGEs amount and the AGEs effectiveness degree are calculated.

In step S285, the integrated value determination unit 321 integrates the AGEs effectiveness degree calculated in step S224. For example, the AGEs effectiveness degree calculation unit 234 calculates the AGEs effectiveness degree for each pixel, for each partial region, over the entire image, or for a portion of the image. The integrated value determination unit 321 integrates the AGEs effectiveness degree in the image every time the AGEs effectiveness degree is calculated.

In step S286, the integrated value determination unit 321 determines whether or not the integrated value of the AGEs effectiveness degree calculated in step S285 exceeds a predetermined threshold value. In addition, the magnitude of this threshold value is arbitrary. In a case where it is determined that the integrated value is larger than the threshold value, the process proceeds to step S287.

In step S287, the output control unit 156 outputs the AGEs amount calculated in step S281. For example, the output control unit 156 may cause the AGEs amount to be displayed on the monitor of the output unit 122, may cause the AGEs amount to be stored in the storage unit 123, may cause the AGEs amount to be written in the removable medium 126, or may cause the AGEs amount to be supplied to another apparatus through the output unit 122 or the communication unit 124.

Upon completion of the process of step S287, the AGEs amount calculation process is ended.

In addition, in a case where it is determined in step S286 that the integrated value is equal to or smaller than the threshold value, the process proceeds to step S288. In this case, the reliability of the AGEs amount calculated in step S281 is low (not sufficiently high). Therefore, in step S288, the output control unit 156 outputs an error without outputting the AGEs amount.

Upon completion of the process of step S288, the AGEs amount calculation process is ended.

By controlling the output as described above, the measurement apparatus 100 can output a more accurate indicator value (AGEs amount).

5. Application Example

<Configuration of Measurement Apparatus>

The configuration of the measurement apparatus 100 is not limited to the example of FIG. 3. For example, the first reflected light and the second reflected light may be received by one CIS. For example, a pixel region for receiving the first reflected light and a pixel region for receiving the second reflected light may be provided in the pixel region of one CIS.

Figure 36:
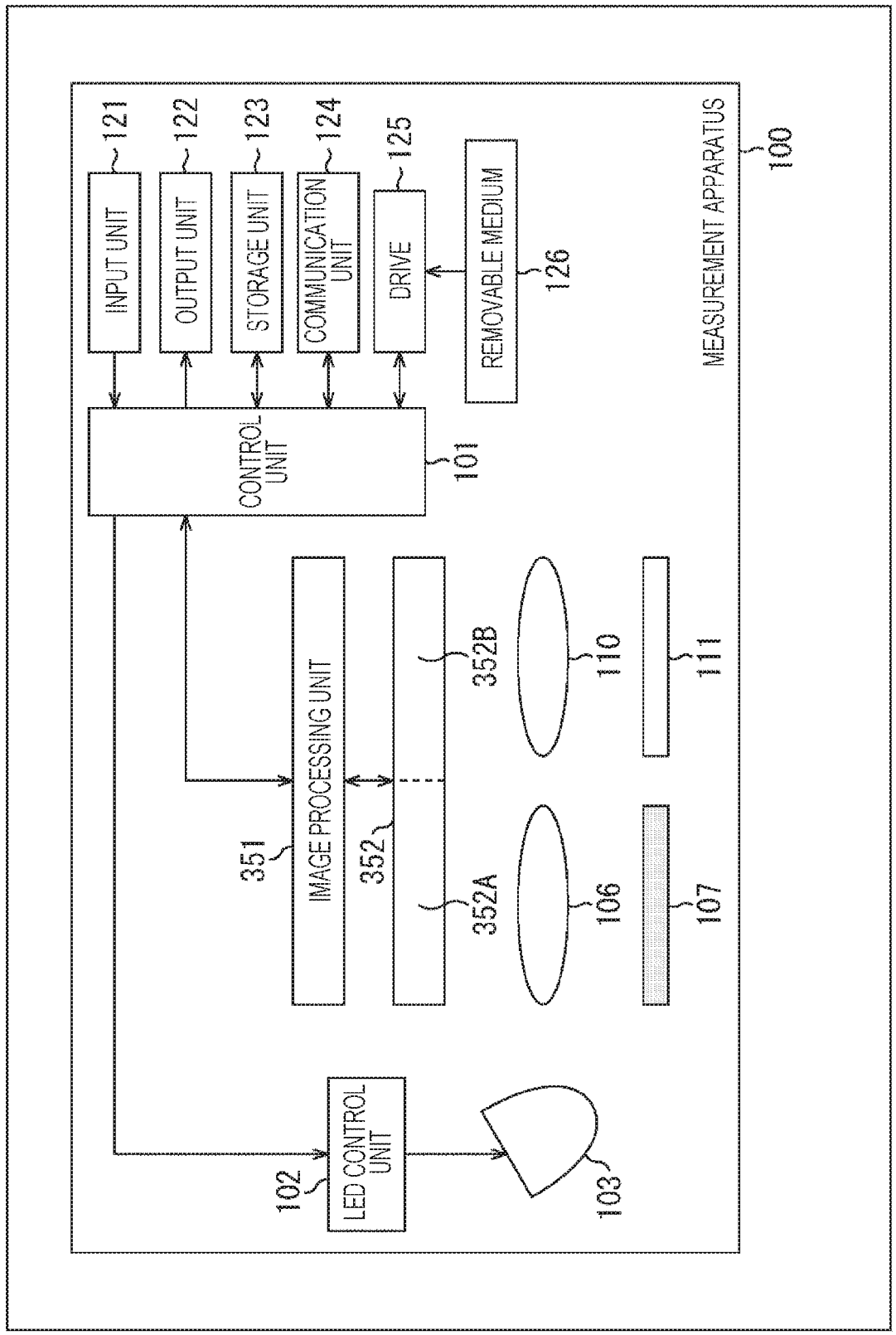
FIG. 36 is a block diagram illustrating a main configuration example of a measurement apparatus.

For example, in the case of the example illustrated in FIG. 36, the measurement apparatus 100 includes an image processing unit 351 and a CIS 352 instead of the image processing unit 104, the CIS 105, the image processing unit 108, and the CIS 109 in the example of FIG. 3. Under the control of the control unit 101, the image processing unit 351 performs image processing on the captured image obtained in the CIS 352.

The pixel region of the CIS 352 is provided with a pixel region 352A for receiving light in the near-ultraviolet to blue wavelength band (near-ultraviolet light or blue light) and a pixel region 352B for receiving light in the blue to red wavelength band (light other than near-ultraviolet light or blue light). The lens 106 and the filter 107, which are components for the first reflected light, are provided at positions corresponding to the pixel region 352A, and the lens 110 and the filter 111, which are components for the second reflected light, are provided in the pixel region 352B. That is, the CIS 352 generates a UV reflection image (excitation light image) in the pixel region 352A and generates a fluorescence image (radiation image) in the pixel region 352B. The CIS 352 supplies the UV reflection image obtained in the pixel region 352A and the fluorescence image obtained in the pixel region 352B to the image processing unit 351.

The image processing unit 351 performs image processing on each of the UV reflection image and the fluorescence image supplied from the CIS 352. The content of this image processing is arbitrary. The image processing unit 351 supplies the UV reflection image and the fluorescence image subjected to the image processing to the control unit 101.

With such a configuration, it is possible to implement a single CIS, and it is possible to further reduce the size of the casing of the measurement apparatus 100 and to reduce the cost and power consumption.

In addition, the pixels that receive the first reflected light and the pixels that receive the second reflected light may be separated by the on-chip filter formed in each pixel without dividing the pixel region as described above.

Figure 37:
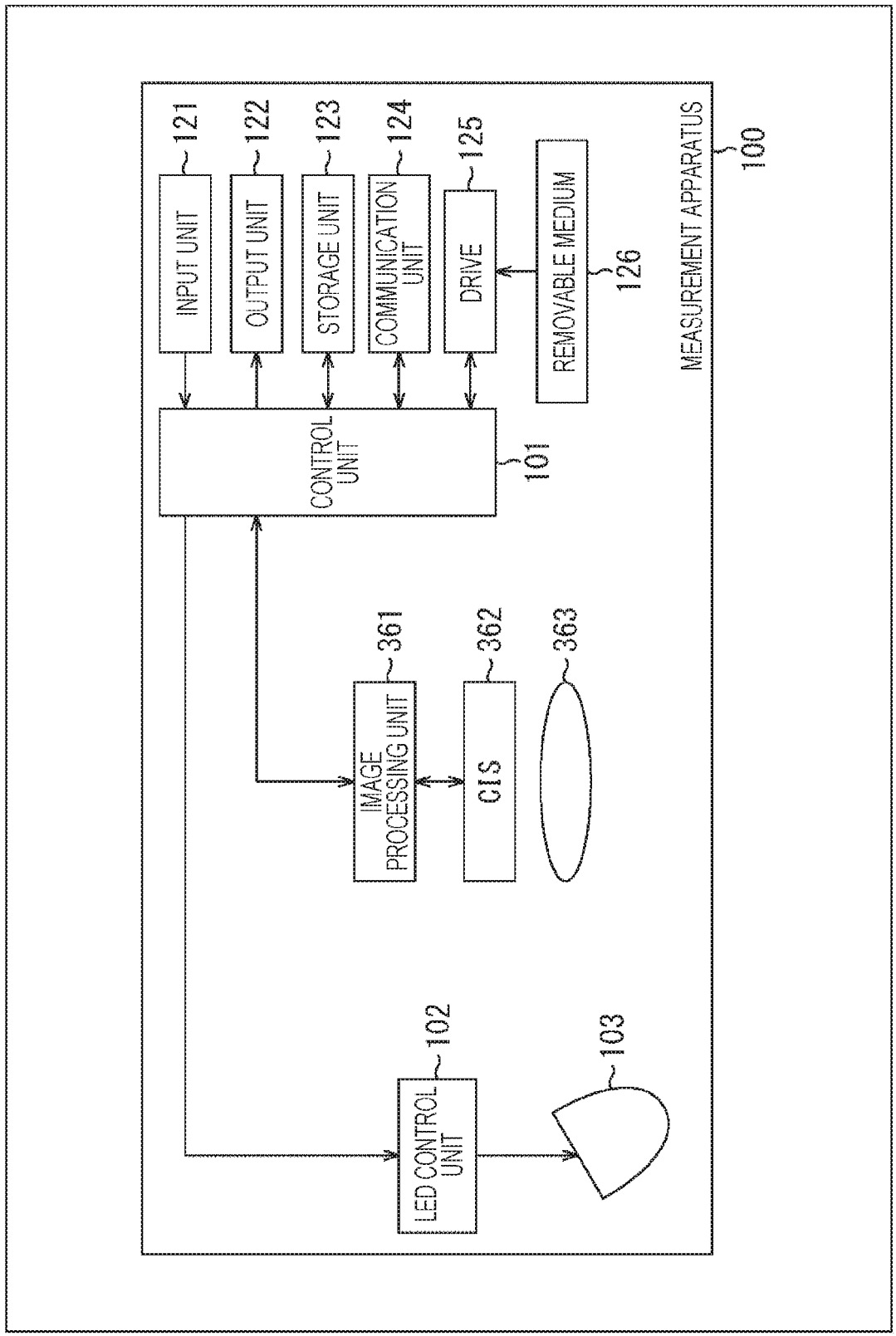
FIG. 37 is a block diagram illustrating a main configuration example of a measurement apparatus.

For example, in the case of the example illustrated in FIG. 37, the measurement apparatus 100 includes an image processing unit 361, a CIS 362, and a lens 363 instead of the image processing unit 104, the CIS 105, the lens 106, the filter 107, the image processing unit 108, the CIS 109, the lens 110, and the filter 111 of the example of FIG. 3. Under the control of the control unit 101, the image processing unit 361 performs image processing on the captured image obtained in the CIS 362. The reflected light is condensed on the pixel region of the CIS 362 by the lens 363.

An on-chip filter is formed in each pixel of the CIS 362, and each wavelength band of the incident light is limited by the on-chip filter. For example, the CIS 362 is provided with the pixels in which an on-chip filter that transmits the wavelength band of the first reflected light is formed and the pixels in which an on-chip filter that transmits the wavelength band of the second reflected light is formed.

That is, the CIS 362 receives the light in the near-ultraviolet to blue wavelength band and the light in the blue to red wavelength band at different pixels and generates the UV reflection image (excitation light image) and the fluorescence image (radiation image), respectively. The CIS 362 supplies the generated UV reflection image and the generated fluorescence image to the image processing unit 361.

The image processing unit 361 performs image processing on each of the UV reflection image and the fluorescence image supplied from the CIS 362. The content of this image processing is arbitrary. The image processing unit 361 supplies the UV reflection image and the fluorescence image subjected to the image processing to the control unit 101.

With such a configuration, it is possible to reduce the number of filters and lenses, and it is possible to further reduce the size of the casing of the measurement apparatus 100 and to reduce the cost and power consumption.

<Filter>

In addition, the configuration of the on-chip filter in this case is arbitrary. In other words, the layout (arrangement) of the pixels that receive the first reflected light and the pixels that receive the second reflected light in the CIS 362 is arbitrary.

Figure 38B:
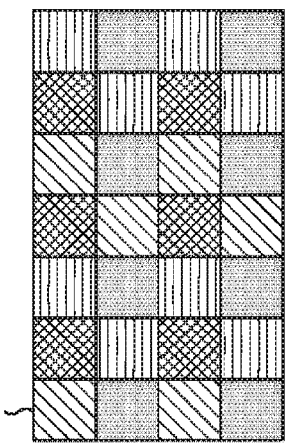
FIGS. 38A, 38B, and 38C are diagrams illustrating an example of an on-chip filter.
Figure 38C:
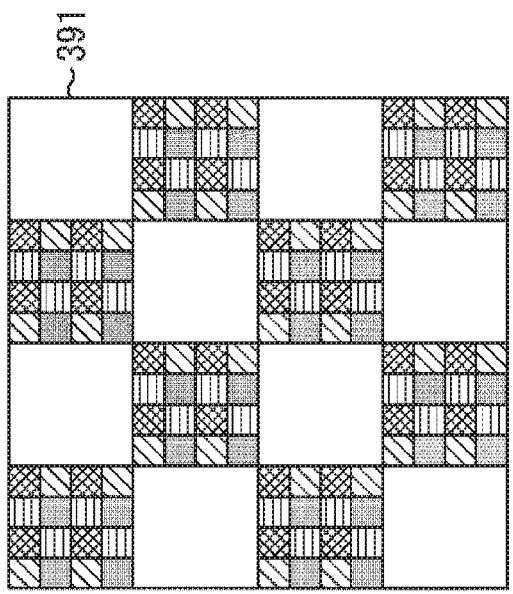
Figure 38A:
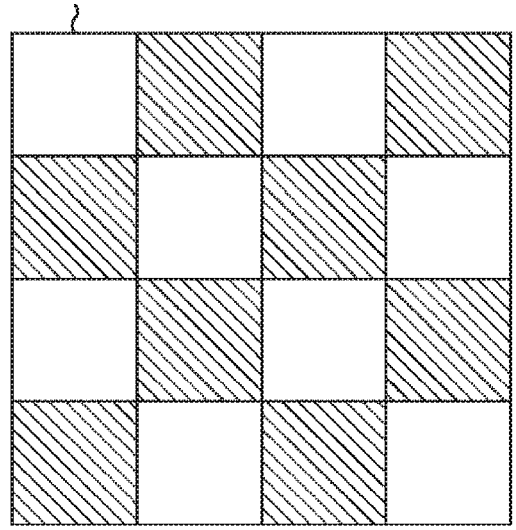

For example, as in the on-chip filter 371 illustrated in FIG. 38A, a filter that transmits light in the near-ultraviolet to blue wavelength band and a filter that transmits light in the blue to red wavelength band (fluorescence light) may be arranged alternately in the up-down direction and the left-right direction in the figure. In FIG. 38A, each square of the on-chip filter 371 indicates a filter for one pixel. In the figure, the square with a slanted pattern indicates a filter that transmits light (that is, first reflected light) in the near-ultraviolet to blue wavelength band, and the white square indicates a filter that transmits light (that is, second reflected light) in a wavelength band of which wavelength is larger than that of blue. That is, a UV reflection image (first reflection image) is obtained in a pixel group in which a filter indicated by the square with a slanted pattern in the CIS 362 is formed, and a fluorescence image (second reflection image) is obtained in a pixel group in which a filter indicated by the white square is formed. With such a configuration, it is possible to uniformly distribute the pixels that receive the first reflected light and the pixels that receive the second reflected light, and the range (angle of view) of the UV reflection image and the range (angle of view) of the fluorescence image can be allowed to be closer to each other (substantially the same as each other).

In addition, in the on-chip filter 371, the alignment (arrangement) of the filters is arbitrary and is not limited to the example of FIG. 38A.

Furthermore, for example, as in the on-chip filter 381 illustrated in FIG. 38B, the on-chip filter may be configured with a filter that transmits light in the near-ultraviolet to blue wavelength band, a filter that transmits light in the blue wavelength band, a filter that transmits light in the red wavelength band, and a filter that transmits light in the green wavelength band. In FIG. 38B, each square of the on-chip filter 381 indicates a filter for one pixel. Therefore, In the figure, the square with a slanted pattern indicates a filter that transmits light in the near-ultraviolet to blue wavelength band, the gray square illustrates a filter that transmits light in the blue wavelength band, the square with a lattice pattern indicates a filter that transmits light in the red wavelength band, and a square with a horizontal stripe pattern indicates a filter that transmits light in the green wavelength band. That is, the square with a slanted pattern indicates a filter of a pixel that receives the first reflected light, and the other squares indicate filters of pixels that receive visible light.

That is, a UV reflection image is obtained in a pixel group in which a filter indicated by a square with a slanted pattern in the CIS 362 is formed, and a captured image of visible light is obtained in a pixel group in which filters indicated by other squares are formed. Then, each pixel value of a fluorescence image (an image of light in a blue to visible wavelength band) is obtained by using the blue pixel value B, the red pixel value R, and the green pixel value G of the captured image of visible light. For example, each pixel value of the fluorescence image may be obtained by gray scale conversion (luminance conversion) of these pixel values (R, G, B).

For example, as illustrated in the following Formula (8), a simple average of the pixel values (R, G, B) may be set as the pixel value Y of the fluorescence image.

[Mathematical Formula 8]

$$Y=(R+G+B)/3 \qquad (8)$$

Furthermore, for example, as illustrated in the following Formula (9), a weighted average of these pixel values (R, G, B) in the National Television Standards Committee (NTSC) method may be set as the pixel value Y of the fluorescence image.

[Mathematical Formula 9]

$$Y=0.299 \times R+0.587 \times G+0.114 \times B \qquad (9)$$

Furthermore, for example, as illustrated in the following Formula (10), a weighted average of the pixel values (R, G, B) in a high definition television (HDTV) method may be set as the pixel value Y of the fluorescence image.

[Mathematical Formula 10]

$$Y=0.2126 \times R+0.7152 \times G+0.0722 \times B \qquad (10)$$

With such a configuration, it is possible not only to allow the range of the UV reflection image and the range of the fluorescence image to be closer to each other (to be substantially the same) but also to obtain a captured image of visible light. Furthermore, since the second reflected light can be received by a larger number of pixels (with a wider area), comparatively weak fluorescence light can be detected with high sensitivity.

In addition, in the on-chip filter 381, the alignment (arrangement) of the filters is arbitrary and is not limited to the example of FIG. 38B.

Furthermore, for example, as in the case of the on-chip filter 391 illustrated in FIG. 38C, separately from the filter that transmits light in the near-ultraviolet to blue wavelength band and the filter that transmits visible light, a filter (a filter that transmits the second reflected light) that transmits light in a wavelength band of which is longer than that of blue may be provided. In addition, the size of each pixel may not be the same.

For example, the white square illustrated in the on-chip filter 391 indicates a filter that transmits light in a wavelength band of which is longer than that of blue, similarly to the case of FIG. 38A. That is, the on-chip filter 391 is provided with a filter that transmits light in the near-ultraviolet to blue wavelength band, a filter that transmits light in the blue wavelength band, a filter that transmits light in the red wavelength band, a filter that transmits light in the green wavelength band, and a filter that transmits light of the wavelength band of which is longer than the wavelength of the blue light.

Then, as illustrated in FIG. 38C, the filter that transmits the light in the wavelength band of which wavelength is larger than the blue is formed so as to be larger than the other filters. That is, the pixels that receive the second reflected light (fluorescence light) are formed so as to be larger than the other pixels. For example, in the case of FIG. 38C, the pixel that receives the second reflected light is formed so as to have the same size as the sum of those of the other pixels. With such a configuration, comparatively weak fluorescence light can be detected with higher sensitivity. That is, the luminance of the fluorescence image can be increased.

Furthermore, the pixel value of the image of light in the blue to visible wavelength band is obtained by using the blue pixel value B, the red pixel value R, and the green pixel value G of the captured image of visible light, and the pixel value may be added to the pixel value of the pixel where the filter indicated by a white square is formed. For example, these pixel values may be summed as expressed in the following Formula (11).

$$\alpha \times \text{fluorescence light pixel data} + (1-\alpha) \times \text{blue visible data} \qquad (11)$$

In Formula (11), the pixel data for fluorescence light indicates the pixel value of a pixel provided with a filter (white rectangle) that transmits light in a wavelength band of which wavelength is larger than that of blue, that is, a pixel value of a fluorescence image. In addition, the blue visible data indicates the pixel values of the image of light in the blue to visible wavelength band calculated by using the blue pixel value B, the red pixel value R, and the green pixel value G. With such a configuration, comparatively weak fluorescence light can be detected with higher sensitivity. That is, it is possible to further increase the luminance of the fluorescence image.

In addition, in the on-chip filter 391, the alignment (arrangement) of the filters is arbitrary and is not limited to the example of FIG. 38C.

<Light Receiving Unit>

In addition, the specifications of the CIS (for example, CIS 105 and CIS 109 in FIG. 3, CIS 352 in FIG. 36, and CIS 362 in FIG. 37) as the light receiving unit are arbitrary. For example, the CIS may have a vertical spectroscopic structure so that light of a plurality of wavelength bands can be received at each pixel distinguishably (in such a manner that light of each wavelength band can be received as a different light (component)). In addition, the method of arrangement of the pixels in the pixel region of the CIS is arbitrary, may be in a matrix form, or may be, for example, a method of arrangement other than a matrix form such as a honeycomb structure.

In addition, in the above description, the CIS is used as an embodiment of the light receiving unit. However, the light receiving unit may be an image sensor having a plurality of pixels or any sensor (that is, any sensor as long as the sensor photoelectrically converts incident light of arbitrary wavelength band at a plurality of positions (pixels) and can obtain information including a plurality of pixel data (image data)) having a function equivalent to the image sensor. For example, instead of the CIS, an image sensor using a charge coupled device (CCD) may be used as the light receiving unit. Furthermore, a plurality of PDs arranged in a two-dimensional shape (for example, array) may be used as the light receiving unit.

<Light Emitting Unit/Irradiation Light>

In the above description, the LED 103 emits the irradiation light irradiated to the human body 130, but the light emitting unit (light emitter) that emits the irradiation light is arbitrary and may be a light emitter other than the LED. Furthermore, the number of light emitters constituting the light emitting unit is also arbitrary, and irradiation light may be irradiated by a plurality of light emitters. In addition, in the above description, the LED 103 emits near-ultraviolet light, but the LED may also be allowed to emit light including near-ultraviolet wavelength band such as white light.

<Measurement System>

The present technology can also be applied to a system including a plurality of devices. For example, the present technology can be applied to a system having the above-described measurement apparatus 100.

Figure 39C:
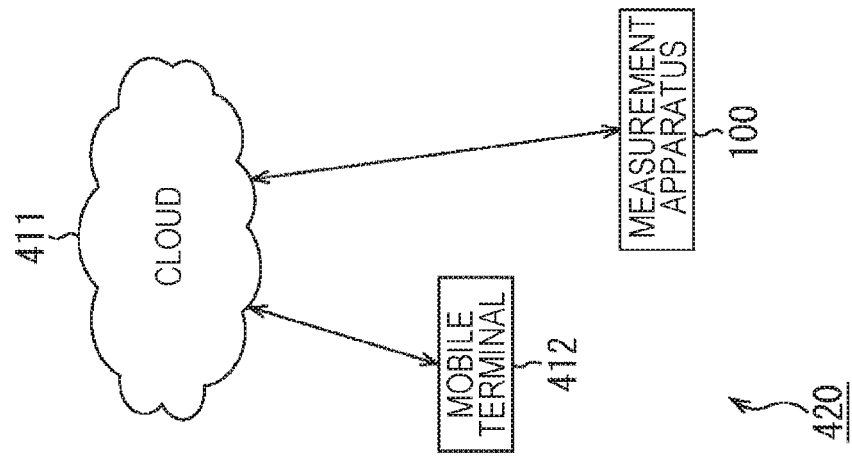
FIGS. 39A, 39B, and 39C are block diagrams illustrating a main configuration example of a measurement system.
Figure 39B:
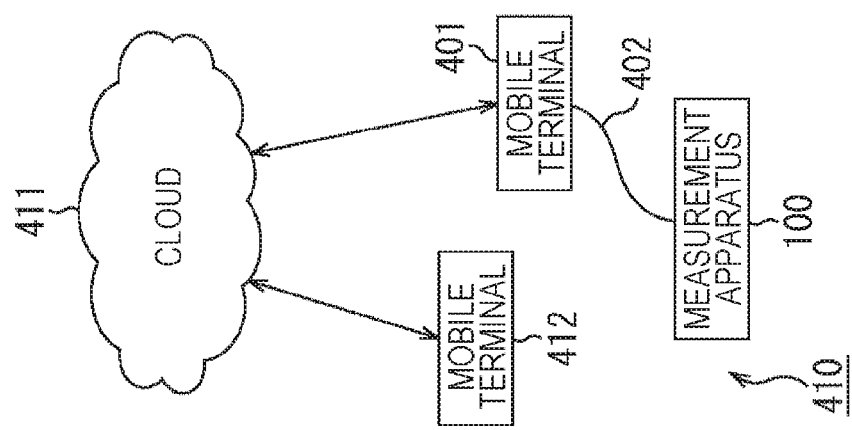
Figure 39A:
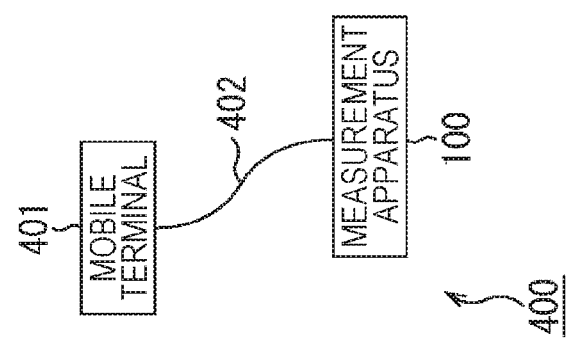

For example, the present technology can be applied to a measurement system 400 as illustrated in FIG. 39A. The measurement system 400 illustrated in FIG. 39A includes a measurement apparatus 100 and a mobile terminal 401. The mobile terminal 401 is, for example, a mobile information processing apparatus such as a tablet terminal or a smartphone and is connected to the measurement apparatus 100 via a cable 402 in a communicable manner. For example, the mobile terminal 401 performs wired communication with the measurement apparatus 100 via the cable 402 and cooperatively performs processing relating to measurement.

For example, the mobile terminal 401 controls the measurement apparatus 100. Under the control of the mobile terminal 401, the measurement apparatus 100 performs processing (for example, light irradiation, imaging, indicator calculation, and the like) relating to measurement of the indicator relating to the AGEs as described above and transmits the measurement result (indicator value or the like) to the mobile terminal 401. The mobile terminal 401 acquires the measurement result and performs processing such as analysis of the indicator and imaging/display of the measurement result.

With such a configuration, for example, since the measurement results and the like can be displayed on the monitor of the mobile terminal 401, there is no need to provide a monitor to the measurement apparatus 100, and thus, it is possible to reduce the size of the casing of the measurement apparatus 100. In other words, by enlarging the monitor of the mobile terminal 401, it is possible to display the measurement result and the like so as to be more easily viewed without enlarging the casing of the measurement apparatus 100.

In addition, with such a configuration, for example, a user interface that receives a user operation on the measurement apparatus 100 can be provided to the mobile terminal 401. For example, an image of the user interface can be displayed on the monitor of the mobile terminal 401, and an input operation for the image can be received by a touch panel superimposed on the monitor. Therefore, it is not necessary to provide such a user interface to the measurement apparatus 100, so that it is possible to miniaturize the casing of the measurement apparatus 100 by that amount. In other words, by increasing the size of the user interface provided to the mobile terminal 401, it is possible to improve the operability of the measurement apparatus 100 without increasing the size of the casing of the measurement apparatus 100.

In addition, the measurement apparatus 100 and the mobile terminal 401 may perform wireless communication. In this case, the cable 402 may be omitted.

Furthermore, for example, as in the measurement system 410 illustrated in FIG. 39B, data may be stored in the cloud 411. The measurement system 410 includes a cloud 411 and a mobile terminal 412 in addition to the configuration of the measurement system 400. The mobile terminal 401 and the mobile terminal 412 are connected to the cloud 411 in a wired or wireless communicable manner. In this measurement system 410, the mobile terminal 401 can supply the measurement result from the measurement apparatus 100 to the cloud 411.

The cloud 411 accumulates the measurement results acquired from the mobile terminal 401. In addition, similarly, the cloud 411 can acquire and accumulate the measurement results from a plurality of mobile terminals 401. Furthermore, the cloud 411 can also take statistics on the stored measurement results. Furthermore, the cloud 411 can supply the statistical data to the mobile terminal 401 and allow the statistical data to be displayed. Furthermore, the cloud 411 can supply the statistical data and the accumulated data to other mobile terminals 412 and allow the statistical data and the accumulated data to be displayed.

Similarly to the mobile terminal 401, the mobile terminal 412 is a mobile information processing apparatus such as a tablet terminal or a smartphone and can access, for example, the cloud 411 and acquire information such as measurement results and statistical data. Furthermore, for example, the mobile terminal 412 can convert the acquired information into an image and allow the image to be displayed on the monitor.

With such a configuration, the measurement system 410 can supply more various services such as accumulation of the measurement results, creation of the statistical information, or display of the statistical information and the like on the monitor. Furthermore, for example, in a device different from the mobile terminal 401 that controls the measurement apparatus 100 similarly to the mobile terminal 412, it is possible to utilize or display such information.

In addition, as in the measurement system 420 illustrated in FIG. 39C, the measurement apparatus 100 may be connected to the cloud 411 in a communicable manner. In this case, for example, the measurement apparatus 100 can display the measurement result on the monitor or supply the measurement result to the cloud 411. The cloud 411 can accumulate, analyze, and take statistics of the measurement results. Furthermore, the cloud 411 can supply the measurement results and the statistical data to the mobile terminal 412. The mobile terminal 412 can convert the acquired measurement result and statistical data into an image, display the image, or further analyze the acquired measurement result and statistical data. In addition, like the mobile terminal 401, the mobile terminal 412 may control the measurement apparatus 100 via the cloud 411.

The configuration of the measurement system to which the present technology can be applied is arbitrary and is not limited to the example of FIGS. 39A, 39B, and 39C.

<Others>

The portion on which measurement is performed by the measurement apparatus 100 is arbitrary. For example, a portion may be a user's foot (sole of foot, instep of foot, finger, shin, calf, thigh, and the like), may be a user's arm (shoulder, elbow, palm, back of the hand, finger, and the like), may be a user's torso (chest, abdomen, lower abdomen, buttocks, armpits, and the like), or may be a user's head (forehead, occipital region, head top, face, jaw, ears, neck, and the like) may be used. Of course, it may be a portion other than these.

Furthermore, the present technology is not limited to the above-described measurement apparatus but can be applied to any apparatuses. For example, the present technology can be applied to arbitrary optical apparatuses, electronic apparatuses, imaging apparatuses, information processing apparatuses, and the like. That is, the subject to be measured is arbitrary and may be, for example, a living body (for example, an animal or a plant such as a dog, a cat, and the like) other than a human body or may be an object that is not a living body. For example, the subject to be measured may be an inorganic material. In addition, the indicator to be measured is arbitrary and may not be relating to AGEs. That is, the substance causing excitation is arbitrary and may be a substance other than AGEs. In addition, the wavelength band of the irradiation light needs to be a band including an excitation wavelength that causes excitation of a predetermined substance, and the wavelength band depends on the characteristics of the substance causing the excitation. Similarly, the first wavelength band and the second wavelength band to be measured for obtaining a desired indicator also depend on the characteristics of the substance.

6. Others

<Application Example of Present Technology>

The system and device according to the above-described embodiment can be applied to any system or electronic apparatus. Furthermore, the present technology can be applied to image processing systems and image processing apparatuses in arbitrary fields such as traffic, medical care, crime prevention, agriculture, livestock industry, mining, beauty, factory, household appliance, weather, and natural surveillance.

For example, the present technology can also be applied to a system that projects and captures an image to be used for appreciation. In addition, for example, the present technology can be applied to a system used for traffic. Furthermore, for example, the present technology can be applied to a system used for security. In addition, for example, the present technology can be applied to a system used for sports. Furthermore, for example, the present technology can be applied to a system used for agriculture. Furthermore, for example, the present technology can be applied to a system used for livestock industry. Furthermore, the present technology can be applied to a system for monitoring natural conditions of, for example, volcanoes, forests, oceans, and the like, a meteorological observation system for observing, for example, weather, temperature, humidity, wind speed, sunshine time and the like, and a system for observing the ecology of wildlife such as, birds, fish, reptiles, amphibians, mammals, insects, and plants.

<Software>

The series of processes described above can be executed by hardware or can be executed by software. In a case where a series of the processes described above is executed by software, programs constituting the software are installed from a network or a recording medium.

For example, in the case of the measurement apparatus 100 illustrated in FIG. 3, this recording medium is configured as a removable medium 126 on which a program is recorded, which is distributed so as to transmit a program to a user separately from the main body of the device. In this case, for example, by attaching the removable medium 126 to the drive 125, this program stored in the removable medium 126 can be read out and installed in the storage unit 123.

In addition, this program can also be provided via a wired or wireless transmission medium such as a local area network, the Internet, or digital satellite broadcasting. For example, in the case of the measurement apparatus 100 of FIG. 3, the program can be received by the communication unit 124 and installed in the storage unit 123.

Besides, this program can be installed in advance in a storage unit, a ROM, or the like. For example, in the case of the measurement apparatus 100 of FIG. 3, the program can be installed in advance in the storage unit 123 or in the ROM or the like in the control unit 101.

In addition, in the program executed by the computer, the processes of steps of describing the program can be executed in time sequence order according to the order described in this specification, or can be executed in parallel or individually at necessary timing such as a time of being called. Furthermore, the processes of steps of describing this program can be executed in parallel with the processes of another program, or can be executed in combination with the processes of another program.

In addition, the process of each of steps can described above can be executed by each of the above-described apparatuses or arbitrary apparatuses other than the above-described apparatuses. In this case, the apparatus that executes the processes can have the functions (function blocks or the like) necessary for executing the processes described above. Furthermore, information necessary for the processes can be transmitted to the apparatus as appropriate.

<Others>

The embodiments of the present technology are not limited to the above-described embodiments, and various modifications are possible without departing from the spirit of the present technology.

For example, in the present specification, a system denotes a group of a plurality of constituent elements (devices, modules (parts), and the like), and it does not matter whether or not all constituent elements are in the same casing. Therefore, a plurality of devices that are accommodated in separate casings and are connected via a network and one device that accommodates a plurality of modules in one casing are systems.

Furthermore, for example, the configuration described as one device (or processing unit) may be divided and configured as a plurality of devices (or processing units). On the contrary, configurations described above as a plurality of devices (or processing units) may be collectively configured as one device (or processing unit). In addition, of course, configurations other than those described above may be added to the configuration of each device (or each processing unit). Furthermore, as long as the configuration and operation of the entire system are substantially the same, a portion of the configuration of a certain device (or a processing unit) may be included in the configuration of another device (or another processing unit).

Furthermore, for example, the present technology can adopt a configuration of cloud computing in which one function is shared to be jointly processed by a plurality of devices via a network.

Furthermore, for example, each step described in the above-described flowchart can be executed by one device or can be shared to be executed by a plurality of devices. Furthermore, in a case where a plurality of processes is included in one step, the plurality of processes included in the one step can be executed by one device or can be shared to be executed by a plurality of devices.

Furthermore, the present technology can be implemented not only as a device or a system but also as all configurations provided to devices constituting the device or the system, for example, a processor as a system large scale integration (LSI) or the like, a module using a plurality of processors or the like, a unit using a plurality of modules or the like, a set in which other functions are added to the unit (that is, a configuration of a portion of the device).

In addition, as long as there is no inconsistency, each of the plurality of the present technologies described in this specification can be independently implemented as a single entity. Of course, it can also be possible to implement by combining a plurality of arbitrary present technologies. For example, the present technology described in any of the embodiments can be implemented in combination with the present technology described in other embodiments. In addition, the arbitrary present technology described above can be implemented in combination with another present technology not mentioned above.

In addition, the present technology can also have the following configurations.

(1) An optical apparatus including:

a light emitting unit that emits irradiation light including a predetermined irradiation wavelength band;

a light receiving unit that receives, at a plurality of pixels, first reflected light being reflected light in a first wavelength band obtained by reflection of the irradiation light emitted by the light emitting unit on a predetermined object and second reflected light being reflected light in a second wavelength band obtained by reflection of the irradiation light on the object; and an indicator processing unit that obtains a value of a predetermined indicator relating to a region of a predetermined range of the object on the basis of a received light amount of each of the first reflected light and the second reflected light received by the light receiving unit.

(2) The optical apparatus according to (1), further including a brightness adjustment unit that performs adjustment of brightness of a first reflection image being an image obtained by the light receiving unit receiving the first reflected light, a second reflection image being an image obtained by the light receiving unit receiving the second reflected light, or both of the first reflection image and the second reflection image.

(3) The optical apparatus according to (1) or (2), in which the brightness adjustment unit determines the brightness of the first reflection image by using average luminance of the first reflected light received by the light receiving unit, determines the brightness of the second reflection image by using average luminance or contrast of the second reflected light received by the light receiving unit, or performs both of the determining of the brightness of the first reflection image and the determining of the brightness of the second reflection image.

(4) The optical apparatus according to any one of (1) to (3), in which, in a case where the brightness is insufficient, the brightness adjustment unit increases the number of surrounding pixels, pixel values of the surrounding pixels being added to each pixel of the first reflection image and the second reflection image, increases a light amount of the irradiation light emitted by the light emitting unit, increases an exposure time of the light receiving unit, or performs a plurality of the increasing of the number of surrounding pixels, the increasing of the light amount of the irradiation light, and the increasing of the exposure time.

(5) The optical apparatus according to any one of (1) to (4), in which the brightness adjustment unit performs the adjustment of the brightness of the first reflection image, the second reflection image, or both of the first reflection image and the second reflection image for each pixel or for each predetermined partial region including a plurality of pixels.

(6) The optical apparatus according to any one of (1) to (5), further including an indicator updating unit that updates the value of the indicator obtained by the indicator processing unit on the basis of a predetermined error factor.

(7) The optical apparatus according to any one of (1) to (6), further including an effectiveness degree processing unit that obtains an effectiveness degree of the value of the indicator on the basis of the error factor, in which the indicator updating unit is configured to update the value of the indicator by using the effectiveness degree obtained by the effectiveness degree processing unit.

(8) The optical apparatus according to any one of (1) to (7), further including an influence degree processing unit that obtains an influence degree by the error factor, in which the effectiveness degree processing unit is configured to obtain the effectiveness degree by using the influence degree obtained by the influence degree processing unit.

(9) The optical apparatus according to any one of (1) to (8), further including an error factor amount processing unit that obtains an amount of the error factor, in which the influence degree processing unit is configured to obtain the influence degree by using the amount of the error factor obtained by the error factor amount processing unit.

(10) The optical apparatus according to any one of (1) to (9), in which the error factor is melanin, and the error factor amount processing unit is configured to obtain an amount of the melanin by using a near-infrared image being an image obtained by the light receiving unit receiving light in a near-infrared wavelength band and a red image being an image obtained by the light receiving unit receiving light in a red wavelength band.

(11) The optical apparatus according to any one of (1) to (10), in which the error factor is redness, and the error factor amount processing unit is configured to obtain an amount of the redness by using a red image being an image obtained by the light receiving unit receiving light in a red wavelength band and a green image being an image obtained by the light receiving unit receiving light in a green wavelength band.

(12) The optical apparatus according to any one of (1) to (11), in which the indicator updating unit is configured to update the value of the indicator for each pixel, for each predetermined partial region including a plurality of pixels or for a part of the region.

(13) The optical apparatus according to any one of (1) to (12), further including an indicator control unit that controls an output of the value of the indicator obtained by the indicator processing unit on the basis of a predetermined error factor.

(14) The optical apparatus according to any one of (1) to (13), further including an effectiveness degree processing unit that obtains an effectiveness degree of the value of the indicator on the basis of the error factor, in which the indicator control unit is configured to control the output of the value of the indicator by using an integrated value of the effectiveness degree obtained by the effectiveness degree processing unit.

(15) The optical apparatus according to any one of (1) to (14), in which the indicator control unit outputs the value of the indicator in a case where the integrated value is larger than a predetermined threshold value and performs error processing in a case where the integrated value is equal to or smaller than the predetermined threshold value.

(16) The optical apparatus according to any one of (1) to (15), in which the irradiation wavelength band is a near-ultraviolet wavelength band, and the light emitting unit is configured to emit near-ultraviolet light being light in the near-ultraviolet wavelength band as the irradiation light.

(17) The optical apparatus according to any one of (1) to (16), in which the first wavelength band is a near-ultraviolet to blue wavelength band, and the second wavelength band is a blue to red wavelength band.

(18) The optical apparatus according to any one of (1) to (17), in which the light receiving unit includes a CMOS image sensor (CIS) that receives the first reflected light and a CIS that receives the second reflected light, includes a CIS having a first pixel region receiving the first reflected light and a second pixel region receiving the second reflected light, or includes a CIS having a pixel provided with a first on-chip filter that transmits the first wavelength band and a pixel provided with a second on-chip filter that transmits the second wavelength band, the CIS receiving the first reflected light in a pixel provided with the first on-chip filter and receiving the second reflected light in a pixel provided with the second on-chip filter.

(19) The optical apparatus according to any one of (1) to (18), in which the object is a living body, and the indicator is skin autofluorescence.

(20) An information processing method including:

emitting irradiation light including a predetermined irradiation wavelength band, receiving, at a plurality of pixels, first reflected light being a reflected light in a first wavelength band obtained by reflection of the emitted irradiation light on a predetermined object and second reflected light being reflected light in a second wavelength band obtained by reflection of the irradiation light on the object; and obtaining a value of a predetermined indicator relating to a region in a predetermined range of the object on the basis of a received light amount of each of the received first reflected light and the received second reflected light.

REFERENCE SIGNS LIST

100 Measurement apparatus
101 Control unit
102 LED control unit
103 LED
104 Image processing unit
105 CIS
106 Lens
107 Filter
108 Image processing unit
109 CIS
110 Lens
111 Filter
121 Input unit
122 Output unit
123 Storage unit
124 Communication unit
125 Drive
126 Removable medium
130 Human body
151 UV light irradiation control unit
152 Imaging control unit
153 UV brightness adjustment unit
154 Fluorescence brightness adjustment unit
155 AGEs amount calculation unit
156 Output control unit
161 UV average luminance calculation unit
162 UV average luminance determination unit
163 Pixel addition mode setting unit
164 Light amount setting unit
165 Error processing unit
171 Fluorescence average luminance calculation unit
172 Fluorescence average luminance determination unit
173 Pixel addition mode setting unit
174 Light amount setting unit
175 Error processing unit
190 Image
191 Melanin
192 Redness
201 Fluorescence light contrast calculation unit
202 Fluorescence light contrast determination unit
211 Long-accumulation mode setting unit
213 Long-accumulation mode setting unit
231 AGEs amount calculation processing unit
232 Melanin amount influence suppression unit
233 Redness amount influence suppression unit
234 AGEs effectiveness degree calculation unit
235 Effective AGEs amount calculation unit
241 Near-infrared light irradiation control unit
242 Red light irradiation control unit
243 Imaging control unit
244 Melanin amount calculation unit
245 Melanin amount influence degree calculation unit
251 Red light irradiation control unit
252 Green light irradiation control unit
253 Imaging control unit
254 Redness amount calculation unit
255 Redness amount influence degree calculation unit
321 Integrated value determination unit
351 Image processing unit
352 CIS
361 Image processing unit
362 CIS
363 Lens
371, 381, 391 On-chip filter
400 Measurement system
401 Mobile terminal
402 Cable
410 Measurement system
411 Cloud
412 Mobile terminal
420 Measurement system

The invention claimed is:

1. An optical apparatus, comprising:
a plurality of light emitting diodes (LEDs) configured to emit irradiation light including a specific irradiation wavelength band; and
circuitry configured to:
receive, at a plurality of pixels, first reflected light in a first wavelength band obtained by reflection of the irradiation light on an object;
receive second reflected light in a second wavelength band obtained by the reflection of the irradiation light on the object;
determine a value of a specific indicator, associated with a region of the object irradiated by the irradiation light, based on a received light amount of each of the first reflected light and the second reflected light;

determine an amount of an error factor based on a difference in a light intensity of a red image and a light intensity of a green image, wherein the red image is obtained from light received by reflection of the irradiation light in a red wavelength band on the object, the red wavelength band is a part of the second wavelength band, the green image is obtained from light received by reflection of the irradiation light in a green wavelength band on the object, the green wavelength band is a part of the second wavelength band, and the error factor comprises redness associated with a portion of the object irradiated with the irradiation light; and update the value of the specific indicator based on the amount of the error factor.

2. The optical apparatus according to claim 1, wherein the circuitry is further configured to adjust brightness of at least one of a first reflection image obtained from the received first reflected light or a second reflection image obtained from the received second reflected light, the first reflection image is an ultraviolet reflection image of near-ultraviolet to blue wavelength bands, and the second reflection image is a fluorescence reflection image of blue to red wavelength bands.

3. The optical apparatus according to claim 2, wherein the circuitry is further configured to:

determine the brightness of the first reflection image based on an average luminance of the received first reflected light;

determine the brightness of the second reflection image based on at least one of an average luminance of the received second reflected light or a contrast of the received second reflected light;

determine, upon determination of the brightness of at least one of the first reflected image or the second reflected image, whether the brightness of at least one of the first reflected image or the second reflected image is insufficient; and adjust the brightness of at least one of the first reflected image or the second reflected image based on at least one of an increase in a number of surrounding pixels for each pixel of the first reflection image and the second reflection image, an increase in pixel values of the surrounding pixels, an increase in a light amount of the irradiation light emitted by at least one LED of the plurality of LEDs, or an increase in an exposure time of the at least one LED.

4. The optical apparatus according to claim 2, wherein the circuitry is further configured to adjust the brightness of one of each pixel of at least one of the first reflection image or the second reflection image or each specific partial region including a plurality of pixels of at least one of the first reflection image or the second reflection image.

5. The optical apparatus according to claim 1, wherein the circuitry is further configured to:

determine an effectiveness degree of the value of the specific indicator based on the error factor; and update the value of the specific indicator based on the effectiveness degree.

6. The optical apparatus according to claim 5, wherein the circuitry is further configured to:

determine an influence degree based on the error factor, wherein the influence degree indicates a magnitude of influence of the error factor on the specific indicator; and determine the effectiveness degree based on the influence degree.

7. The optical apparatus according to claim 6, wherein the circuitry is further configured to determine the influence degree based on the amount of the error factor.

8. The optical apparatus according to claim 7, wherein the error factor further comprises melanin, the circuitry is further configured to determine an amount of the melanin based on a near-infrared image obtained in a near-infrared wavelength band and the red image obtained in the red wavelength band, and the near-infrared wavelength band is different from the first wavelength band and the second wavelength band.

9. The optical apparatus according to claim 1, wherein the circuitry is further configured to update the value of the specific indicator for at least one of each pixel of at least one of a first reflection image or a second reflection image, or each specific partial region including a plurality of pixels of at least one of the first reflection image or the second reflection image, the first reflection image is obtained from the received first reflected light and the second reflection image is obtained by the received second reflected light, the first reflection image is an ultraviolet reflection image of near-ultraviolet to blue wavelength bands, and the second reflection image is a fluorescence reflection image of blue to red wavelength bands.

10. The optical apparatus according to claim 1, wherein the circuitry is further configured to control an output of the value of the specific indicator based on the error factor.

11. The optical apparatus according to claim 10, wherein the circuitry is further configured to:

determine an effectiveness degree of the value of the specific indicator based on the error factor for at least one of each pixel of at least one of a first reflected image or a second reflected image, or each partial region in at least one of the first reflected image or the second reflected image, wherein the first reflection image is obtained from the received first reflected light and the second reflection image is obtained by the received second reflected light, the first reflection image is an ultraviolet reflection image of near-ultraviolet to blue wavelength bands, and the second reflection image is a fluorescence reflection image of blue to red wavelength bands;

integrate a value of the effectiveness degree determined for each pixel or each partial region for at least one of the first reflected image or the second reflected image; and control the output of the value of the specific indicator based on the integrated value of the effectiveness degree.

12. The optical apparatus according to claim 11, wherein the circuitry is further configured to one of:

output the value of the specific indicator in a case where the integrated value is larger than a threshold value; or execute an error processing operation in a case where the integrated value is equal to or smaller than the threshold value.

13. The optical apparatus according to claim 1,
wherein the specific irradiation wavelength band is a near-ultraviolet wavelength band, and
the plurality of LEDs is configured to emit near-ultraviolet light in the near-ultraviolet wavelength band as the irradiation light.

14. The optical apparatus according to claim 1,
wherein the first wavelength band is a near-ultraviolet to blue wavelength band, and
the second wavelength band is a blue to red wavelength band.

15. The optical apparatus according to claim 1, wherein the circuitry comprises at least one of:
a first complementary metal oxide semiconductor (CMOS) image sensor (CIS) configured to receive the first reflected light and a second CIS configured to receive the second reflected light,
a CIS having a first pixel region configured to receive the first reflected light and a second pixel region configured to receive the second reflected light, or
a CIS comprising a first pixel with a first on-chip filter and a second pixel with a second on-chip filter, wherein
the first on-chip filter is configured to transmit the first wavelength band,
the second on-chip filter is configured to transmit the second wavelength band, and
the CIS is configured to:
receive the first reflected light in the first pixel with the first on-chip filter, and
receive the second reflected light in the second pixel with the second on-chip filter.

16. The optical apparatus according to claim 1, wherein the object is a living body, and
the specific indicator is skin autofluorescence.

17. An information processing method, comprising:
emitting irradiation light including a specific irradiation wavelength band;
receiving, at a plurality of pixels, first reflected light in a first wavelength band obtained by reflection of the irradiation light on an object;
receiving, at the plurality of pixels, second reflected light in a second wavelength band obtained by the reflection of the irradiation light on the object;
determining a value of a specific indicator, associated with a region of the object irradiated by the irradiation light, based on a received light amount of each of the first reflected light and the second reflected light;
determining an amount of an error factor based on a difference in a light intensity of a red image and a light intensity of a green image, wherein
the red image is obtained from light received by reflection of the irradiation light in a red wavelength band on the object,
the red wavelength band is a part of the second wavelength band,
the green image is obtained from light received by reflection of the irradiation light in a green wavelength band on the object,
the green wavelength band is a part of the second wavelength band, and
the error factor comprises redness associated with a portion of the object irradiated with the irradiation light; and
updating the value of the specific indicator based on the amount of the error factor.

* * * * *